US012723245B2

(12) United States Patent
Ben-Yehezkel

(10) Patent No.: US 12,723,245 B2
(45) Date of Patent: Sep. 1, 2026

(54) METHODS AND COMPOSITIONS FOR PHASED SEQUENCING

(71) Applicant: Element Biosciences, Inc., San Diego, CA (US)

(72) Inventor: Tuval Ben-Yehezkel, Sunnyvale, CA (US)

(73) Assignee: Element Biosciences, Inc., San Diego, CA (US)

( * ) Notice: Subject to any disclaimer, the term of this patent is extended or adjusted under 35 U.S.C. 154(b) by 1154 days.

(21) Appl. No.: 17/571,032

(22) Filed: Jan. 7, 2022

(65) Prior Publication Data

US 2022/0389408 A1 Dec. 8, 2022

Related U.S. Application Data

(63) Continuation of application No. 16/328,663, filed as application No. PCT/US2017/049496 on Aug. 30, 2017.

(60) Provisional application No. 62/381,547, filed on Aug. 30, 2016.

(51) Int. Cl.
*C12N 15/10* (2006.01)
*C12Q 1/6874* (2018.01)
*C12Q 1/6855* (2018.01)

(52) U.S. Cl.
CPC ....... *C12N 15/1065* (2013.01); *C12Q 1/6874* (2013.01); *C12Q 1/6855* (2013.01)

(58) Field of Classification Search
None
See application file for complete search history.

(56) References Cited

U.S. PATENT DOCUMENTS 5,476,930 A 12/1995 Letsinger et al.
5,780,613 A 7/1998 Letsinger et al.
7,115,400 B1 10/2006 Adessi et al.
7,315,019 B2 1/2008 Turner et al.
7,582,420 B2 9/2009 Oliphant et al.
7,901,891 B2 3/2011 Drmanac
7,955,794 B2 6/2011 Shen et al.
8,003,354 B2 8/2011 Shen et al.
8,298,767 B2 10/2012 Brenner et al.
8,563,274 B2 10/2013 Brenner et al.
8,603,749 B2 12/2013 Gillevet
8,652,779 B2 2/2014 Turner et al.
8,653,779 B2 2/2014 Yashiro et al.
8,673,562 B2 3/2014 Drmanac
8,679,756 B1 3/2014 Brenner et al.
8,765,375 B2 7/2014 Drmanac
8,765,379 B2 7/2014 Drmanac
8,765,382 B2 7/2014 Drmanac
8,771,957 B2 7/2014 Drmanac
8,771,958 B2 7/2014 Drmanac
8,829,171 B2 9/2014 Steemers et al.
8,835,358 B2 9/2014 Fodor et al.
8,932,812 B2 1/2015 Hogers et al.
9,023,769 B2 5/2015 Drmanac et al.
9,034,580 B2 5/2015 Cantor
9,074,242 B2 7/2015 Larson et al.
9,085,798 B2 7/2015 Chee
9,102,980 B2 8/2015 Brenner et al.
9,127,307 B2 9/2015 Adler, Jr. et al.
9,150,852 B2 10/2015 Samuels et al.
9,260,753 B2 2/2016 Xie et al.
9,290,809 B2 3/2016 Fodor et al.
9,404,156 B2 8/2016 Hicks et al.
9,453,262 B2 9/2016 Gillevet
9,476,095 B2 10/2016 Vogelstein et al.
9,514,272 B2 12/2016 Kermani et al.
9,524,369 B2 12/2016 Drmanac et al.
9,574,230 B2 2/2017 Van Eijk et al.
9,637,785 B2 5/2017 Drmanac
10,415,029 B2 9/2019 Dambacher et al.
11,180,749 B2 11/2021 Dambacher et al.
11,255,847 B2 2/2022 Schnall-Levin
2009/0186343 A1 7/2009 Wang et al.
2009/0263361 A1 10/2009 Lee et al.
2009/0298075 A1 12/2009 Travers et al.
2011/0129834 A1 6/2011 Chen et al.
2012/0190663 A1 7/2012 Gornik et al.
2012/0196754 A1 8/2012 Quake et al.
2012/0270214 A1 10/2012 Bernitz et al.
2013/0054151 A1 2/2013 Kermani et al.

(Continued)

FOREIGN PATENT DOCUMENTS

CN 104093890 A 10/2014
CN 104736722 A 6/2015

(Continued)

OTHER PUBLICATIONS

Bankevich, A. et al., "SPAdes: A New Genome Assembly Algorithm and Its Applications to Single-Cell Sequencing," Journal of Computational Biology, 2012, 19(5):455-477.
Extended European Search Report for European Application No. 17847517.4 mailed Apr. 7, 2020, 5 pages.
FASTX-Toolkit. FASTQ/A short-reads pre-processing tools. Accessed online Aug. 1, 2022 at hannonlab.cshl.edu/fastx_toolkit/, 2 pages.
Hayashi, K. et al., "Highly accurate genome sequences of *Escherichia coli* K-12 strains MG1655 and W3110," Molecular Systems Biology, 2006, 1-5.

(Continued)

*Primary Examiner* — Juliet C Switzer
*Assistant Examiner* — Brian Ellis Young
(74) *Attorney, Agent, or Firm* — FENWICK & WEST LLP; Heidi A. Erlacher; Jessica D. Cande

(57) ABSTRACT

The present disclosure provides methods and compositions for molecular tagging of complex populations of nucleic acid molecules. The disclosure provides methods and compositions to obtain phase information of tagged nucleic acid molecules from high-throughput nucleic acid sequencing data.

29 Claims, 37 Drawing Sheets

Specification includes a Sequence Listing.

(56) References Cited

U.S. PATENT DOCUMENTS

| | | | | |
|---|---|---|---|---|
| 2013/0079231 | A1 | 3/2013 | Pushkarev et al. | |
| 2013/0157870 | A1 | 6/2013 | Pushkarev et al. | |
| 2013/0224751 | A1 | 8/2013 | Olson et al. | |
| 2013/0237432 | A1 | 9/2013 | Li et al. | |
| 2014/0018246 | A1 | 1/2014 | Drmanac | |
| 2014/0034497 | A1 | 2/2014 | Davis et al. | |
| 2014/0120534 | A1* | 5/2014 | Bernitz | C12Q 1/6809 435/6.11 |
| 2014/0134614 | A1* | 5/2014 | Dong | C12Q 1/6851 536/24.33 |
| 2014/0256568 | A1 | 9/2014 | Link | |
| 2015/0057163 | A1 | 2/2015 | Rotem et al. | |
| 2015/0057947 | A1 | 2/2015 | Drmanac et al. | |
| 2015/0087535 | A1 | 3/2015 | Patel | |
| 2015/0094961 | A1 | 4/2015 | Kermani et al. | |
| 2015/0148239 | A1 | 5/2015 | Peter et al. | |
| 2015/0259674 | A1 | 9/2015 | Steelman et al. | |
| 2015/0265995 | A1 | 9/2015 | Head et al. | |
| 2016/0026758 | A1 | 1/2016 | Jabara et al. | |
| 2016/0040228 | A1 | 2/2016 | De Wit et al. | |
| 2016/0076023 | A1 | 3/2016 | Quake et al. | |
| 2016/0152972 | A1 | 6/2016 | Stapleton et al. | |
| 2018/0030506 | A1* | 2/2018 | Fujioka | C12Q 1/6806 |

FOREIGN PATENT DOCUMENTS

| | | | |
|---|---|---|---|
| EP | 2463386 | A2 | 6/2012 |
| EP | 2599877 | A1 | 6/2013 |
| WO | WO-2004070005 | A2 | 8/2004 |
| WO | WO 2005/111240 | A2 | 11/2005 |
| WO | WO-2007010252 | A1 | 1/2007 |
| WO | WO-2008076406 | A2 | 6/2008 |
| WO | WO-2011074960 | A1 | 6/2011 |
| WO | WO-2012000445 | A1 | 1/2012 |
| WO | WO-2012061832 | A1 | 5/2012 |
| WO | WO-2012103154 | A1 | 8/2012 |
| WO | WO-2014071361 | A1 | 5/2014 |
| WO | WO-2014145820 | A2 | 9/2014 |
| WO | WO-2014171898 | A2 | 10/2014 |
| WO | WO-2014145820 | A3 | 11/2014 |
| WO | WO-2015084802 | A1 | 6/2015 |
| WO | WO-2015117040 | A1 | 8/2015 |
| WO | WO-2018045109 | A1 | 3/2018 |

OTHER PUBLICATIONS

International Search Report and Written Opinion issued in PCT/US2017/049496 dated Jan. 18, 2018, 16 pages.

Jiang, H. et al. "Skewer: a fast and accurate adapter trimmer for next-generation sequencing paired-end reads," BMC Bioinformatics, 2014, 15(182):1-12.

Lim, B. N. et al. "Directed evolution of nucleotide-based libraries using lambda exonuclease," BioTechniques, Dec. 2012, 53(6):357-364.

Margulies, M., et al., "Genome sequencing in microfabricated high-density picolitre reactors," Nature, Sep. 15, 2005, 437(7057):376-380, and 1 page corrigendum.

Peng, Z. et al. "Generation of Long Insert Pairs Using a Cre-LoxP Inverse PCR Approach," PLoS One, Jan. 2012, 7(1):e29437:1-8.

Rothberg, J.M. et al., "An integrated semiconductor device enabling non-optical genome sequencing," Nature, 2011, Jul. 21, 2011, 475:348-352.

Rungpragayphan, S. et al. "High-throughput, Cloning-independent Protein Library Construction by Combining Single-molecule DNA Amplification with in Vitro Expression," J Mol Biol., 2002, 318:395-405.

Scythe—A Bayesian adapter trimmer (version 0.994 BETA). Accessed online Aug. 1, 2022 at github.com/vsbuffalo/scythe, 7 pages.

Shendure, J. et al. "Accurate Multiplex Polony Sequencing of an Evolved Bacterial Genome," Science, Sep. 9, 2005, 309:1728-1732.

Souza, V. et al. "Long-term experimental evolution in *Escherichia coli*. V. Effects of recombination with immigrant genotypes on the rate of bacterial evolution," Journal of Evolutionary Biology, 1997, 10:743-769.

Stapleton, J. A. and Swartz, J.R. "A Cell-Free Microtiter Plate Screen for Improved [FeFe] Hydrogenases," PLoS One, May 2010, 5(5):e10554:1-8.

Trimmomatic: "A flexible read trimming tool for Illumina NGS data," USADELLA.org, Accessed online Aug. 1, 2022 at usadellab.org/cms/?page=trimmomatic, 6 pages.

Zerbino, D. R. and Birney, E. "Velvet: de novo assembly using very short reads" European Bioinformatics Institute, 2008, 1 page.

Zerbino, D.R. and Birney, E. "Velvet: Algorithms for de novo short read assembly using de Bruijn graphs," Genome Research, 2008, 18:821-829.

Levy, S.E., and Myers, R.M. "Advancements in Next-Generation Sequencing," Annu. Rev. Genom. Hum. Genet., 2016, 17:95-115.

Anderson, J.P. et al.; Fluorescent Structural DNA Nanoballs Functionalized with Phosphate-Linked Nucleotide Triphosphates. Nano Letters 10(3):788-792 (2010).

Chen, X., et al.; "Efficient in situ barcode sequencing using padlock probe-based BaristaSeq," Nucleic Acids Research; 46(4):e22 pp. 1-10 (2018).

Mignardi, M., et al.; "Fourth-generation sequencing in the cell and the clinic," Genome Med.;6(4):31; pp. 1-4 (2014).

Wang, F. et al., "Tequila-seq: a versatile and low-cost method for targeted long-read RNA sequencing," Nat Commun., (2023); 14(1):4760, pp. 1-15.

* cited by examiner

Structure of an Adapter with Barcode and Elongation Priming Probe

PCR Priming (PP)
Barcode (BC)
DNA Sequencing Adaptor (SA)
ssDNA Elongation Priming (EP)

Step 0

Step 1a – Tagging single molecules with unique barcodes

Ligation-based tagging of single molecules with adapter

PCR Priming (PP)
Barcode (BC)
DNA Sequencing Adaptor (SA)
ssDNA Elongation Priming (EP)
Target nucleic acid-annealing sequence

Step 1b – PCR Amplification of tagged single molecules

PCR Primer (PP) can be terminal 5'

PCR Priming (PP)
Barcode (BC)
DNA Sequencing Adaptor (SA)
ssDNA Elongation Priming (EP)

Step 2 – Generating ssDNA from dsDNA (in the case the PP segment is not 5′ terminal and isn't removed

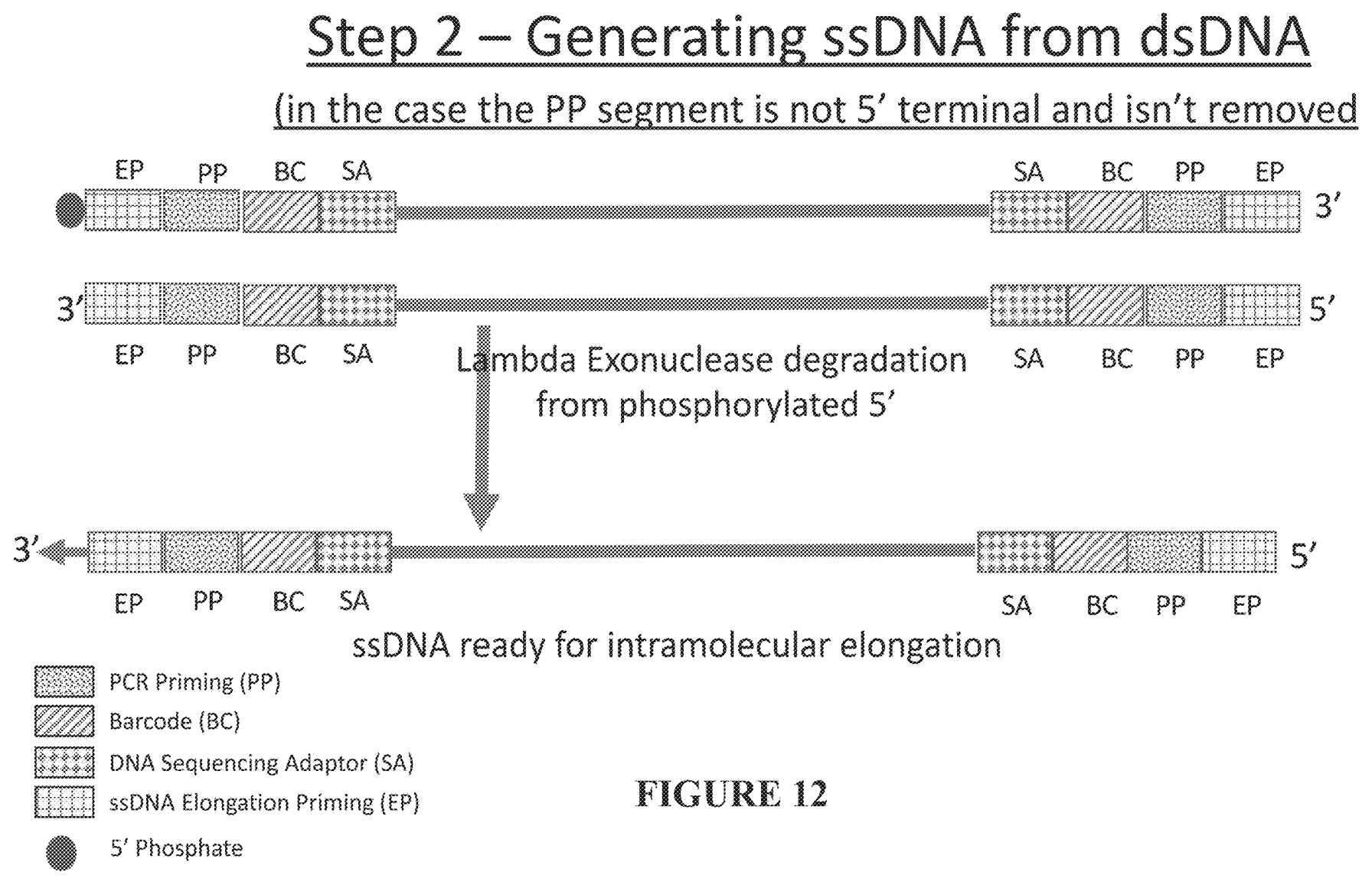

EP PP BC SA SA BC PP EP 3′

3′ EP PP BC SA SA BC PP EP 5′

Lambda Exonuclease degradation from phosphorylated 5′

3′ EP PP BC SA SA BC PP EP 5′ ssDNA ready for intramolecular elongation

PCR Priming (PP)
Barcode (BC)
DNA Sequencing Adaptor (SA)
ssDNA Elongation Priming (EP)
5′ Phosphate

FIGURE 12

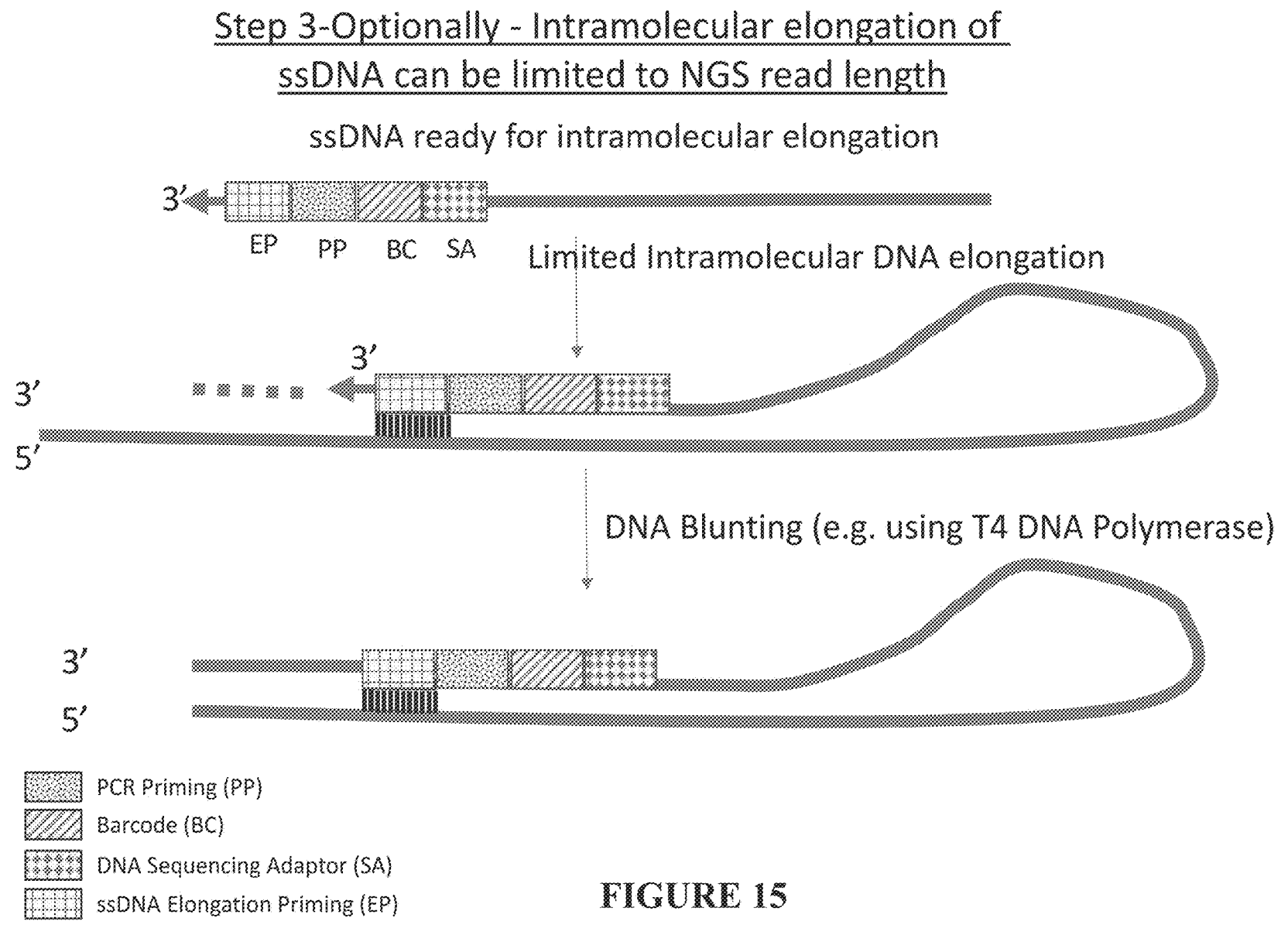

Step 3-Optionally - Intramolecular elongation of ssDNA can be limited to NGS read length ssDNA ready for intramolecular elongation

3'
EP
PP
BC
SA

Limited Intramolecular DNA elongation

3'
3'
5'

DNA Blunting (e.g. using T4 DNA Polymerase)

3'
5'

PCR Priming (PP)
Barcode (BC)
DNA Sequencing Adaptor (SA)
ssDNA Elongation Priming (EP)

FIGURE 15

Figure 16:
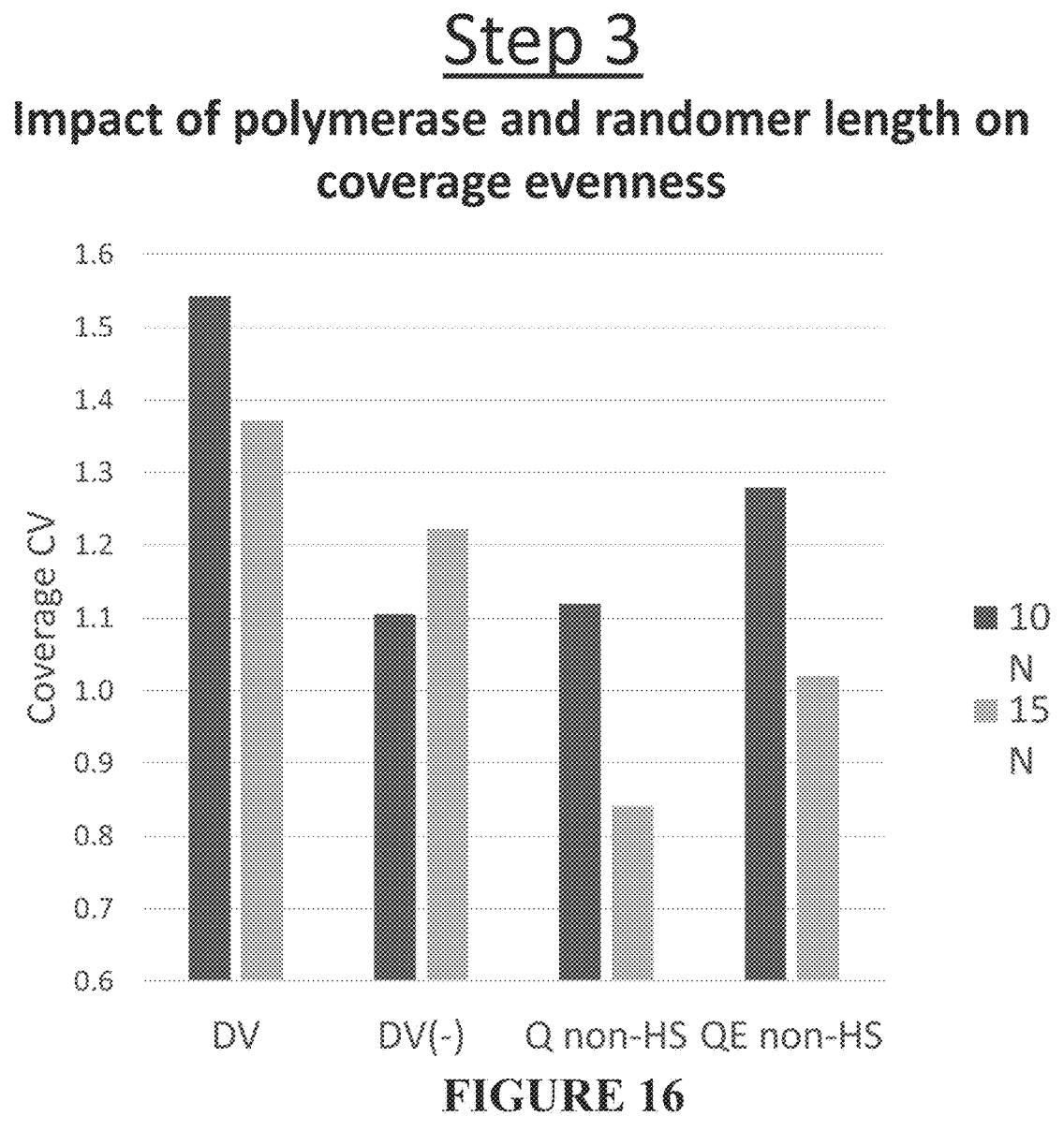

Step 3

Impact of polymerase and randomer length on coverage evenness

Coverage CV 1.6
1.5
1.4
1.3
1.2
1.1
1.0
0.9
0.8
0.7
0.6

DV
DV(-)
Q non-HS
QE non-HS

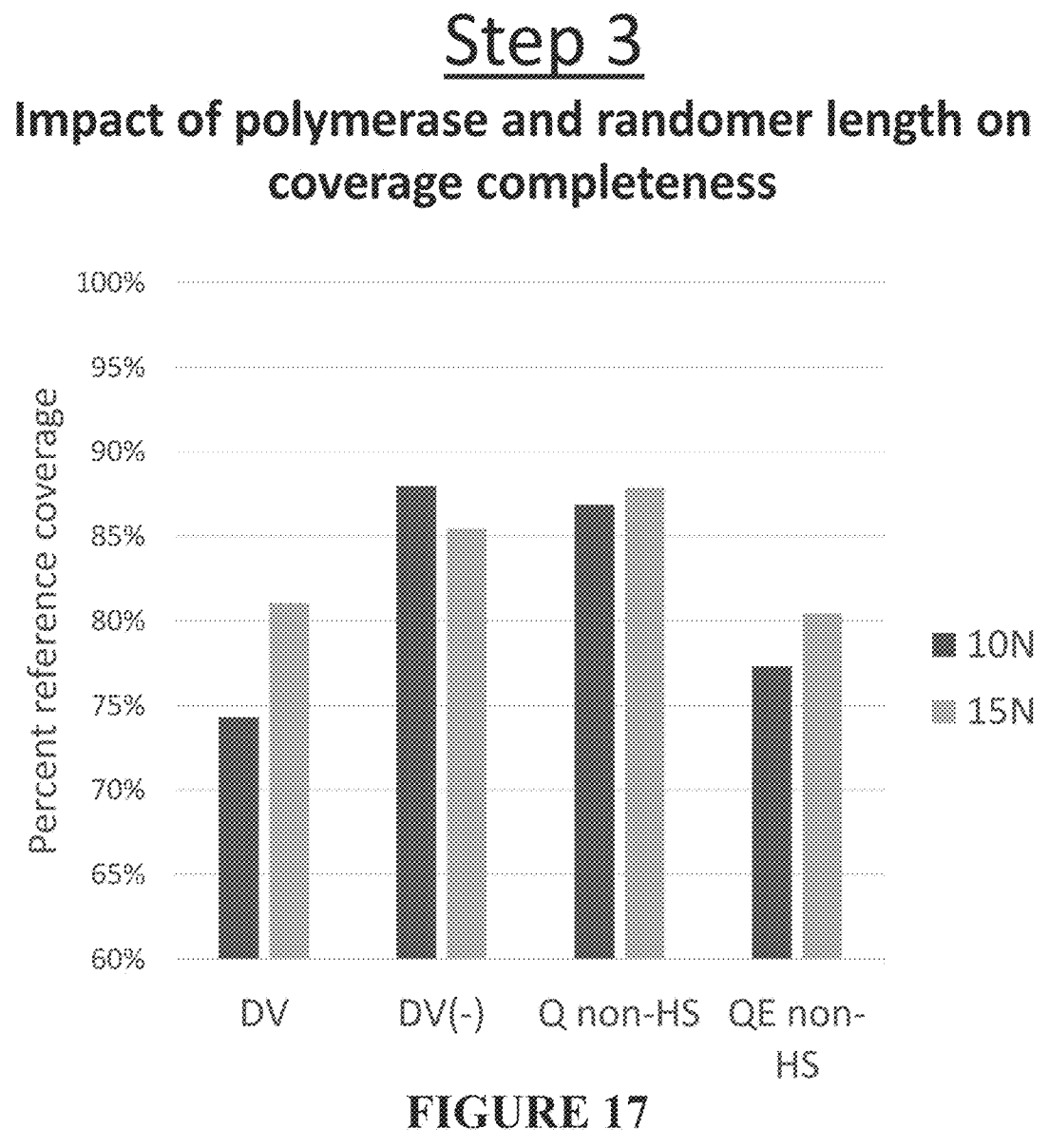

Step 3

Impact of polymerase and randomer length on coverage completeness

Percent reference coverage

100%
95%
90%
85%
80%
75%
70%
65%
60%

DV
DV(-)
Q non-HS
QE non-HS 10N
15N

FIGURE 17

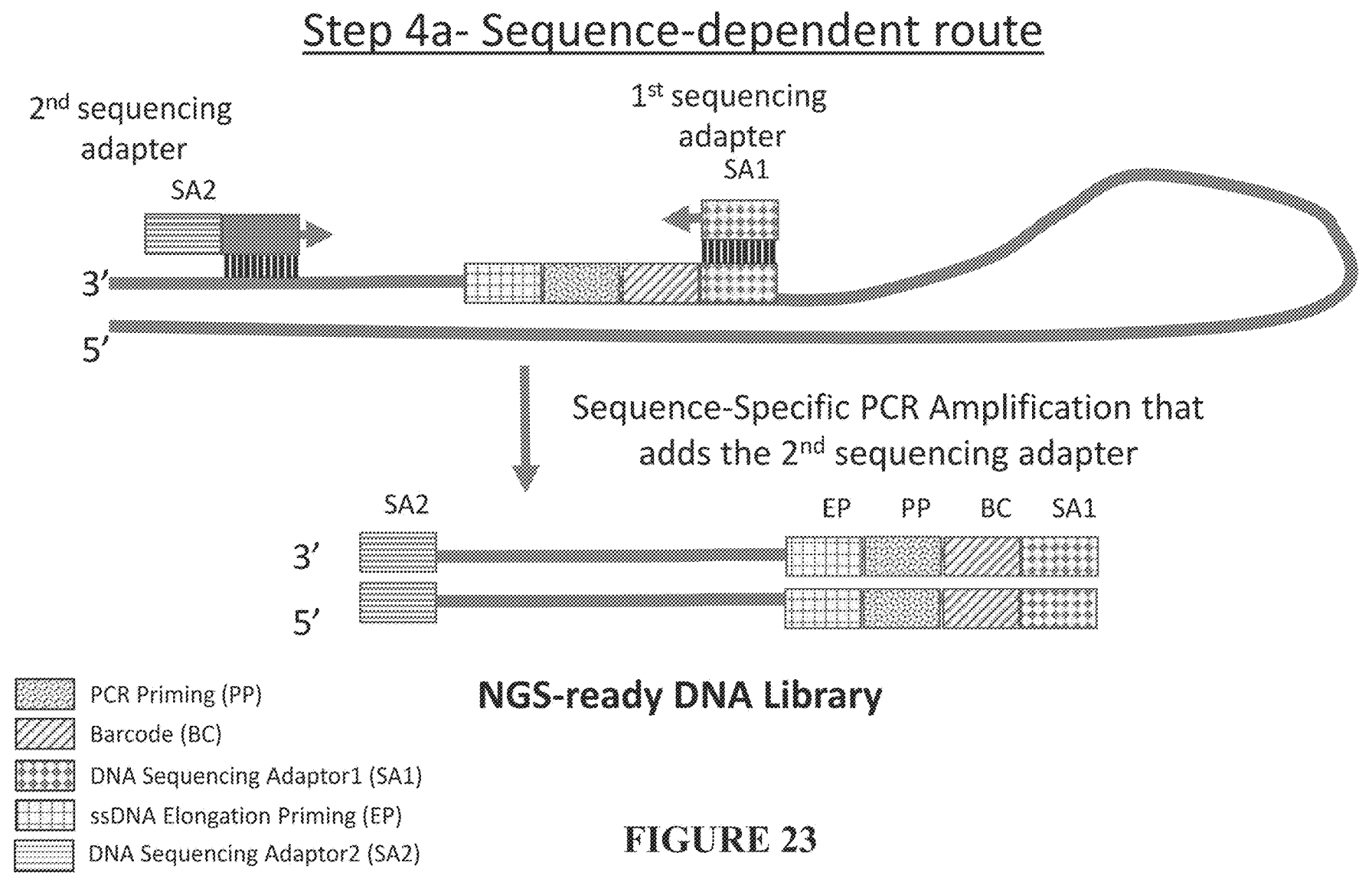

Step 4a- Sequence-dependent route

2nd sequencing adapter

SA2

1st sequencing adapter

SA1

3'

5'

Sequence-Specific PCR Amplification that adds the 2nd sequencing adapter

SA2

EP PP BC SA1

3'

5'

PCR Priming (PP)

Barcode (BC)

DNA Sequencing Adaptor1 (SA1)

ssDNA Elongation Priming (EP)

DNA Sequencing Adaptor2 (SA2)

NGS-ready DNA Library

FIGURE 23

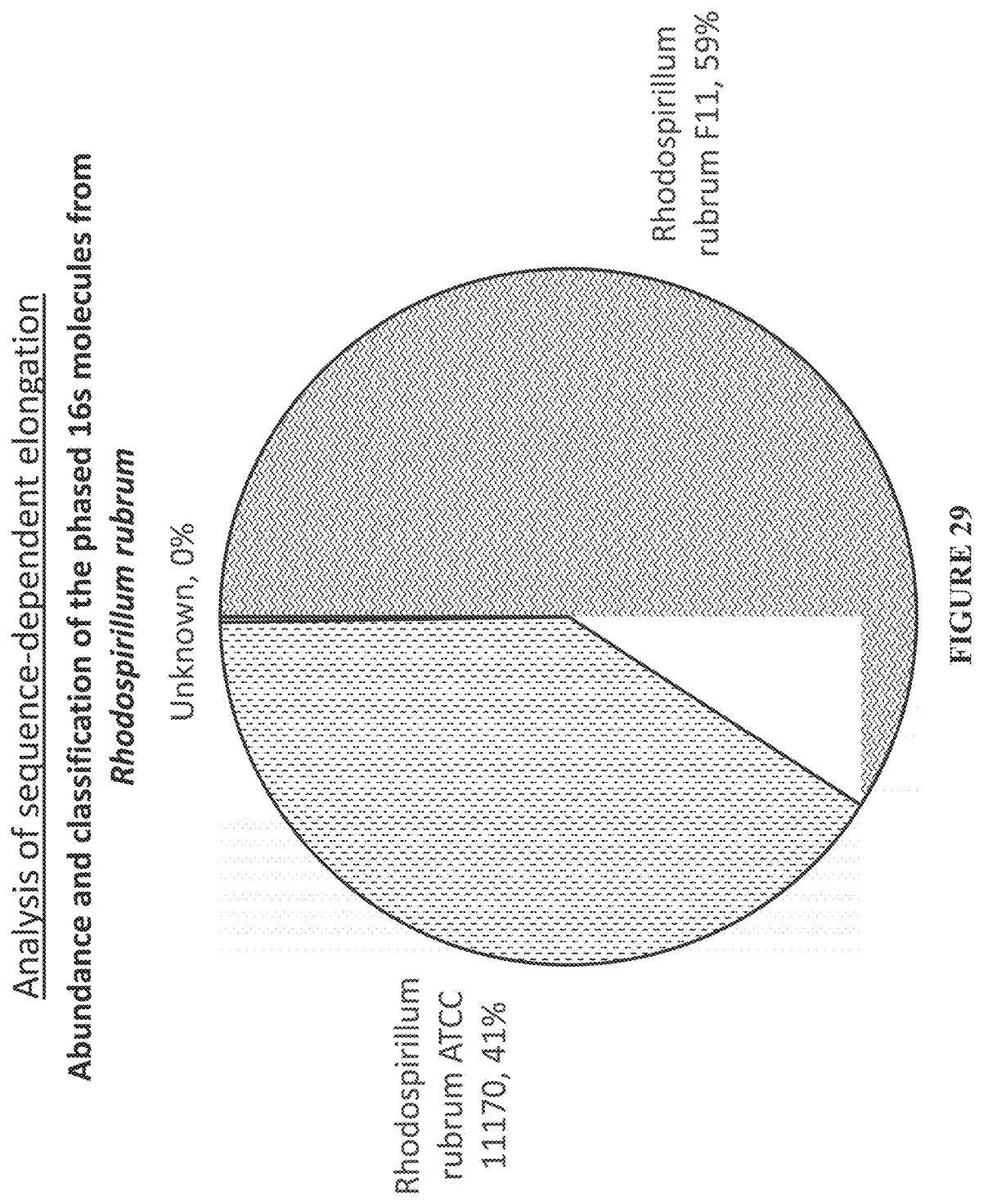

Analysis of sequence-dependent elongation

**Abundance and classification of the phased 16s molecules from *Rhodospirillum rubrum***

Unknown, 0%

Rhodospirillum rubrum F11, 59%

Rhodospirillum rubrum ATCC 11170, 41%

FIGURE 29

1 Clostridiales, 7.1%
2 Bacillales, 6.1%
3 Enterobacteriales, 5.6%
4 Pseudomonadales, 4.9%
5 Rhizobiales, 4.8%
6 Burkholderiales, 4.5%
7 Lactobacillales, 3.7%
8 Streptomycetales, 3.3%
9 Micrococcales, 3.2%
10 Bacteroidales, 2.3%
11 uncultured bacterium, 2.3%
12 Rhodobacterales, 2.1%
13 Corynebacteriales, 2.0%
14 Flavobacteriales, 1.9%
15 Oceanospirillales, 1.7%
16 Rhodospirillales, 1.6%
17 Propionibacteriales, 1.5%
18 Sphingobacteriales, 1.4%
19 Alteromonadales, 1.4%
20 Vibrionales, 1.3%
21 Sphingomonadales, 1.4%
22 Cytophagales, 1.4%
23 Campylobacterales, 1.1%
24 Aeromonadales, 0.9%
25 Halobacteriales, 0.9%
26 Acidimicrobiales, 0.8%
27 Rhodocyclales, 0.8%
28 Solibacterales, 0.8%
29 Pasteurellales, 0.8%
30 Solirubrobacterales, 0.7%
31 Blastocatellales, 0.7%
32 Thermoplasmatales, 0.7%
33 Chthoniobacterales, 0.7%
34 Planctomycetales, 0.7%
35 Rickettsiales, 0.7%
36 Pseudonocardiales, 0.6%
37 Caulobacterales, 0.6%
38 Nitrospirales, 0.6%
39 Unknown Order, 0.6%
40 Selenomonadales, 0.6%
41 Thiotrichales, 0.6%
42 Vibrionales, 1.3%
43 SubsectionIII, 0.6%
44 Anaerolineales, 0.5%
45 SC-I-84, 0.5%
46 Nitrosomonadales, 0.5%
47 Frankiales, 0.5%
48 Myxococcales, 0.5%
49 SubsectionI, 0.5%
50 Micromonosporales, 0.5%
51 SAR11 clade, 0.4%
52 Neisseriales, 0.4%
53 Caldilineales, 0.4%
54 Spirochaetales, 0.4%
55 Methanobacteriales, 0.4%
56 Chromatiales, 0.3%
57 Methylophilales, 0.3%
58 Desulfuromonadales, 0.3%
59 uncultured archaeon, 0.3%
60 Legionellales, 0.3%
61 Glycomycetales, 0.3%
62 Thermoanaerobacterales, 0.3%
63 Gaiellales, 0.3%
64 Methanosarcinales, 0.3%
65 Gammaproteobacteria Incertae Sedis, 0.3%
66 Bdellovibrionales, 0.3%
67 Desulfurellales, 0.3%
68 Deinococcales, 0.3%
69 Subgroup 7, 0.2%
70 Hydrogenophilales, 0.2%
71 uncultured marine group I thaumarchaeote, 0.2%
72 Synergistales, 0.2%
73 Fibrobacterales, 0.2%
74 Acidithiobacillales, 0.2%
75 Armatimonadales, 0.2%
76 Methylococcales, 0.2%
77 Ktedonobacterales, 0.2%
78 SubsectionIV, 0.2%
79 Sulfolobales, 0.2%
80 Verrucomicrobiales, 0.2%
81 Cellvibrionales, 0.2%
82 Streptosporangiales, 0.2%
83 Coriobacteriales, 0.2%
84 Erysipelotrichales, 0.2%
85 MBA03, 0.2%
86 uncultured organism, 0.2%
87 Strombomonas acuminata, 0.2%
88 Bifidobacteriales, 0.2%
89 uncultured Verrucomicrobia bacterium, 0.2%
90 Desulfovibrionales, 0.1%
91 MSBL9, 0.1%
92 Sva0485, 0.1%
93 Tepidisphaerales, 0.1%
94 Mycoplasmatales, 0.1%
95 Oligoflexales, 0.1%
96 Mollicutes RF9, 0.1%
97 NB1-j, 0.1%
98 Desulfurococcales, 0.1%
99 Puniceicoccales, 0.1%
100 Napoli-4B-65, 0.1%
101 Subgroup 10, 0.1%
102 Thermales, 0.1%
103 RS-F29, 0.1%
104 Cardiobacteriales, 0.1%
105 Nautiliales, 0.1%
106 MB11C04 marine group, 0.1%
107 TRA3-20, 0.1%
108 uncultured rumen bacterium, 0.1%
109 Acholeplasmatales, 0.1%
110 Sva0071, 0.1%
111 uncultured crenarchaeote, 0.1%
112 Methanopyrales, 0.1%
113 43F-1404R, 0.1%
114 Methanocellales, 0.1%
115 uncultured Micromonospora sp., 0.1%
116 Actinomycetales, 0.1%
117 Ziziphus jujuba, 0.1%
118 uncultured planctomycete, 0.1%
119 Phycisphaerales, 0.1%
120 Fusobacteriales, 0.1%
121 Kallotenuales, 0.1%
122 Terrestrial Miscellaneous Gp(TMCG), 0.1%
123 SAR324 clade(Marine group B), 0.1%
124 Rubrobacterales, 0.1%
125 NB1-n, 0.1%
126 Opitutales, 0.1%
127 Victivallales, 0.1%
128 Chlamydiales, 0.1%
129 uncultured thaumarchaeote, 0.1%
130 Gemmatimonadales, 0.1%
131 Methanomicrobiales, 0.1%
132 Pla1 lineage, 0.1%
133 Desulfarculales, 0.1%
134 Elaeis guineensis (African oil palm), 0.1%
135 Petrotogales, 0.1%
136 aaa34a10, 0.1%
137 Emcibacterales, 0.1%
138 Ardenticatenales, 0.1%
139 uncultured cyanobacterium, 0.1%
140 Thermoproteales, 0.1%
141 Acidiferrobacterales, 0.1%
142 PeM15, 0.1%
143 Syntrophobacterales, 0.1%
144 Brocadiales, 0.1%
145 uncultured soil bacterium, 0.1%
146 Anemone flaccida, 0.1%
147 uncultured phototrophic eukaryote, 0.1%
148 Sceptridium biternatum, 0.0%
149 uncultured Nocardioidaceae bacterium, 0.0%
150 Ignavibacteriales, 0.0%
151 Thermococcales, 0.0%
152 Opitutae vadinHA64, 0.0%
153 marine metagenome, 0.0%
154 SubsectionII, 0.0%
155 C0119, 0.0%
156 Iodidimonadales, 0.0%
157 Triticum aestivum (bread wheat), 0.0%
158 HTA4, 0.0%
159 Chlorobiales, 0.0%
160 Order II, 0.0%
161 Order II, 0.0%
162 uncultured candidate division TG2 bacterium, 0.0%
163 E01-9C-26 marine group, 0.0%
164 uncultured Acidobacterium sp., 0.0%
165 Kordiimonadales, 0.0%
166 Subgroup 23, 0.0%
167 Order III, 0.0%
168 GIF3, 0.0%
169 KI89A clade, 0.0%
170 Pyrus spinosa, 0.0%
171 Stellarima microtrias, 0.0%
172 Porphyridium aerugineum, 0.0%
173 Bradymonadales, 0.0%
174 Euzebyales, 0.0%
175 Methanococcales, 0.0%

FIG. 30 (Cont.)

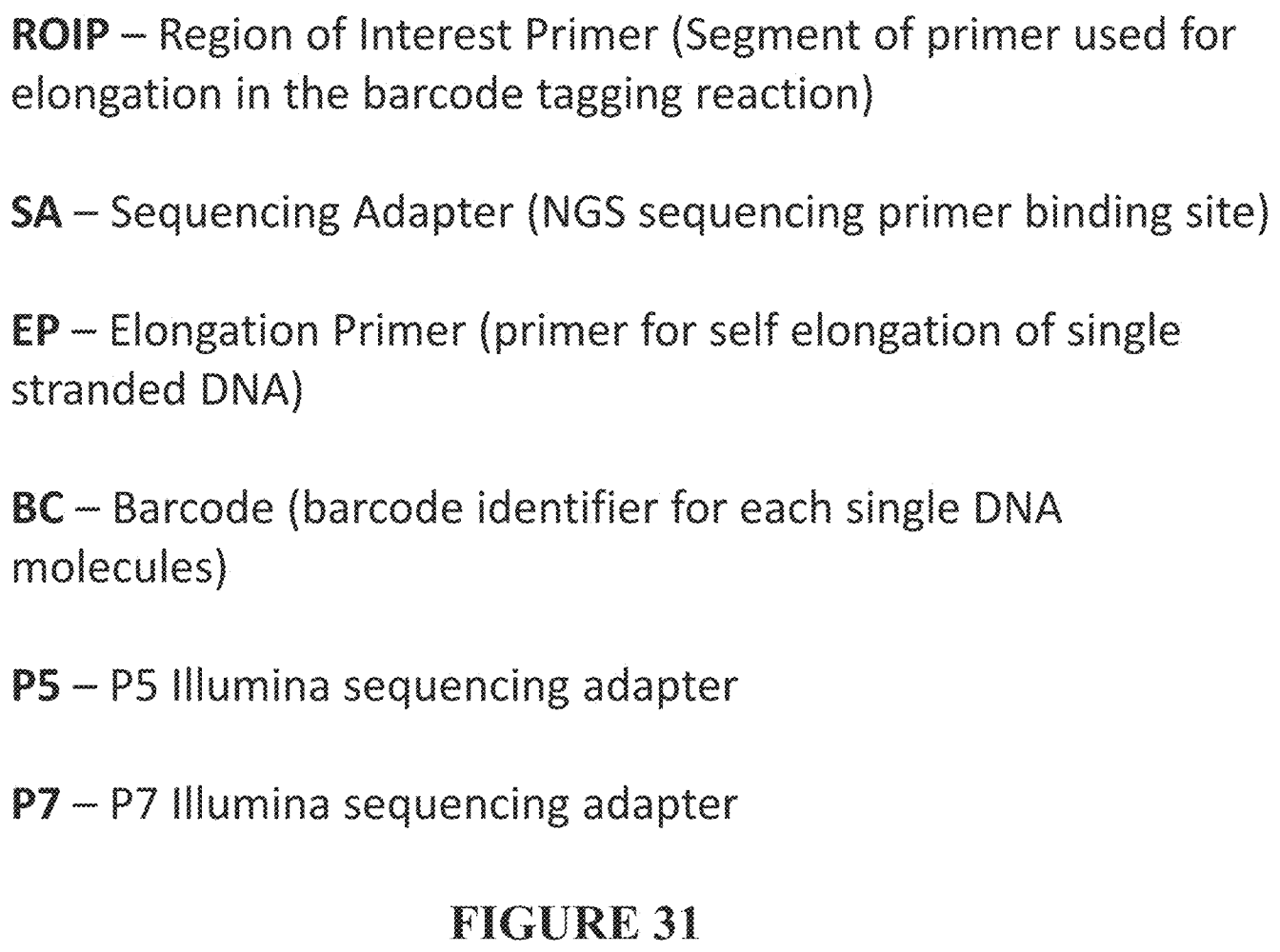

ROIP – Region of Interest Primer (Segment of primer used for elongation in the barcode tagging reaction)

SA – Sequencing Adapter (NGS sequencing primer binding site)

EP – Elongation Primer (primer for self elongation of single stranded DNA)

BC – Barcode (barcode identifier for each single DNA molecules)

P5 – P5 Illumina sequencing adapter

P7 – P7 Illumina sequencing adapter

FIGURE 31

Self elongated DNA library (multiple EP's)

Padlock Self Elongated DNA library

3'
5'
EP
SA
BC
ROIP

3'
5'
P5
SA
20
3'
5'
P7
EP
SA
BC
ROIP

FIGURE 34

SEQUENCE LISTING

```
<160> NUMBER OF SEQ ID NOS: 12

<210> SEQ ID NO 1
<211> LENGTH: 32
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 1
cctacgggrs gcagcagcag cacgtcatgc ac 32

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
agcmgccgcg gtcagcacgt catgcac 27

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
ggattagata cccbdgtagt ccagcacgtc atgcac 36

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
aaactyaaar raattgacgg cagcacgtca tgcac 35

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gcatggctgy ccagcacgtc atgcac 26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tgyacwcacc gcagcacgtc atgcac 26

<210> SEQ ID NO 7
<211> LENGTH: 28
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 7

aagtcgtaac aagcagcacg tcatgcac                                         28


<210> SEQ ID NO 8
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other

<400> SEQUENCE: 8

gtgactggag ttcagacgtg tgctcttccg atcttnanac atgcaagtcg rrcg            54


<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

gtgactggag ttcagacgtg tgctcttccg atctcaatgg rsgvrasyct ga              52


<210> SEQ ID NO 10
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

gtgactggag ttcagacgtg tgctcttccg atctaytggg ydtaaag                    47


<210> SEQ ID NO 11
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

gtgactggag ttcagacgtg tgctcttccg atctgaattg acggggrccc gca             53
```

-continued

```
<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

gtgactggag ttcagacgtg tgctcttccg atctyaacga gcgmraccc              49
```

METHODS AND COMPOSITIONS FOR PHASED SEQUENCING

CROSS-REFERENCE

This application is a continuation of U.S. application Ser. No. 16/328,663, filed Feb. 26, 2019, which is a 371 U.S. National Stage Application of International Application No. PCT/US2017/049496, filed Aug. 30, 2017, which claims the benefit of U.S. Provisional Application No. 62/381,547, filed Aug. 30, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 31, 2017, is named 50112_702_601_SL.txt and is 3,157 bytes in size.

BACKGROUND

Next Generation Sequencing (NGS) technology can allow for simultaneous, high-throughput sequencing of vast numbers of nucleic acid molecules from various sources. However, limitations in sequencing read lengths can make it difficult to determine whether genetic variations that can be read in sequencing reactions originate from the same or different nucleic acid molecules.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

SUMMARY

In some aspects, the present disclosure provides a method comprising: a) providing a sample comprising a plurality of nucleic acids, wherein said plurality of nucleic acids comprises a nucleic acid strand, wherein said nucleic acid strand comprises an adaptor comprising an elongation sequence and a molecular barcode, wherein said elongation sequence is complementary to at least a portion of a nucleic acid sequence in said nucleic acid strand; b) annealing said elongation sequence to said portion of said nucleic acid sequence in said nucleic acid strand, thereby generating a partially-duplexed nucleic acid strand, wherein said partially-duplexed nucleic acid strand comprises a 5' portion comprising a single-stranded region and a 3' portion comprising said elongation sequence in an intramolecular duplex with said portion of said nucleic acid sequence; and c) extending said elongation sequence with a polymerase using said 5' portion of said partially-duplexed nucleic acid strand as a template, thereby generating an extended nucleic acid. In some embodiments, said nucleic acid strand is in a single-stranded nucleic acid. In some embodiments, said nucleic acid strand is in a double-stranded nucleic acid. In some embodiments, a 3' end of said nucleic acid strand comprises said adaptor. In some embodiments, a 3' end of said adaptor comprises said elongation sequence. In some embodiments, said extended nucleic acid comprises a stem-loop structure comprising a hybridized region and an unhybridized region. In some embodiments, said hybridized region comprises a first strand and a second strand, wherein said first strand comprises a 5' end of said extended nucleic acid and said second strand comprises a 3' end of said extended nucleic acid. In some embodiments, a 5' end of said second strand comprises said elongation sequence. In some embodiments, said unhybridized region is 3' to said first strand. In some embodiments, a 3' end of said unhybridized region comprises said molecular barcode. In some embodiments, said nucleic acid strand comprises DNA. In some embodiments, said nucleic acid strand comprises cDNA. In some embodiments, said nucleic acid strand comprises genomic DNA. In some embodiments, said nucleic acid strand comprising said adaptor is generated from genomic DNA. In some embodiments, said nucleic acid strand comprising said adaptor is generated from a cell-free nucleic acid. In some embodiments, said nucleic acid strand comprising said adaptor is generated from a nucleic acid from a cell. In some embodiments, said nucleic acid strand comprising said adaptor is generated from a nucleic acid from a biological sample. In some embodiments, said nucleic acid strand comprising said adaptor is generated from a nucleic acid from a cell-free sample. In some embodiments, said nucleic acid strand is generated from RNA. In some embodiments, the method further comprises reverse transcribing said RNA before step a). In some embodiments, the method further comprises appending said adaptor to a nucleic acid molecule to generate said nucleic acid strand comprising said adaptor. In some embodiments, said appending is performed by ligation. In some embodiments, said appending is performed by polymerase chain reaction (PCR). In some embodiments, said PCR is performed with an oligonucleotide comprising a sequence complementary to said first adaptor. In some embodiments, said oligonucleotide further comprises a sequence complementary to at least a portion of a template nucleic acid. In some embodiments, a 3' end of said oligonucleotide comprises said sequence complementary to said at least a portion of said template nucleic acid. In some embodiments, said sequence complementary to said at least a portion of said template nucleic acid comprises a random sequence. In some embodiments, said sequence complementary to said at least a portion of said template nucleic acid comprises complete complementary to said portion of said template nucleic acid. In some embodiments, the method further comprises purifying said nucleic acid strand comprising said first adaptor after said appending. In some embodiments, said purifying comprises removing one or more unappended adaptors prior to step a. In some embodiments, said purifying comprises enzymatic digestion of said one or more unappended adaptors. In some embodiments, said enzymatic digestion comprises use of an exonuclease. In some embodiments, said one or more unappended adaptors comprise uracil, wherein said removing of said one or more unappended adaptors comprises use of a uracil-DNA glycosylase, an endonuclease, or both. In some embodiments, said purifying comprises use of solid phase reversible immobilization to remove said one or more unappended adaptors. In some embodiments, said purifying comprises use of column-based solid phase extraction to remove said one or more unappended adaptors. In some embodiments, said purifying comprises use of gel filtration. In some embodiments, the method further comprises amplifying said nucleic acid strand comprising said adaptor prior to step a). In some embodiments, the method further comprises denaturing a double-stranded DNA molecule comprising said first adaptor prior to step a), thereby generating a single-stranded nucleic acid comprising said nucleic acid strand comprising said first adaptor. In some embodiments, said denaturing comprises use of an enzyme to degrade a strand of said double-stranded DNA molecules. In some embodiments, said enzyme is an exonuclease. In some embodiments, said exonuclease is a lambda exonuclease. In some embodiments, said denaturing comprises: biotinylating a strand of said double-stranded DNA molecule to generate a biotinylated double-stranded DNA molecule; binding said biotinylated double-stranded DNA molecule to a streptavidin-coated surface; and washing said surface to release a non-biotinylated DNA strand, thereby denaturing said double-stranded DNA molecule. In some embodiments, said denaturing comprises heating said double-stranded DNA molecule. In some embodiments, said denaturing comprises alkaline denaturation. In some embodiments, said elongation sequence comprises a random sequence. In some embodiments, said elongation sequence is substantially or completely complementary to said portion of said nucleic acid sequence. In some embodiments, said molecular barcode comprises a random or semi-random sequence. In some embodiments, said plurality of nucleic acids in said sample comprises a first adaptor comprising a unique molecular barcode. In some embodiments, said first adaptor in said plurality of nucleic acids further comprises a second barcode common to each of said plurality of single-stranded nucleic acids. In some embodiments, a 3' extended portion generated by said extending in said extended nucleic acid comprises a length of about 100 bases to about 400 bases. In some embodiments, a 3' extended portion generated by said extending in said extended nucleic acid comprises a length of about 400 bases to about 500 bases. In some embodiments, the method further comprises appending an additional adaptor to said extended nucleic acid. In some embodiments, said appending is performed by ligating. In some embodiments, said appending is performed by polymerase chain reaction. In some embodiments, said polymerase chain reaction comprises use of one or more oligonucleotides comprising a 5' portion comprising said additional adaptor and a 3' portion comprising a sequence complementary to a 3' extended portion generated by said extending in said extended nucleic acid. In some embodiments, said additional adaptor is appended at a 3' end of said extended nucleic acid. In some embodiments, the method further comprises amplifying said extended nucleic acid appended to said additional adaptor. In some embodiments, said amplifying is performed with a first primer and a second primer, wherein said first primer anneals to said first adaptor or a complement thereof, and wherein said second primer anneals to said second adaptor or a complement thereof. In some embodiments, the method further comprises sequencing products of said amplifying to generate sequencing reads. In some embodiments, said sequencing comprises massively parallel sequencing. In some embodiments, the method further comprises phasing said sequencing reads to determine a molecular origin of two or more nucleic acid sequences of interest in said plurality of nucleic acids. In some embodiments, the method further comprises annealing a padlock probe to said extended nucleic acid, wherein said padlock probe comprises a 5' end and a 3'-end connected by a linker sequence. In some embodiments, the method further comprises extending said 3' end of said padlock probe to generate an extended nucleic acid comprising said padlock probe and sequence complementary to said portion of said nucleic acid sequence. In some embodiments, the method further comprises ligating a 5' end and a 3' end of said extended nucleic acid comprising said padlock probe and said sequence complementary to said portion of said nucleic acid sequence, thereby generating a circularized nucleic acid comprising said padlock probe and said sequence complementary to said portion of said nucleic acid sequence. In some embodiments, the method further comprises amplifying said circularized nucleic acid, thereby generating linearized nucleic acids comprising said molecular barcode and a sequence complementary to a sequencing primer. In some embodiments, said amplifying is performed by PCR. In some embodiments, the method further comprises sequencing said linearized nucleic acids to generate sequencing reads. In some embodiments, said sequencing comprises massively parallel sequencing. In some embodiments, the method further comprises phasing said sequencing reads to determine a molecular origin of two or more nucleic acid sequences of interest in said plurality of nucleic acids.

In some aspects, the present disclosure provides a stem-loop nucleic acid comprising: a hybridized region comprising a first strand and a second strand, wherein said first strand comprises a 5' end of said stem-loop nucleic acid, wherein said second strand comprises a 3' end of said stem-loop nucleic acid, wherein a 5' portion of said hybridized region of said second strand comprises a first portion of an adaptor, which first portion is hybridized to a 3' portion of said hybridized region of said first strand; and an unhybridized region 3' to said hybridized region of said first strand, wherein said unhybridized region comprises a 3' portion comprising a second portion of said adaptor, wherein said second portion comprises a barcode. In some embodiments, said stem-loop nucleic acid comprises DNA. In some embodiments, said stem-loop nucleic acid comprises cDNA. In some embodiments, said stem-loop nucleic acid is generated from RNA by reverse transcription. In some embodiments, said stem-loop nucleic acid comprises genomic DNA. In some embodiments, said stem-loop nucleic acid is generated from genomic DNA. In some embodiments, said stem-loop nucleic acid is generated from a cell-free nucleic acid. In some embodiments, said stem-loop nucleic acid is generated from a nucleic acid from a cell. In some embodiments, said stem-loop nucleic acid is generated from a nucleic acid from a biological sample. In some embodiments, said stem-loop nucleic acid is generated from a nucleic acid from a cell-free sample. In some embodiments, said barcode comprises a random sequence. In some embodiments, said hybridized region has a length of from about 100 base pairs to about 500 base pairs. In some embodiments, said hybridized region has a length of from about 400 base pairs to about 500 base pairs.

In some aspects, the present disclosure provides a stem-loop nucleic acid comprising: a hybridized region comprising a first strand and a second strand, wherein said first strand comprises a 5' end of said stem-loop nucleic acid, wherein said second strand comprises a 3' end of said stem-loop nucleic acid, wherein a 5' end of said second strand comprises a first portion of an adaptor that is hybridized to a 3' end of said first strand; and an unhybridized region 3' to said first strand, wherein said unhybridized region comprises a 3' end comprising a second portion of said adaptor, wherein said second portion comprises a barcode. In some embodiments, said stem-loop nucleic acid comprises DNA. In some embodiments, said stem-loop nucleic acid comprises cDNA. In some embodiments, said stem-loop nucleic acid is generated from RNA by reverse transcription. In some embodiments, said stem-loop nucleic acid comprises genomic DNA. In some embodiments, said stem-loop nucleic acid is generated from genomic DNA. In some embodiments, said stem-loop nucleic acid is generated from a cell-free nucleic acid. In some embodiments, said stem-loop nucleic acid is generated from a nucleic acid from a cell. In some embodiments, said stem-loop nucleic acid is generated from a nucleic acid from a biological sample. In some embodiments, said stem-loop nucleic acid is generated from a nucleic acid from a cell-free sample. In some embodiments, said barcode comprises a random sequence. In some embodiments, said hybridized region has a length of from about 100 base pairs to about 500 base pairs. In some embodiments, said hybridized region has a length of from about 400 base pairs to about 500 base pairs.

In some aspects, the present disclosure provides a stem-loop nucleic acid comprising: a hybridized region comprising a first strand and a second strand, wherein said first strand comprises a 5' portion of said stem-loop nucleic acid, wherein said second strand comprises a 3' portion of said stem-loop nucleic acid, wherein a 5' end of said second strand comprises a first portion of an adaptor that is hybridized to a 3' end of said first strand; and an unhybridized region 3' to said first strand, wherein said unhybridized region comprises a 3' portion comprising a second portion of said adaptor, wherein said second portion comprises a barcode. In some embodiments, said stem-loop nucleic acid comprises DNA. In some embodiments, said stem-loop nucleic acid comprises cDNA. In some embodiments, said stem-loop nucleic acid is generated from RNA by reverse transcription. In some embodiments, said stem-loop nucleic acid comprises genomic DNA. In some embodiments, said stem-loop nucleic acid is generated from genomic DNA. In some embodiments, said stem-loop nucleic acid is generated from a cell-free nucleic acid. In some embodiments, said stem-loop nucleic acid is generated from a nucleic acid from a cell. In some embodiments, said stem-loop nucleic acid is generated from a nucleic acid from a biological sample. In some embodiments, said stem-loop nucleic acid is generated from a nucleic acid from a cell-free sample. In some embodiments, said barcode comprises a random sequence. In some embodiments, said hybridized region has a length of from about 100 base pairs to about 500 base pairs. In some embodiments, said hybridized region has a length of from about 400 base pairs to about 500 base pairs.

In some aspects, the present disclosure provides a nucleic acid strand comprising an adaptor at a 3' end, wherein said adaptor comprises a barcode and an elongation sequence, wherein said elongation sequence is configured to hybridize to a portion of said nucleic acid strand, wherein said elongation sequence is configured to permit a polymerizing enzyme to conduct an extension reaction to generate at least a portion of a strand complementary to said nucleic acid strand. In some embodiments, said nucleic acid strand comprises DNA. In some embodiments, said nucleic acid strand comprises cDNA. In some embodiments, said nucleic acid strand is generated from RNA by reverse transcribing. In some embodiments, said nucleic acid strand comprises genomic DNA. In some embodiments, said nucleic acid strand is generated from genomic DNA. In some embodiments, said nucleic acid strand is generated from a cell-free nucleic acid. In some embodiments, said nucleic acid strand is generated from a nucleic acid from a cell. In some embodiments, said nucleic acid strand is generated from a nucleic acid from a biological sample. In some embodiments, said nucleic acid strand is generated from a nucleic acid from a cell-free sample. In some embodiments, said barcode comprises a random sequence. In some embodiments, a 3' end of said adaptor comprises said elongation sequence. In some embodiments, said elongation sequence comprises a random sequence. In some embodiments, said elongation sequence comprises a sequence complementary to said portion of said nucleic acid strand. In some embodiments, said nucleic acid strand is in a single-stranded nucleic acid. In some embodiments, said nucleic acid strand is generated from a double-stranded DNA molecule comprising said adaptor.

In some aspects, the present disclosure provides an oligonucleotide, comprising: a barcode; and an elongation sequence, wherein said elongation sequence or a complement thereof is configured to intramolecularly anneal to a first region of a nucleic acid strand upon appending said oligonucleotide to said nucleic acid strand. In some embodiments, a reverse complement of said elongation sequence is configured to intramolecularly anneal to said first region of said nucleic acid strand upon appending said oligonucleotide to said nucleic acid strand. In some embodiments, said elongation sequence is at a 5' end of said oligonucleotide. In some embodiments, said oligonucleotide further comprises a sequence complementary to at least a portion of a second region of said nucleic acid strand. In some embodiments, said sequence complementary to said at least a portion of said second region is at a 3' end of said oligonucleotide. In some embodiments, said appending comprises polymerase chain reaction. In some embodiments, said appending comprises ligation. In some embodiments, said barcode comprises a random sequence. In some embodiments, said elongation sequence comprises a random sequence. In some embodiments, said elongation sequence comprises a sequence complementary to said first region of said nucleic acid strands. In some embodiments, elongation sequence is configured to permit a polymerizing enzyme to conduct an extension reaction to generate at least a portion of a strand complementary to said nucleic acid strand.

In some aspects, the present disclosure provides a kit comprising an oligonucleotide of the disclosure. In some embodiments, a kit further comprises instructions for use.

In some aspects, the present disclosure provides a method comprising: a) appending a first adaptor to a nucleic acid in a plurality of nucleic acids, thereby generating a barcoded nucleic acid comprising said first adaptor, wherein said first adaptor comprises a molecular barcode, wherein said nucleic acid comprises a first target region and a second target region; b) amplifying said barcoded nucleic acid, thereby generating amplified barcoded nucleic acids; c) appending an elongation sequence to a barcoded nucleic acid in said amplified barcoded nucleic acids, thereby generating a barcoded nucleic acid comprising said elongation sequence, wherein said elongation sequence is complementary to at least a portion of a nucleic acid sequence in a strand of said barcoded nucleic acid, wherein said strand comprises said elongation sequence and said first adaptor; d) annealing said elongation sequence to said portion of said sequence in said strand of said barcoded nucleic acid, thereby generating a partially-duplex nucleic acid, wherein said partially-duplex nucleic acid comprises a 5' portion comprising a single-stranded region and a 3' portion comprising said elongation sequence in an intramolecular duplex with said portion of said nucleic acid sequence; e) extending said elongation sequence with a polymerase using said 5' portion of said partially-duplex nucleic acid strand as a template, thereby generating an extended nucleic acid; f) appending a second adaptor to said extended nucleic acid, thereby generating an extended nucleic acid comprising said first adaptor and said second adaptor, wherein said second adaptor comprises a sequence complementary to a sequencing primer; and g) amplifying said extended nucleic acid comprising said first adaptor and said second adaptor with a first primer and a second primer, wherein said first primer anneals to said first adaptor or a complement thereof, and wherein said second primer anneals to said second adaptor or a complement thereof. In some embodiments, the method further comprises sequencing a product of said amplifying to generate sequencing reads. In some embodiments, the method further comprises phasing said sequencing reads to determine a molecular origin of said first target region and said second target region. In some embodiments, the method further comprises appending a first adaptor comprising a barcode to two or more of said plurality of nucleic acids, thereby generating a plurality of nucleic acids appended to said first adaptor, wherein said barcode in each of said plurality of nucleic acids appended to said first adaptor is unique. In some embodiments, said appending of said elongation sequence is performed by PCR. In some embodiments, said PCR comprises use of an oligonucleotide comprising a complement of said elongation sequence. In some embodiments, said appending of said first adaptor is performed by PCR. In some embodiments, said PCR comprises use of an oligonucleotide comprising a complement of said first adaptor and a sequence complementary to at least a portion of a nucleic acid sequence in said nucleic acid. In some embodiments, said elongation sequence is at a 3' end of said barcoded nucleic acid comprising said elongation sequence. In some embodiments, said nucleic acid comprises genomic DNA, cDNA, or RNA. In some embodiments, said nucleic acid is generated from genomic DNA or RNA. In some embodiments, said first target region and said second target region are about 200 bases to about 25,000 bases apart in said nucleic acid. In some embodiments, said first target region and said second target region are about 500 bases to about 20,000 bases apart in said nucleic acid. In some embodiments, said first target region and said second target region are about 1000 bases to about 15,000 bases apart in said nucleic acid. In some embodiments, said first target region, said second target region, or both comprise a single nucleotide change relative to a wild type sequence. In some embodiments, said first target region and said second target region comprise regions of an exome separated by an intron. In some embodiments, said first target region, said second target region or both comprise a single nucleotide polymorphism, a copy number variation, or a sequence rearrangement event in genomic DNA or RNA. In some embodiments, the method further comprises purifying said barcoded nucleic acid comprising said first adaptor before step c). In some embodiments, said purifying comprises removing one or more unappended first adaptors. In some embodiments, said purifying comprises enzymatic digestion of said one or more unappended first adaptors. In some embodiments, said enzymatic digestion comprises use of an exonuclease. In some embodiments, said first adaptor comprises uracil, wherein said removing of said one or more unappended first adaptors comprises use of a uracil-DNA glycosylase, an endonuclease, or both. In some embodiments, said purifying comprises use of solid phase reversible immobilization to remove said one or more unappended first adaptors. In some embodiments, said purifying comprises use of column-based solid phase extraction to remove said one or more unappended first adaptors. In some embodiments, said purifying comprises use of gel filtration.

In some aspects, the present disclosure provides a method comprising: a) appending a barcode to a parent nucleic acid from a plurality of parent polynucleotides, wherein said parent nucleic acid comprises a first target region and a second target region, thereby generating a barcoded nucleic acid; b) generating a first nucleic acid molecule and a second nucleic acid molecule from said barcoded nucleic acid, wherein said first nucleic acid molecule and said second nucleic acid molecule are shorter in length than said parent nucleic acid, wherein said first nucleic acid molecule comprises said barcode and said first target region but not said second target region, wherein said second nucleic acid molecule comprises said barcode and said second target region but not said first target region; c) sequencing said first nucleic acid molecule and said second nucleic acid molecule to obtain sequencing reads; and d) phasing said sequencing reads to determine a molecular origin of said first target region and said second target region; wherein sequencing coverage for said phasing is reduced by at least about 10-fold relative to sequencing the parent nucleic acid directly in the absence of step c). In some embodiments, sequencing coverage for said phasing is reduced by at least about 20-fold relative to sequencing the parent nucleic acid in the absence of step c). In some embodiments, sequencing coverage for said phasing is reduced by at least about 30-fold relative to sequencing the parent nucleic acid in the absence of step c). In some embodiments, sequencing coverage for said phasing is reduced by at least about 40-fold relative to sequencing the parent nucleic acid in the absence of step c). In some embodiments, the method further comprises appending one or more elongation sequences to said barcoded nucleic acid prior to step c), wherein said one or more elongation sequences comprise a sequence complementary to at least a portion of a strand of said barcoded nucleic acid, wherein said strand comprises said barcode.

In some embodiments, a method of the disclosure comprises multiplexing one or more steps of the method.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 12 shows an illustrative scheme to generate a single-stranded nucleic acid from a double-stranded nucleic acid when the PCR primer segment is not at the 5' terminus and has not been removed.

FIG. 15 illustrates an option in which the intramolecular elongation of single-stranded nucleic acid can be limited to NGS read length.

FIG. 16 illustrates impact of polymerase and randomer length on coverage evenness of the tagged long nucleic acid molecules.

FIG. 17 illustrates the impact of polymerase and randomer length on the completeness of the sequence coverage of the tagged nucleic acid molecules.

FIG. 23 shows an illustrative scheme for generating a NGS library via a sequence-dependent method that can comprise use of sequence-specific PCR amplification to add a second sequencing adaptor.

FIG. 29 illustrates the abundance and classification of the phased tagged 16s molecules that originate from *Rhodospirillum rubrum.*

FIG. 31 illustrates the abbreviations used in FIGS. 32-35.

FIG. 34 shows an illustrative scheme for appending a padlock probe A padlock probe can have one arm complementary to the Region of Interest Primer (ROIP) segment and the other arm complementary to a segment within the self-elongated nucleic acid molecule.

DETAILED DESCRIPTION

Figure 1:
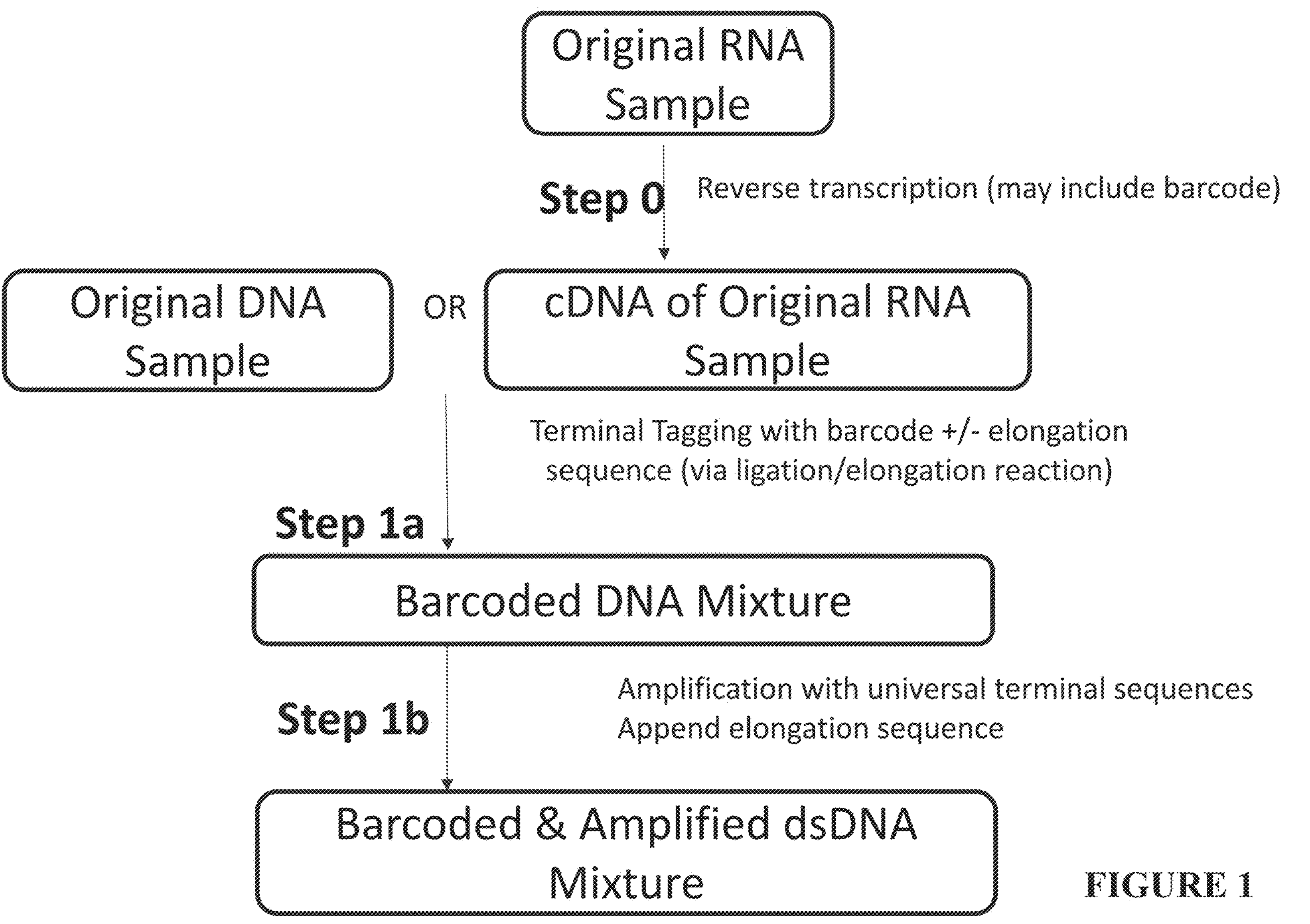
FIG. 1 depicts an illustrative scheme for tagging and amplifying nucleic acid molecules.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

Unless described otherwise, all technical and scientific terms used herein have a meaning as is commonly understood by one of ordinary skill in the art to which the various embodiments described herein belongs.

As used herein and in the specification appended claims, the singular forms “a”, “an”, and “the” include the plural referents unless the context clearly dictates otherwise. Thus, for example, a reference to “a DNA molecule” is a reference to one or more DNA molecules and equivalents thereof, a "polynucleotide" includes a single polynucleotide as well as two or more of the same or different polynucleotides, and reference to a "nucleic acid" includes a single nucleic acid as well as two or more of the same or different nucleic acids.

As used herein, the term "about" or "approximately" can mean within an acceptable error range for the particular value as determined by one of ordinary skill in the art, which will depend in part on how the value is measured or determined, e.g., the limitations of the measurement system. For example, "about" can mean within 1, 1.5, 2, 2.5, 3, or more standard deviations. Alternatively, "about" can mean a range of up to 20%, up to 10%, up to 5%, or up to 1% of a given value. Particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value can be assumed.

As used herein, the term "adjacent" can refer to two nucleotide sequences in a nucleic acid separated by 0 to about 20 nucleotides, more specifically, in a range of about 1 to about 10 nucleotides, or sequences that directly abut one another.

As used herein, the term "amplification" can encompass any manner by which at least a part of one or more target nucleic acid is reproduced, for example in a template-dependent manner. A broad range of techniques can be used to amplify nucleic acid sequences, either linearly or exponentially. Illustrative methods for performing amplification include ligase chain reaction (LCR), ligase detection reaction (LDR), ligation followed by Q-replicase amplification, polymerase chain reaction (PCR), primer extension, strand displacement amplification (SDA), hyperbranched strand displacement amplification, multiple displacement amplification (MDA), nucleic acid strand-based amplification (NASBA), two-step multiplexed amplification, and rolling circle amplification (RCA), including multiplex versions and combinations thereof. Examples of multiplex versions and combinations of amplification procedures include, but are not limited to, oligonucleotide ligation assay (OLA)/PCR, PCR/OLA, LDR/PCR, PCR/PCR/LDR, PCR/LDR, LCR/PCR, and PCR/LCR (also known as combined chain reaction (CCR)), and the like.

As used herein, the term "clustering" can refer to the comparison of two or more nucleotide sequences based on the presence of short or long stretches of identical or similar nucleotides. Clustering is also referred to using the terms "assembly" or "alignment".

As used herein, the term "covers" can mean that an overlapping group of polynucleotide sequences can be assembled into a contiguous consensus sequence that can span and accurately represent the complete sequence of the parental long nucleic acid molecule being sequenced.

As used herein, the term "coverage-bias" can refer to a non-random distribution of sequence reads covering a longer parental sequence. Lack of even coverage or representation of the parental sequence can occur due to non-random fragmentation and/or site-preferential restriction enzyme digestion. Other bias-inducing methods include intermolecular ligation, which can be limited due to length constraints in the double-stranded DNA (dsDNA) molecule being circularized. Barcode pairing can improve assembly lengths. Reads associated with two distinct barcodes can be aligned to the reference genome. Individually, each group of reads assembles into a contiguous sequence ("contig") that can be several kilobases in length. Barcode pairing merges the groups, increasing and smoothing coverage across the region to allow assembly of the full 10-kb target sequence. Length histograms of the contigs assembled from genomic reads (minimum length of about 1000 base pairs (bp)) from the reference genome and the sample can be compared.

As used herein, the term "distributing or proximizing the barcode to different parts of the sequence" can refer to a process or reaction in which a barcode is made proximal (near or adjacent) to a different part of the same nucleic acid molecule it resides on. The barcode can be made proximal through a polymerase-based primed nucleic acid elongation reaction that is facilitated by a nucleic acid priming sequence adjacent to the barcode. The polymerase priming sequence can be a randomer (e.g. 6-20 random bases). There can be many copies of a molecule with a unique single barcode, but each copy may have a different random self-elongation sequence. Therefore, the random priming can collectively translocate, distribute, or proximize the nucleic acid barcode, which can be near or adjacent to the random self-elongation sequence, to all parts of a nucleic acid molecule in an even manner. The copied sequences arising from the random priming events on the same parental long nucleic acid molecule can share the same molecule-specific barcodes.

The polymerase priming sequence can be a randomer having a length of, for example, 6 random bases to 25 random bases. The polymerase priming sequence can be a randomer having a length of, for example, at least 6 random bases. The polymerase priming sequence can be a randomer having a length of, for example, at most 25 random bases. The polymerase priming sequence can be a randomer having a length of, for example, 6 random bases to 8 random bases, 6 random bases to 10 random bases, 6 random bases to 11 random bases, 6 random bases to 12 random bases, 6 random bases to 13 random bases, 6 random bases to 14 random bases, 6 random bases to 15 random bases, 6 random bases to 16 random bases, 6 random bases to 18 random bases, 6 random bases to 20 random bases, 6 random bases to 25 random bases, 8 random bases to 10 random bases, 8 random bases to 11 random bases, 8 random bases to 12 random bases, 8 random bases to 13 random bases, 8 random bases to 14 random bases, 8 random bases to 15 random bases, 8 random bases to 16 random bases, 8 random bases to 18 random bases, 8 random bases to 20 random bases, 8 random bases to 25 random bases, 10 random bases to 11 random bases, 10 random bases to 12 random bases, 10 random bases to 13 random bases, 10 random bases to 14 random bases, 10 random bases to 15 random bases, 10 random bases to 16 random bases, 10 random bases to 18 random bases, 10 random bases to 20 random bases, 10 random bases to 25 random bases, 11 random bases to 12 random bases, 11 random bases to 13 random bases, 11 random bases to 14 random bases, 11 random bases to 15 random bases, 11 random bases to 16 random bases, 11 random bases to 18 random bases, 11 random bases to 20 random bases, 11 random bases to 25 random bases, 12 random bases to 13 random bases, 12 random bases to 14 random bases, 12 random bases to 15 random bases, 12 random bases to 16 random bases, 12 random bases to 18 random bases, 12 random bases to 20 random bases, 12 random bases to 25 random bases, 13 random bases to 14 random bases, 13 random bases to 15 random bases, 13 random bases to 16 random bases, 13 random bases to 18 random bases, 13 random bases to 20 random bases, 13 random bases to 25 random bases, 14 random bases to 15 random bases, 14 random bases to 16 random bases, 14 random bases to 18 random bases, 14 random bases to 20 random bases, 14 random bases to 25 random bases, 15 random bases to 16 random bases, 15 random bases to 18 random bases, 15 random bases to 20 random bases, 15 random bases to 25 random bases, 16 random bases to 18 random bases, 16 random bases to 20 random bases, 16 random bases to 25 random bases, 18 random bases to 20 random bases, 18 random bases to 25 random bases, or 20 random bases to 25 random bases. The polymerase priming sequence can be a randomer having a length of, for example, 6 random bases, 8 random bases, 10 random bases, 11 random bases, 12 random bases, 13 random bases, 14 random bases, 15 random bases, 16 random bases, 18 random bases, 20 random bases, or 25 random bases.

As used herein, the term "elongation-primed single-stranded nucleic acid or ssDNA" can refer to single-stranded nucleic acid or ssDNA molecules with 3' termini that can function as priming sequences for polymerase-driven DNA polymerization of single-stranded nucleic acid or ssDNA molecules.

As used herein, the term "enrichment PCR" can refer to PCR primer extension that can occur after intramolecular elongation of a nucleotide.

As used herein, the terms "ligation adaptors" and "adaptors" can refer to short nucleic acid (e.g., dsDNA) molecules with a length of e.g. about 10 to about 30 bp. An adaptor can be appended to a nucleic acid molecule by ligation. An adaptor can be appended to a nucleic acid molecule by polymerase chain reaction. Adaptors can be composed of two synthetic oligonucleotides, which have nucleotide sequences that can be partially or completely complementary to each other. When mixing the two synthetic oligonucleotides in solution under appropriate conditions, the two synthetic oligonucleotides can anneal to each other to form a double-stranded structure. After annealing, one end of the adaptor molecule is designed to be compatible with the end of a nucleic acid fragment and can be ligated thereto. The other end of the adaptor can be designed so that it cannot be ligated, but this may not be the case (i.e., double ligated adaptors). Adaptors can contain other functional features, such as identifiers, recognition sequences for restriction enzymes, and primer binding sections. When containing other functional features, the length of the adaptors may increase; the length of the adaptors can be controlled and minimized by combining functional features.

An adaptor can have a length of, for example, 8 base pairs to 40 base pairs. An adaptor can have a length of, for example, at least 8 base pairs. An adaptor can have a length of, for example, at most 40 base pairs. An adaptor can have a length of, for example, 8 base pairs to 10 base pairs, 8 base pairs to 15 base pairs, 8 base pairs to 20 base pairs, 8 base pairs to 25 base pairs, 8 base pairs to 30 base pairs, 8 base pairs to 35 base pairs, 8 base pairs to 40 base pairs, 10 base pairs to 15 base pairs, 10 base pairs to 20 base pairs, 10 base pairs to 25 base pairs, 10 base pairs to 30 base pairs, 10 base pairs to 35 base pairs, 10 base pairs to 40 base pairs, 15 base pairs to 20 base pairs, 15 base pairs to 25 base pairs, 15 base pairs to 30 base pairs, 15 base pairs to 35 base pairs, 15 base pairs to 40 base pairs, 20 base pairs to 25 base pairs, 20 base pairs to 30 base pairs, 20 base pairs to 35 base pairs, 20 base pairs to 40 base pairs, 25 base pairs to 30 base pairs, 25 base pairs to 35 base pairs, 25 base pairs to 40 base pairs, 30 base pairs to 35 base pairs, 30 base pairs to 40 base pairs, or 35 base pairs to 40 base pairs. An adaptor can have a length of, for example, 8 base pairs, 10 base pairs, 15 base pairs, 20 base pairs, 25 base pairs, 30 base pairs, 35 base pairs, or 40 base pairs.

The term "nucleic acid" can include any form of DNA or RNA, including, for example, genomic DNA; complementary DNA (cDNA), which can be obtained from messenger RNA (mRNA) by reverse transcription or by amplification; DNA molecules produced synthetically or by amplification; cell-free DNA; cell free RNA; mRNA, tRNA and rRNA. Nucleic acid(s) can be derived from chemical synthesis (e.g., solid phase-mediated chemical synthesis), from a biological source (e.g., isolation from any organism), or from processes that involve the manipulation of nucleic acids using molecular biology tools (e.g., cloning, DNA replication, PCR amplification, reverse transcription, or any combination thereof). In some aspects, a nucleic acid can be DNA.

As used herein, the terms "nucleotide tag", "molecular tag", and "barcode tag" can refer to a combination of nucleotide sequences (e.g., unique nucleotide sequences) that can be added to a target nucleotide sequence and serve as a tag. A portion, the entire length, or none of the nucleotide combination that serves as a tag can be a predetermined sequence, or determined empirically during sequence data analysis. The molecular tag can include a specific and/or unique nucleotide sequence that encodes information about the amplicon produced when the barcode primer is employed in an amplification reaction. For example, a different tag can be employed to one or more target sequence from each of a number of different samples, such that the barcode nucleotide sequence indicates the sample origin of the resulting amplicons. The molecular tag can also include a shared or universal sequence, which allows for the simultaneous amplification of differently tagged molecules. For example, P5 and P7 Illumina universal primers may be employed. In some embodiments, the sequence of a molecular tag is random. In some embodiments, the sequence of a molecular tag is semi-random.

As used herein, the term "oligonucleotide" can refer to a nucleic acid with a length, for example, shorter than about 1,000 nucleotides, shorter than about 900 nucleotides, shorter than about 800 nucleotides, shorter than about 700 nucleotides, shorter than about 600 nucleotides, shorter than about 500 nucleotides, shorter than about 400 nucleotides, shorter than about 300 nucleotides, shorter than about 200 nucleotides, shorter than about 100 nucleotides, shorter than about 50 nucleotides, 50 nucleotides to 200 nucleotides, at least 50 nucleotides, at most 200 nucleotides, 50 nucleotides to 100 nucleotides, 50 nucleotides to 150 nucleotides, 50 nucleotides to 200 nucleotides, 100 nucleotides to 150 nucleotides, 100 nucleotides to 200 nucleotides, 150 nucleotides to 200 nucleotides, 50 nucleotides, 100 nucleotides, 150 nucleotides, or 200 nucleotides.

As used herein, the term "paired end sequencing" can refer to a method based on high throughput sequencing that generates sequencing data from both ends of a nucleic acid molecule.

As used herein, the term "padlock probe" can refer to molecules that probe long barcoded nucleic acid molecules in an NGS sample preparation method. Padlock probes can be evenly distributed along the length of the barcoded long nucleic acid molecules. In some embodiments, padlock probes can be approximately one read length (e.g. 100 bp-400 bp) apart.

A padlock probe can have a length of, for example, 50 base pairs to 500 base pairs. A padlock probe can have a length of, for example, at least 50 base pairs. A padlock probe can have a length of, for example, at most 500 base pairs. A padlock probe can have a length of, for example, 50 base pairs to 100 base pairs, 50 base pairs to 150 base pairs, 50 base pairs to 200 base pairs, 50 base pairs to 250 base pairs, 50 base pairs to 300 base pairs, 50 base pairs to 350 base pairs, 50 base pairs to 400 base pairs, 50 base pairs to 450 base pairs, 50 base pairs to 500 base pairs, 100 base pairs to 150 base pairs, 100 base pairs to 200 base pairs, 100 base pairs to 250 base pairs, 100 base pairs to 300 base pairs, 100 base pairs to 350 base pairs, 100 base pairs to 400 base pairs, 100 base pairs to 450 base pairs, 100 base pairs to 500 base pairs, 150 base pairs to 200 base pairs, 150 base pairs to 250 base pairs, 150 base pairs to 300 base pairs, 150 base pairs to 350 base pairs, 150 base pairs to 400 base pairs, 150 base pairs to 450 base pairs, 150 base pairs to 500 base pairs, 200 base pairs to 250 base pairs, 200 base pairs to 300 base pairs, 200 base pairs to 350 base pairs, 200 base pairs to 400 base pairs, 200 base pairs to 450 base pairs, 200 base pairs to 500 base pairs, 250 base pairs to 300 base pairs, 250 base pairs to 350 base pairs, 250 base pairs to 400 base pairs, 250 base pairs to 450 base pairs, 250 base pairs to 500 base pairs, 300 base pairs to 350 base pairs, 300 base pairs to 400 base pairs, 300 base pairs to 450 base pairs, 300 base pairs to 500 base pairs, 350 base pairs to 400 base pairs, 350 base pairs to 450 base pairs, 350 base pairs to 500 base pairs, 400 base pairs to 450 base pairs, 400 base pairs to 500 base pairs, or 450 base pairs to 500 base pairs. A padlock probe can have a length of, for example, 50 base pairs, 100 base pairs, 150 base pairs, 200 base pairs, 250 base pairs, 300 base pairs, 350 base pairs, 400 base pairs, 450 base pairs, or 500 base pairs.

As used herein, the term "phasing" can refer to the determination of a single-molecule origin of sequencing data. For example, phasing can be the ability to cluster nucleic acid sequencing reactions, which generate short stretches of sequencing data (short reads), into longer stretches of nucleic acid sequence information to decipher the sequence of a parental long nucleic acid molecule. Phasing can involve identifying a collection of sequencing reactions (short reads) that span the sequence of a single longer nucleic acid molecule, and accurately reconstructing the sequence of the single long DNA/RNA molecule (long read) from the shorter DNA sequencing reactions (short reads). Phase information can be used to understand gene expression patterns for genetic disease research through the phased sequencing of, for example, Human DNA, Bacterial DNA and Viral DNA. Phasing can be generated through laboratory-based experimental methods, or it can be estimated with computational and statistical approaches. In some embodiments, a mixture of nucleic acid molecules from any source is tagged. The nucleic acid mixture can have any degree of homology, including alleles of a gene within an cell, different versions of a gene within an organism (somatically mutated variants), different versions of a gene within a population of organisms, splice variants, homologous genes, heterologous genes, somatically mutated variants of a gene, duplicated genes and variants of a synthetic genes, gene libraries made in a DNA synthesis process or any combination thereof.

As used herein, the term "primer" can refer to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer. A primer can be, for example, at least 7 nucleotides long, range from 10 to 30 nucleotides, or from about 15 to about 30 nucleotides, in length. In some embodiments, primers can be somewhat longer, e.g., about 30 to about 50 nucleotides long. A primer may not have 100% complementarity to a template, for example, to be effective. A primer may only be sufficiently complementary to hybridize with a template under amplification or sequencing conditions, as appropriate.

A primer can have a length of, for example, 7 nucleotides to 75 nucleotides. A primer can have a length of, for example, at least 7 nucleotides. A primer can have a length of, for example, at most 75 nucleotides. A primer can have a length of, for example, 7 nucleotides to 10 nucleotides, 7 nucleotides to 15 nucleotides, 7 nucleotides to 20 nucleotides, 7 nucleotides to 25 nucleotides, 7 nucleotides to 30 nucleotides, 7 nucleotides to 35 nucleotides, 7 nucleotides to 40 nucleotides, 7 nucleotides to 45 nucleotides, 7 nucleotides to 50 nucleotides, 7 nucleotides to 60 nucleotides, 7 nucleotides to 75 nucleotides, 10 nucleotides to 15 nucleotides, 10 nucleotides to 20 nucleotides, 10 nucleotides to 25 nucleotides, 10 nucleotides to 30 nucleotides, 10 nucleotides to 35 nucleotides, 10 nucleotides to 40 nucleotides, 10 nucleotides to 45 nucleotides, 10 nucleotides to 50 nucleotides, 10 nucleotides to 60 nucleotides, 10 nucleotides to 75 nucleotides, 15 nucleotides to 20 nucleotides, 15 nucleotides to 25 nucleotides, 15 nucleotides to 30 nucleotides, 15 nucleotides to 35 nucleotides, 15 nucleotides to 40 nucleotides, 15 nucleotides to 45 nucleotides, 15 nucleotides to 50 nucleotides, 15 nucleotides to 60 nucleotides, 15 nucleotides to 75 nucleotides, 20 nucleotides to 25 nucleotides, 20 nucleotides to 30 nucleotides, 20 nucleotides to 35 nucleotides, 20 nucleotides to 40 nucleotides, 20 nucleotides to 45 nucleotides, 20 nucleotides to 50 nucleotides, 20 nucleotides to 60 nucleotides, 20 nucleotides to 75 nucleotides, 25 nucleotides to 30 nucleotides, 25 nucleotides to 35 nucleotides, 25 nucleotides to 40 nucleotides, 25 nucleotides to 45 nucleotides, 25 nucleotides to 50 nucleotides, 25 nucleotides to 60 nucleotides, 25 nucleotides to 75 nucleotides, 30 nucleotides to 35 nucleotides, 30 nucleotides to 40 nucleotides, 30 nucleotides to 45 nucleotides, 30 nucleotides to 50 nucleotides, 30 nucleotides to 60 nucleotides, 30 nucleotides to 75 nucleotides, 35 nucleotides to 40 nucleotides, 35 nucleotides to 45 nucleotides, 35 nucleotides to 50 nucleotides, 35 nucleotides to 60 nucleotides, 35 nucleotides to 75 nucleotides, 40 nucleotides to 45 nucleotides, 40 nucleotides to 50 nucleotides, 40 nucleotides to 60 nucleotides, 40 nucleotides to 75 nucleotides, 45 nucleotides to 50 nucleotides, 45 nucleotides to 60 nucleotides, 45 nucleotides to 75 nucleotides, 50 nucleotides to 60 nucleotides, 50 nucleotides to 75 nucleotides, or 60 nucleotides to 75 nucleotides. A primer can have a length of, for example, 7 nucleotides, 10 nucleotides, 15 nucleotides, 20 nucleotides, 25 nucleotides, 30 nucleotides, 35 nucleotides, 40 nucleotides, 45 nucleotides, 50 nucleotides, 60 nucleotides, or 75 nucleotides.

As used herein, the terms "primer site" and "primer binding site" can refer to the segment of a target nucleic acid to which a primer hybridizes.

As used herein, the term "primer pair" can refer to a set of primers including a 5' "upstream primer" or "forward primer" that hybridizes with the complement of the 5' end of the nucleic acid sequence to be amplified, and a 3' "downstream primer" or "reverse primer" that hybridizes with the 3-end of the sequence to be amplified. As will be recognized by those of skill in the art, the terms "upstream" and "downstream" or "forward" and "reverse" are not intended to be limiting, but rather provide illustrative orientation in particular embodiments.

As used herein, the term "sequencing" can refer to determining the order of nucleotides (base sequences) in a nucleic acid sample (e.g. DNA or RNA).

As used herein, the term "region of interest primer (ROIP)" can refer to the 3' terminal sequence or segment of the primer used in an elongation-based barcode tagging reaction, e.g., the 3' terminal ROIP segment can be complementary to one end of the long nucleic acid to be phase-sequenced. The ROIP can be the 3' elongation end of the primer in the barcoding reaction and can therefore defines the ends of the long molecules that can be barcoded for long read sequencing.

As used herein, the term "sequencing adaptors" can refer to nucleic acid molecules (e.g., single-stranded DNA (ssDNA)) with, e.g. about 20 to 80 bases. A sequencing adaptor can have a length of, for example, 20 bases to 80 bases. A sequencing adaptor can have a length of, for example, at least 20 bases. A sequencing adaptor can have a length of, for example, at most 80 bases. A sequencing adaptor can have a length of, for example, 20 bases to 30 bases, 20 bases to 40 bases, 20 bases to 50 bases, 20 bases to 60 bases, 20 bases to 70 bases, 20 bases to 80 bases, 30 bases to 40 bases, 30 bases to 50 bases, 30 bases to 60 bases, 30 bases to 70 bases, 30 bases to 80 bases, 40 bases to 50 bases, 40 bases to 60 bases, 40 bases to 70 bases, 40 bases to 80 bases, 50 bases to 60 bases, 50 bases to 70 bases, 50 bases to 80 bases, 60 bases to 70 bases, 60 bases to 80 bases, or 70 bases to 80 bases. A sequencing adaptor can have a length of, for example, 20 bases, 30 bases, 40 bases, 50 bases, 60 bases, 70 bases, or 80 bases. Sequencing adaptors can be universal sequences that can be used in high throughput sequencing. For example, sequencing adaptors can contain universal sequences used by high throughput sequencers to capture nucleic acid libraries and generate sequencing clusters (i.e. P5 and P7 sequences), and to generate short reads information (i.e. Read 1 and Read 2 sequences) and sample index information (i.e. P5, P7 and Read 2 sequences).

As used herein, the term "standard NGS library preparation" can be used to depict a high quality, comprehensive sequencing library preparation. Standard NGS library preparation can be used in NGS methods that employ short read library sample preparation, such as whole-genome sequencing, targeted DNA sequencing, whole-transcriptome sequencing, and targeted RNA sequencing.

As used herein, the term "tag" can refer to a short sequence that can be added to a primer, included in a sequence, or otherwise used as a label to provide a unique identifier. A sequence identifier can be a unique base sequence of varying but defined length that is used to identify a specific nucleic acid sample. For example, 4 bp (bp) can generate 44=256 unique tags. A tag can be used to determine the origin of a sample upon further processing. For example, a unique sequence tag can be used to identify the origin and coordinates of the individual sequence in the pool of a complex nucleic acid sequence mixture or amplified library. Multiple tags can be used.

As used herein, the terms "tagging", "barcoding", and "encoding reaction" can refer to reactions in which at least one nucleotide tag is added to a target nucleotide sequence. For example, a library of nucleic acid molecules can be tagged with molecule-specific barcodes using, for example, PCR amplification of the nucleic acid library. The PCR primers can insert molecule-specific barcode sequences at the termini of nucleic acid molecules; alternatively, the barcode segment can be added to the nucleic acid library by ligating the molecule specific barcodes at the termini of nucleic acid molecules using a DNA ligase.

As used herein, the term "tagged target nucleotide sequence" can refer to a nucleotide sequence with an appended nucleotide tag.

As used herein, the phrases "target nucleotide sequence" or "parental nucleic acid molecule to be sequenced" can refer to a polynucleotide molecule representing a reference (complete) nucleotide sequence of a long target nucleic acid being sequenced, such as the amplification product obtained by amplifying a target nucleic acid or the cDNA produced upon reverse transcription of an RNA target nucleic acid.

As used herein, the term "terminal adaptors" can refer to nucleic acid (e.g., ssDNA) molecules with, e.g. about 20 to 100 bases. A terminal adaptor can have a length of, for example, 20 bases to 100 bases. A terminal adaptor can have a length of, for example, at least 20 bases. A terminal adaptor can have a length of, for example, at most 100 bases. A terminal adaptor can have a length of, for example, 20 bases to 30 bases, 20 bases to 40 bases, 20 bases to 50 bases, 20 bases to 60 bases, 20 bases to 70 bases, 20 bases to 80 bases, 20 bases to 100 bases, 30 bases to 40 bases, 30 bases to 50 bases, 30 bases to 60 bases, 30 bases to 70 bases, 30 bases to 80 bases, 30 bases to 100 bases, 40 bases to 50 bases, 40 bases to 60 bases, 40 bases to 70 bases, 40 bases to 80 bases, 40 bases to 100 bases, 50 bases to 60 bases, 50 bases to 70 bases, 50 bases to 80 bases, 50 bases to 100 bases, 60 bases to 70 bases, 60 bases to 80 bases, 60 bases to 100 bases, 70 bases to 80 bases, 70 bases to 100 bases, or 80 bases to 100 bases. A terminal adaptor can have a length of, for example, 20 bases, 30 bases, 40 bases, 50 bases, 60 bases, 70 bases, 80 bases, or 100 bases. Terminal adaptors can be designed to be used as primers in conjunction with a polymerase to append nucleic acid molecules with specific sequences, including molecule-specific barcodes, sequences for downstream amplifications, and sequences used for NGS sequencing. Terminal adaptors can contain self-elongation sequences for extending and copying sequences that can be internal to the nucleic acid molecule.

Some inventive embodiments herein contemplate numerical ranges. Where a range of values is provided, it is intended that the ranges include the range endpoints, and each intervening value between the upper and lower limit of that range and any other stated or intervening value in that stated range is encompassed within the disclosure. For example, if a range of 1 μg to 8 μg is stated, it is intended that 2 μg, 3 μg, 4 μg, 5 μg, 6 μg, and 7 μg are also explicitly disclosed, as well as the range of values greater than or equal to 1 μg and the range of values less than or equal to 8 μg. Additionally, every sub range and value within the rage is present as if explicitly written out.

The length of a nucleic acid sequence that can be read using a sequencing reaction, also known as the "read-length", can be shorter than the length of entire genes and chromosomes. Due to this limitation in read-length and the fact that each sequencing reaction may sequence a different nucleic acid molecule, it can be difficult to determine whether genetic variations that are read in different nucleic acid sequencing reactions originate from the same nucleic acid molecule or from a different nucleic acid molecule.

Combinations of variations can be present in cis on one physical molecule or in trans on different molecules. Distinguishing between cis and trans variations can affect the interpretation of genetic information and can influence the understanding of disease phenotypes. Variants can include changes as small as single nucleotides to extremely large genomic variations resulting from substitutions, insertions, deletions, or changes in copy number. Some examples of complex populations of variants include: variants of synthetic genes generated using synthetic gene synthesis, populations of genes from bacterial or viral origins (e.g., microbiomes), variants of a certain gene or gene panel from complex DNA populations sampled or biopsied from the human body, and plants or DNA from environmental specimens.

The process of determining whether distant genetic variations are present on the same single nucleic acid molecule or on different nucleic acid molecules is known as "phasing". Phasing the sequence variation of long DNA/RNA molecules from complex mixtures of nucleic acid molecules that are longer than typical NGS read-lengths can be challenging, and is also known as the "phasing problem". The phasing problem can occur because it can be difficult to determine which original long DNA/RNA molecule each short-read originated from.

Synthetic long reads (SLR) technology can be used for phasing. SLR can allow short read data to be used to deduce long read sequencing information. However, the ability to multiplex multiple samples into a single sample preparation reaction can be a challenge in SLR because, for example, one unique molecular barcoding adaptor may be required to be accurately assigned to each molecule of a sample. SLR can rely on dilution of a sample for obtaining a collection of molecules comprising a unique molecular barcode. However, the concept underlying dilution-based SLR approaches can fail when the molecules of the original sample being sequenced are very similar (e.g. in variant or amplicon libraries). The reason for this can be that dilution of variant libraries may not create wells in which every molecule is unique, as in the case when fragmenting genome samples. When identical molecules share the same partition-specific barcode, the resulting barcoded short-reads can come from different original molecules and cannot be assembled into contiguous sequences with high confidence. As a result, variant libraries may not be phased using dilution based SLR technologies. Further, unreacted barcoding adaptors from the original barcoding reaction can overwrite existing barcoded molecules, incorrectly assigning two or more molecular barcodes to the same original DNA/RNA molecule. In some aspects, the disclosure provides methods and compositions to remove unreacted barcoding adaptors.

Barcode overwriting rates can be measured to be as high as 25%-75%, e.g., 25%-75% of the molecules can be assigned to 2 or more barcodes. Thus, barcode overwriting can lead to an inaccurately large number of barcodes, skewed quantification, and inefficient (low-coverage) synthetic SLR sequencing. Additionally, cross sample barcode overwriting can result in molecules from one sample being assigned to another sample because the barcode contains molecular barcode information as well as sample barcode information. In both clinical, industrial, and research settings, misassigning molecules to their correct samples can be a major source of error in sequencing.

SLR sequencing methods can also be hindered by coverage-bias, where the parental sequence is not evenly represented due to non-random fragmentation and/or site-preferential restriction enzyme digestion. Other bias-inducing steps associated with SLR can include intramolecular ligation resulting from length constraints in the dsDNA molecules being circularized.

The present disclosure provides methods and compositions for rapid, reliable, efficient and economical molecular tagging of complex populations of DNA/RNA molecules in a mixture, for example, without chambering to separate reactions. The disclosed methods can be used to construct synthetic long reads from high-throughput sequencing data. The disclosed methods can provide phased sequence information to be inferred from genomic, transcriptomic, variant and amplicon libraries.

The method described herein can generate a pool of short nucleic acid molecules with identical barcodes, wherein a barcode is unique to a long parent nucleic acid molecule. The short nucleic acid molecules can collectively cover the entire length of the long parent nucleic acid molecule. FIG. 1 illustrates a general overview of the steps of tagging and amplifying a mixture of nucleic acid molecules.

The disclosed method can include tagging nucleic acid molecules in a mixture with a unique terminal adaptor comprising a molecular barcode and a self-elongation sequence. The barcoded molecules can then be amplified, affording a sample containing a mixture of barcoded and amplified nucleic acid (e.g., dsDNA) molecules. The amplified library of dsDNA molecules can be then converted to ssDNA. A DNA polymerase can be used in a DNA polymerization reaction to intramolecularly elongate the terminal self-elongation sequences in a primer-extension reaction, evenly copying all the parts of the long ssDNA molecules. The intramolecularly elongated library can then be prepared for NGS.

In some aspects, the disclosure provides methods for high throughput and parallel tagging of mixtures of nucleic acid molecules without requiring prior knowledge of the sequences, using sequence specific reagents, requiring prior cloning, or chambering of DNA/RNA molecules into separate reaction chambers, such as 384 well plates and water in oil emulsions.

In some aspects, when the sequences of a homologous region are known, the disclosed methods can allow for high throughput and parallel tagging of mixtures of nucleotide molecules, and can obtain information from only specific regions of interest. In some embodiments, the regions of interest can be highly variable sequence regions or small variations that can be separated by homologous regions.

The present disclosure can provide a method for SLR DNA sequencing with reduced coverage-bias. The method can comprise tagging a mixture of long molecules with a unique adaptor, for example a terminal adaptor, comprising a molecular barcode and a self-elongation sequence, creating a population of copies of each tagged molecule, distributing the barcode sequence of each long molecule population along its sequence via a self-elongation reaction and amplifying read-length sized segments that contain the barcode such that they either evenly cover the long molecule sequence or cover discontiguous regions of interest from the long molecule sequence while linking them together. Grouping of the short reads according to barcodes can allow for phasing of the long nucleic acid molecules with reduced coverage bias.

The disclosed methods can obtain the full-length sequence of nucleic acid molecules longer than typical NGS read-lengths, i.e., phased sequence information. In some embodiments, the disclosed method is used to analyze splicing isoforms, characterize bacteria/viral populations, compound heterozygotes, measure allele-specific expression, and identify variant linkages.

The present disclosure can be used to analyze mixtures of DNA or RNA molecules, including different alleles of a gene within a cell, different versions of a gene within an organism (e.g., somatically mutated variants), different versions of a gene within a population of organisms, splice variants of a gene, homologous genes, heterologous genes, duplicated genes and variants of a synthetic genes, and gene libraries made in a nucleic acid synthesis process.

In some aspects, a method for reducing coverage-bias of long nucleic acid molecules in synthetic long-read (SLR) sequencing is described herein.

In some embodiments, the average length of the self-elongating nucleic acid molecules in the mixture of nucleic acid molecules is from about 500 to about 20,000 bp. In some embodiments, the average length of the self-elongating nucleic acid molecules in the mixture of nucleic acid molecules is from about 500 to about 1,000; about 1,000 to about 3,000; about 1,000 to about 5,000; about 5,000 to about 7,500; about 2,500 to about 10,000; about 10,000 to about 12,500; about 10,000 to about 15,000; about 10,000 to about 17,500; or about 10,000 to about 20,000 bp. In some embodiments, the average length of the self-elongation nucleic acid molecules in the mixture of nucleic acid molecules is from about 1,000 to about 3,000 bp. In some embodiments, the average length of the self-elongation nucleic acid molecules in the mixture of nucleic acid molecules is from about 3,000 to about 5,000 bp. In some embodiments, the average length of the self-elongation nucleic acid molecules in the mixture of nucleic acid molecules is from about 5,000 to about 7,500 bp.

In the presently disclosed method, a population of approximately 100, approximately 101, approximately 102, approximately 103, approximately 104, approximately 105, approximately 106, approximately 107, approximately 108, or approximately 109, nucleic acid molecules in the complex mixture can be desired.

A. Step 0: Sample Preparation

A mixture of nucleic acid molecules longer than typical NGS read lengths can be provided for analysis. The mixture of DNA/RNA molecules can be obtained from any source and can have any degree of homology. In some embodiments, the mixture comprises nucleic acid molecules of varying lengths.

In some embodiments, the mixture comprises DNA. In some embodiments, the mixture comprises RNA. If the starting material includes RNA, the RNA molecules can be converted to DNA, for example, by reverse transcription to cDNA. In some embodiments, DNA that is reverse-transcribed from RNA is tagged during the reverse transcription step, or after the RNA has been reverse transcribed into cDNA. In some embodiments, the mixture comprises genomic DNA. In some embodiments, the mixture comprises nucleic acid strands from a cell-free nucleic acid, a cell, or a biological sample. Whole-cell mRNA may be extracted and converted into cDNA using a reverse transcriptase. The reverse transcription may be conducted as a bulk reaction or inside partitions under single-cell conditions, with the resulting cDNA being labeled with partition-specific barcodes. The cDNA, including a mixture of all transcribed molecules, may then be tagged at their 5' and/or 3' end with molecule-specific barcode sequences. As used herein, 5' and 3' can be used to indicate relative position. For example, a 5' portion can, but does not have to, include a portion comprising a 5' end. A 5' portion can include a portion that is 5' to another portion of a nucleic acid molecule (e.g., a 3' portion) but that does not necessarily include a 5' end. Likewise, a 3' portion can, but does not have to, include a portion comprising a 3' end. A 3' portion can include a portion that is 3' to another portion of a nucleic acid molecule (e.g., a 5' portion) but that does not necessarily include a 3' end.

In some embodiments, a molecule-specific terminal adaptor is present at both ends of a long nucleic acid molecule. In some embodiments, the molecule-specific terminal adaptor is present at only one end of a long nucleic acid molecule. In some embodiments, the location of the molecule-specific terminal adaptor is upstream of the long nucleic acid molecule. In some embodiments, the location of the molecule-specific terminal adaptor is downstream of the long nucleic acid molecule.

In some embodiments, the DNA molecules can be molecules incorporated into vectors that serve as DNA libraries. In some embodiments, a mixture of DNA molecules can include a mixture of DNA vectors, wherein each vector includes a target molecule with a desired sequence. The use of DNA molecule libraries can help utilize the known sequence of a vector flanking a molecule for subsequent molecular manipulations. In some embodiments, a DNA mixture can include PCR products.

Figure 4:
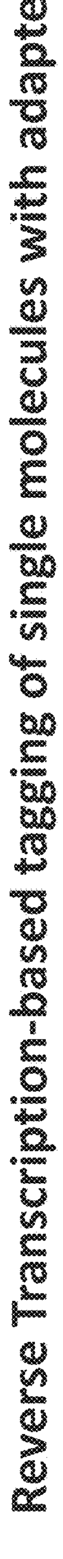
FIG. 4 shows an illustrative scheme for appending an adaptor, for example, to an RNA molecule. The adaptor can be appended during reverse transcription or second strand cDNA strand generation. Appending can be performed by, for example, ligation or elongation.
Figure 4:
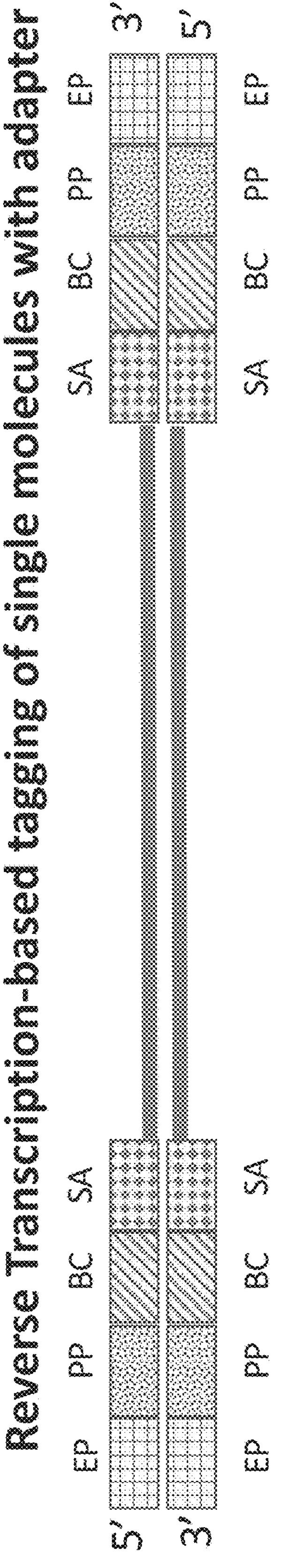
Figure 4:
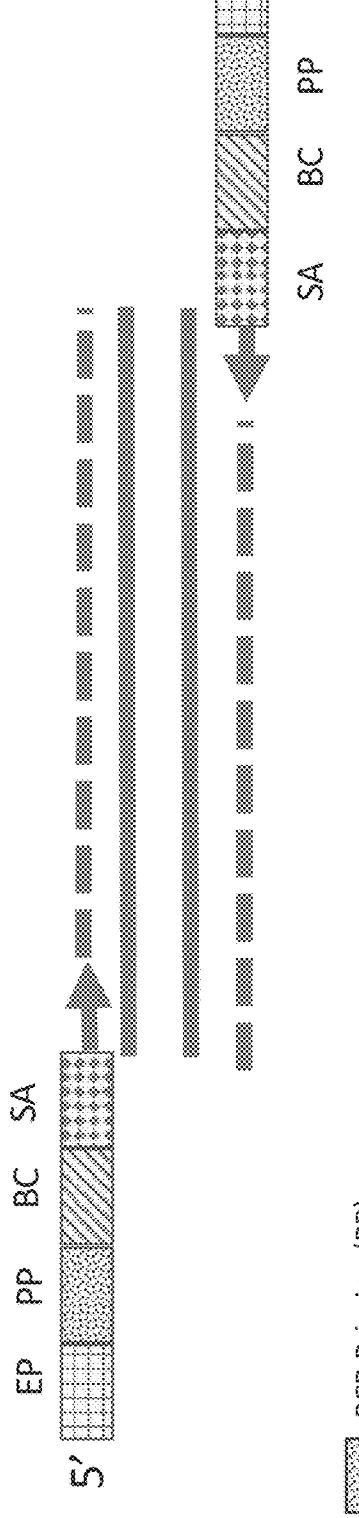

FIG. 4 illustrates reverse transcription-based tagging of single RNA molecules with an adaptor, and nucleic acid elongation-based tagging of single molecules with an adaptor.

In some embodiments, the sample comprises DNA molecules. In some embodiments, a mixture of DNA molecules is uniquely tagged with similar barcodes using a primer driven elongation reaction. In some embodiments, the mixture of DNA molecules is uniquely tagged with similar barcodes by integrating the barcodes into molecules of a DNA library from the outset if the library is synthetically assembled using DNA synthesis technology. If the barcode is integrated into the molecules of the library during DNA synthesis, the barcode can comprise random sequences, or a collection of known sequences that can be equal or larger in number than the number of unique DNA molecules synthesized.

In some embodiments, the average length of nucleic acid molecules in a mixture is about 500 bp to about 5,000 bp. In some embodiments, the average length of nucleic acid molecules in a mixture is at least about 500 bp. In some embodiments, the average length of nucleic acid molecules in a mixture is at most about 5,000 bp. In some embodiments, the average length of nucleic acid molecules in a mixture is about 500 bp to about 1,500 bp, about 500 bp to about 2,000 bp, about 500 bp to about 2,500 bp, about 500 bp to about 3,000 bp, about 500 bp to about 3,500 bp, about 500 bp to about 4,000 bp, about 500 bp to about 4,500 bp, about 500 bp to about 5,000 bp, about 1,500 bp to about 2,000 bp, about 1,500 bp to about 2,500 bp, about 1,500 bp to about 3,000 bp, about 1,500 bp to about 3,500 bp, about 1,500 bp to about 4,000 bp, about 1,500 bp to about 4,500 bp, about 1,500 bp to about 5,000 bp, about 2,000 bp to about 2,500 bp, about 2,000 bp to about 3,000 bp, about 2,000 bp to about 3,500 bp, about 2,000 bp to about 4,000 bp, about 2,000 bp to about 4,500 bp, about 2,000 bp to about 5,000 bp, about 2,500 bp to about 3,000 bp, about 2,500 bp to about 3,500 bp, about 2,500 bp to about 4,000 bp, about 2,500 bp to about 4,500 bp, about 2,500 bp to about 5,000 bp, about 3,000 bp to about 3,500 bp, about 3,000 bp to about 4,000 bp, about 3,000 bp to about 4,500 bp, about 3,000 bp to about 5,000 bp, about 3,500 bp to about 4,000 bp, about 3,500 bp to about 4,500 bp, about 3,500 bp to about 5,000 bp, about 4,000 bp to about 4,500 bp, about 4,000 bp to about 5,000 bp, or about 4,500 bp to about 5,000 bp. In some embodiments, the average length of nucleic acid molecules in a mixture is about 500 bp, about 1,500 bp, about 2,000 bp, about 2,500 bp, about 3,000 bp, about 3,500 bp, about 4,000 bp, about 4,500 bp, or about 5,000 bp.

B. Step 1a: Terminal Tagging

The nucleic acid molecules in the mixture can be tagged with a unique terminal adaptor comprising a molecular barcode and a self-elongation sequence (FIG. 1, Step 1a). In some embodiments, the mixture of nucleic acid molecules can be tagged by mixing the nucleic acid molecules with an excess amount of unique barcode sequences. In some embodiments, the mixture of nucleic acid molecules can be mixed with an excess amount of unique barcode sequences that can be a combination of 6, 7, 8, 9, 10, 11, 12, 13, 14, 15, 16, 17, 18, 19, or 20 bp sequences, and subsequently attaching the unique barcode sequence to the nucleic acid molecules using blunt end ligation. The resulting sample can be a mixture of uniquely barcoded nucleic acid molecules.

Figure 3:
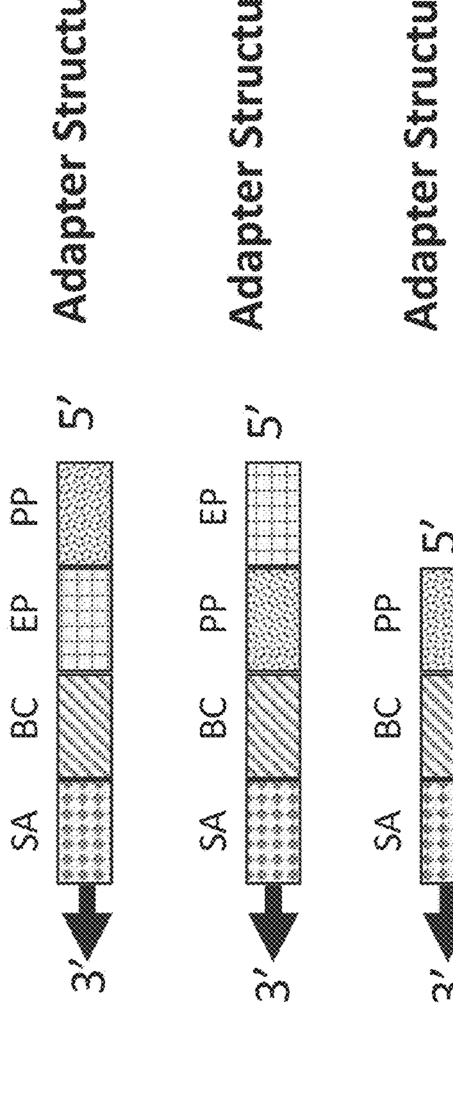
FIG. 3 illustrates exemplary adaptors comprising molecule-specific barcodes. The adaptors may or may not comprise an elongation priming sequence.

FIG. 3 illustrates an exemplary structure of an adaptor containing molecule-specific barcodes (BC) with or without an elongation primer (EP). In some embodiments, the adaptor has a 1) barcode segment (BC) that is a unique, single molecule identifier; and 2) an elongation priming segment (EP) that encodes for the reverse complement of an internal sequence as a DNA polymerization primer. In some embodiments, the adaptor can has additional segments, such as a sequencing adaptor segment (SA) and a universal PCR priming segment (PP).

In some embodiments, a molecule-specific terminal adaptor is present at both ends of a long nucleic acid molecule. In some embodiments, the molecule-specific terminal adaptor is present at only one end of a long nucleic acid molecule. In some embodiments, the location of the molecule-specific terminal adaptor is upstream of the long nucleic acid molecule. In some embodiments, the location of the molecule-specific terminal adaptor is downstream of the long nucleic acid molecule. In some embodiments, a first adaptor can comprise a second barcode common to each fragment of a single-stranded nucleic acid molecule.

In some embodiments, the molecular barcode in the terminal tag comprises an entirely random sequence. In some embodiments, the molecular barcode in the terminal tag comprises a semi-random sequence, for example, a combination of a random molecule-specific sequence and a known sequence, wherein the known sequence is used to identify the sample from which multiple parental nucleic sequences originate. In some embodiments, the molecular barcode in the terminal tag comprises an entirely known sequence, including only a molecule-specific sequence, or both a molecule-specific sequence and a sample-specific sequence.

In some embodiments, the elongation sequence comprises an entirely random sequence. In some embodiments, the elongation sequence comprises a combination of a random molecule-specific sequence and a known sequence, wherein the known sequence is used to identify the sample from which multiple parental nucleic sequences originate. In some embodiments, the elongation sequence comprises an entirely known sequence, including only a molecule-specific sequence, or both a molecule-specific sequence and a sample-specific sequence. In some embodiments, the elongation sequence comprises a substantial or complete complementarity to a portion of the target nucleic acid sequence. In some embodiments, the elongation sequence comprises a partial complementarity to a portion of the target nucleic acid sequence. In some embodiments, the elongation sequence comprises, for example, at least about: 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% complementarity to a portion of the target nucleic acid sequence that it anneals to.

In some embodiments, the barcode sequence can have a length of about 10 bp, about 20 bp, about 30 bp, about 40 bp, or about 50 bp. In some embodiments, the barcode sequence can have a length of about 15 bp, 20 bp, 25 bp, or 30 bp. In some embodiments, the barcode sequence can have a length of about 20 bp or about 25 bp.

In some embodiments, a barcode sequence can have a length of about 5 bp to about 50 bp. In some embodiments, a barcode sequence can have a length of at least about 5 bp. In some embodiments, a barcode sequence can have a length of at most about 50 bp. In some embodiments, a barcode sequence can have a length of about 5 bp to about 10 bp, about 5 bp to about 15 bp, about 5 bp to about 20 bp, about 5 bp to about 25 bp, about 5 bp to about 30 bp, about 5 bp to about 35 bp, about 5 bp to about 40 bp, about 5 bp to about 45 bp, about 5 bp to about 50 bp, about 10 bp to about 15 bp, about 10 bp to about 20 bp, about 10 bp to about 25 bp, about 10 bp to about 30 bp, about 10 bp to about 35 bp, about 10 bp to about 40 bp, about 10 bp to about 45 bp, about 10 bp to about 50 bp, about 15 bp to about 20 bp, about 15 bp to about 25 bp, about 15 bp to about 30 bp, about 15 bp to about 35 bp, about 15 bp to about 40 bp, about 15 bp to about 45 bp, about 15 bp to about 50 bp, about 20 bp to about 25 bp, about 20 bp to about 30 bp, about 20 bp to about 35 bp, about 20 bp to about 40 bp, about 20 bp to about 45 bp, about 20 bp to about 50 bp, about 25 bp to about 30 bp, about 25 bp to about 35 bp, about 25 bp to about 40 bp, about 25 bp to about 45 bp, about 25 bp to about 50 bp, about 30 bp to about 35 bp, about 30 bp to about 40 bp, about 30 bp to about 45 bp, about 30 bp to about 50 bp, about 35 bp to about 40 bp, about 35 bp to about 45 bp, about 35 bp to about 50 bp, about 40 bp to about 45 bp, about 40 bp to about 50 bp, or about 45 bp to about 50 bp. In some embodiments, a barcode sequence can have a length of about 5 bp, about 10 bp, about 15 bp, about 20 bp, about 25 bp, about 30 bp, about 35 bp, about 40 bp, about 45 bp, or about 50 bp.

In some embodiments, the barcode sequence can include a unique sequence that can be used to later identify the nucleic acid molecule, and a shared or universal sequence allowing for parallel amplification of all the tagged nucleic acid molecules in the mixture. In some embodiments, the shared sequence of the barcode tag configured to flank the 3' end of the nucleic acid molecule can be different from the shared sequence of the barcode tag configured to flank the 5' end of the nucleic acid molecule.

In some embodiments, blunt end ligation, TA ligation, or primer extension is used to append the long nucleic acid molecules in the mixture with unique tags containing molecule-specific barcodes and self-elongation sequences. In some embodiments, the mixture of nucleic acid molecules is appended with unique tags by carrying out PCR with primers containing the unique tag. In some embodiments, the mixture of nucleic acid molecules is appended with unique tags by including the unique tag at the terminals during a DNA synthesis step. In some embodiments, sequence independent tagging can be performed during DNA synthesis to obtain synthesized DNA sequences flanked with barcode tags. In some embodiments, barcoding of synthetic DNA can be used in the quality control thereof.

In some aspects, the long nucleic acid molecules in the mixture may be appended with unique tags that contain both the molecule-specific barcode and the self-elongation sequence. In some aspects, the long nucleic acid molecules in the mixture may be appended with unique tags that contain the molecule-specific barcode but not the self-elongation sequence.

In some embodiments, the initial tagging of the mixture of single nucleic acid molecules with unique tags comprises carrying out PCR with primers containing a molecule-specific tag. The PCR can be performed with both primers containing the molecule-specific tags or only one of the two primers containing the molecule-specific tag. In some embodiments, PCR is performed with an oligonucleotide comprising a complement of the first adaptor. In some embodiments, PCR is performed with an oligonucleotide that comprises a reverse complement of the first adaptor and a sequence complementary to at least a portion of a template nucleic acid. In some embodiments, the 3' end of the nucleotide comprises a sequence complementary to at least a portion of a template nucleic acid. In some embodiments, PCR is performed with an oligonucleotide that comprises a complement of the first adaptor and a sequence complementary to at least a portion of a template nucleic acid, wherein the sequence complementary to at least a portion of the template nuclei acid comprises a random sequence or a complete complementary to the portion of the template nuclei acid.

In some embodiments, the initial tagging of the mixture of single nucleic acid molecules with unique tags comprises adding a molecule-specific tag to each nucleic acid molecule using blunt end ligation. In some embodiments, the initial tagging of the mixture of single nucleic acid molecules with unique tags comprises adding a molecule-specific tag to each nucleic acid molecule using TA ligation. In some embodiments, the initial tagging of the mixture of nucleic acid molecules with unique tags comprises appending the unique molecule-specific tag during nucleic acid synthesis. In some embodiments, the initial tagging of RNA molecules with unique tags comprises adding the molecule-specific tag during reverse transcription.

In some embodiments, the self-elongation sequence is appended to long nucleic acid molecules with molecule-specific barcodes using blunt ligation, TA ligation, ssDNA ligation or PCR primer extension. In some embodiments, the self-elongation sequence in the molecule-specific terminal adaptor is at the 5'-end of the adaptor, and a reverse complement of the elongation sequence is appended to a target nucleic acid via PCR. In some embodiments, the self-elongation sequence in the molecule-specific terminal adaptor is a 3' to a 5' terminal universal PCR amplification sequence that is removed prior to the elongation step. In some embodiments, the self-elongation sequence in the molecule-specific terminal adaptor is 5' to the universal PCR amplification sequence.

In some embodiments, the self-elongation sequence in the molecule-specific terminal adaptor is at the 3'-end of the nucleic acid molecule and comprises a sequence selected from a target-specific self-elongation sequence or a random sequence, such as a 6-20 base pair random nucleic acid sequence. In some embodiments, the self-elongation sequence at the 3'-end of the molecule-specific terminal adaptor is a target sequence complementary to an internal sequence of the uniquely barcoded and elongation-primed long ssDNA molecules in the mixture. In some embodiments, several target specific self-elongation sequences complementary to multiple locations on the ssDNA can be designed such that the self-elongation events collectively cover the ssDNA molecule, thereby generating short reads that evenly cover the long ssDNA molecule. In some embodiments, the elongation sequence is complementary to at least a portion of a nucleic acid sequence in a nucleic acid strand or molecule.

Figure 5:
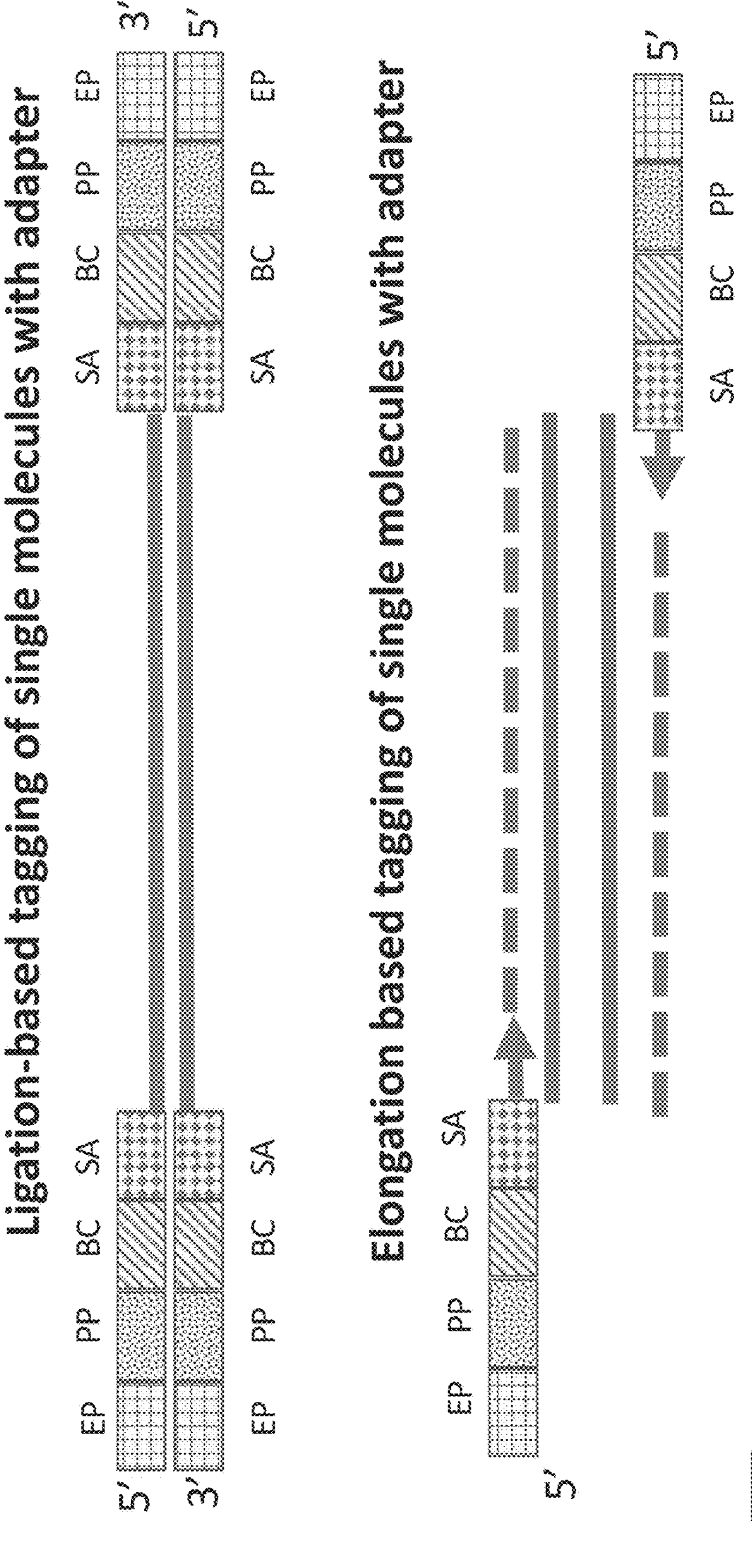
FIG. 5 shows an illustrative scheme for appending an adaptor, for example, to a DNA (e.g., cDNA, genomic DNA, cell free DNA) molecule. Appending can be performed by, for example, ligation or elongation.

FIG. 5 illustrates nucleic acid ligation-based and nucleic acid elongation-based tagging of single molecules with an adaptor, and nucleic acid elongation-based tagging of single molecules with an adaptor.

Figure 6:
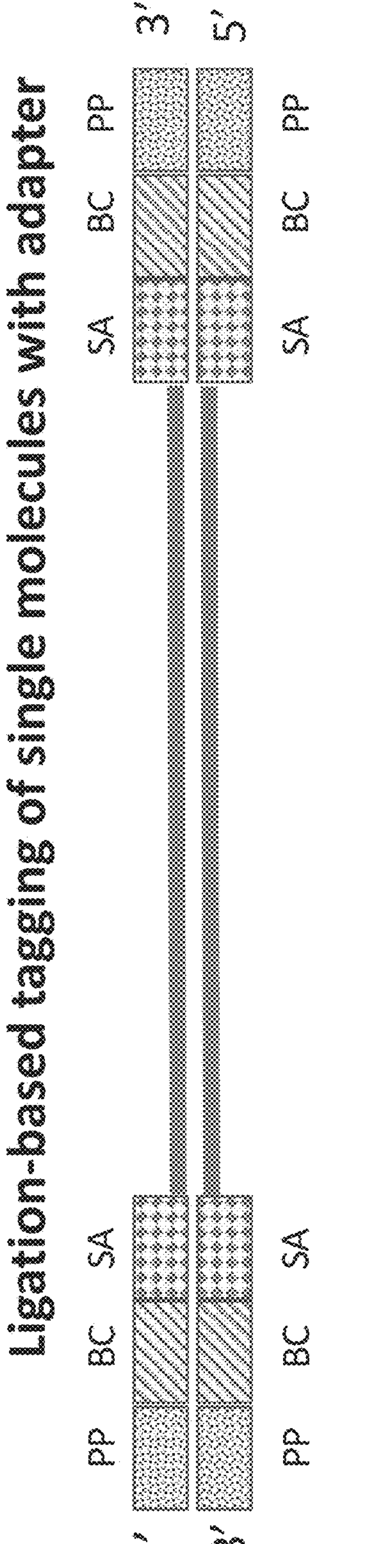
FIG. 6 shows an illustrative scheme for appending an adaptor that may not comprise an elongation priming sequence.
Figure 6:
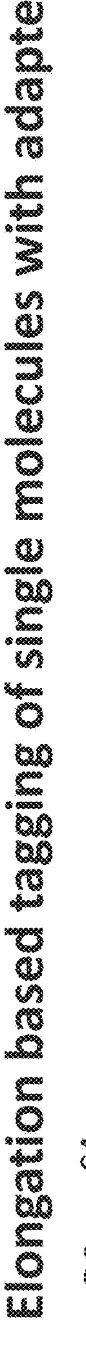
Figure 6:
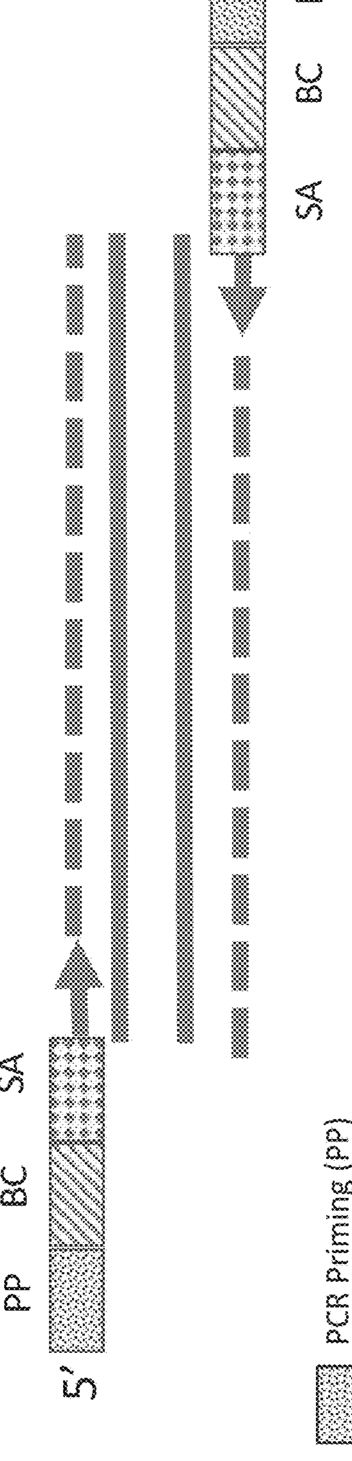

FIG. 6 illustrates an alternative method for nucleic acid ligation-based tagging and nucleic acid elongation-based tagging of single molecules without the use of an elongation primer.

The nucleic acid strands can be purified after the adaptor is appended. In some embodiments, purification of the nucleic acids comprises removing one or more unappended adaptors or enzymatic digestion of one or more unappended adaptors. In some embodiments, the nucleic acids can be purified via enzymatic digestion of one or more unappended adaptors using an exonuclease. In some embodiments, the adaptor comprises uracil, and the unappended adaptors can be removed using a uracil-DNA glycosylase, an endonuclease, or both. In some embodiments, the nucleic acid strands can be purified using solid phase reversible immobilization, column-based solid phase extraction, or gel filtration to remove the unappended adaptors.

C. Step 1b: Amplification with Universal Terminal Sequences

The barcoded molecules can then be amplified using, for example, polymerase chain reaction (PCR)-based amplification (FIG. 1, Step 1b). The resulting sample contains a mixture of barcoded and amplified dsDNA molecules.

In the event that the self-elongation sequence is not included in the unique terminal adaptor in Step 1a, one or multiple self-elongation sequences can be appended to the unique terminal adaptor in Step 1b using, for example, PCR-based amplification.

In some embodiments, the disclosed method uses a polymerase to elongate a primer and/or to amplify a mixture to produce a mixture of uniquely barcoded dsDNA molecules with varying lengths. In some embodiments, initial amplification of the uniquely tagged single nucleic acid molecules in the starting mixture is performed using PCR primers specific to the common sequence in the unique molecular tags. In some embodiments, the uniquely barcoded dsDNA is fragmented. The disclosed method can further involve obtaining sequence information from the uniquely barcoded nucleic acid molecules of varying lengths.

In some embodiments, PCR amplification is utilized to generate multiple copies of each parental long nucleic acid molecule with a molecule-specific terminal tag. In some embodiments, amplification is completed in a single reaction, wherein each sample with a pool of uniquely tagged molecules is amplified individually. In some embodiments, amplification can be completed as a multiplexed reaction, wherein multiple samples, each with a pool of uniquely tagged molecules with a sample-specific sequence shared amongst the pool, can be amplified as a single reaction.

In some embodiments, the elongation reaction copies, without bias, loci that can be evenly spread throughout the long nucleic acid molecule so that the loci of interests can be adjacent to and share the same molecule-specific barcode if they originate from the same single long molecule. In some embodiments, the elongation reaction copies without bias loci that can be separated by 200-10,000 bp such that the loci of interests on the same single long molecule share the same molecule-specific barcode.

In some embodiments, the mixture of uniquely tagged nucleic acid molecules is amplified using PCR primers specific to the shared sequence of the unique molecular tags. In some embodiments, the mixture of uniquely tagged nucleic acid molecules is amplified using PCR primers that contain the shared sequences of the unique molecular tags, as well as different elongation sequences such that each molecule-specific barcode is associated with one or more self-elongation sequence.

In some embodiments, amplification comprises at least one cycle of the sequential procedures of: denaturing the nucleic acid duplex to separate the strands, annealing at least one primer with complementary or substantially complementary sequences in at least one target nucleic acid; and synthesizing at least one strand of nucleotides in a template-dependent manner using a polymerase. In some embodiments, the amplification cycle described above is repeated. In some embodiments, the amplification cycle described above is not repeated.

Figure 7:
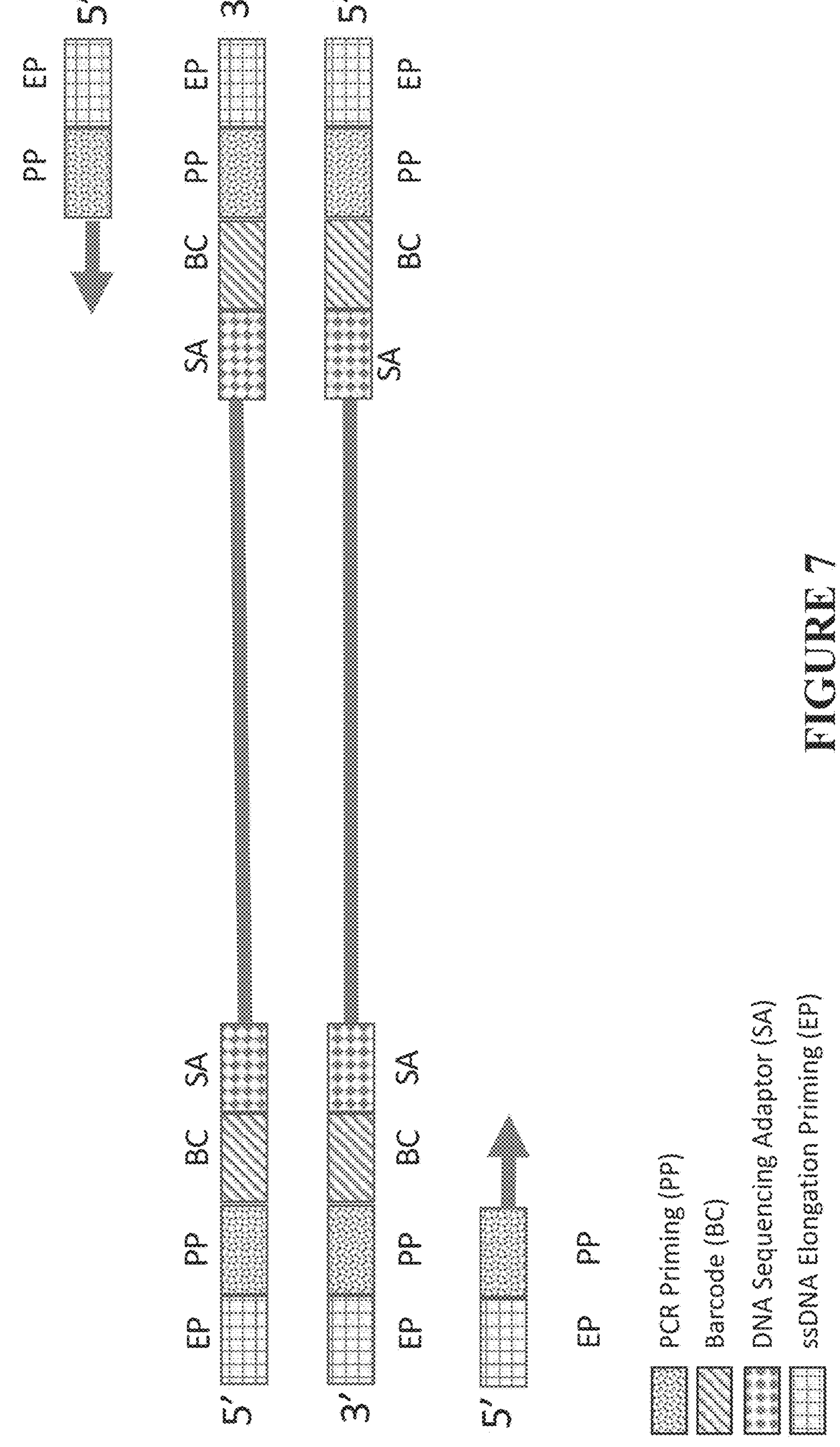
FIG. 7 shows an illustrative scheme for amplifying a tagged nucleic acid comprising the elongation priming sequence or a complement thereof is, for example, at the 5' terminus.

FIG. 7 illustrates a method for tagging single molecules where tagged single nucleic acid molecules can be amplified using an adaptor in which the elongation primer is at the 5' terminus.

Figure 8:
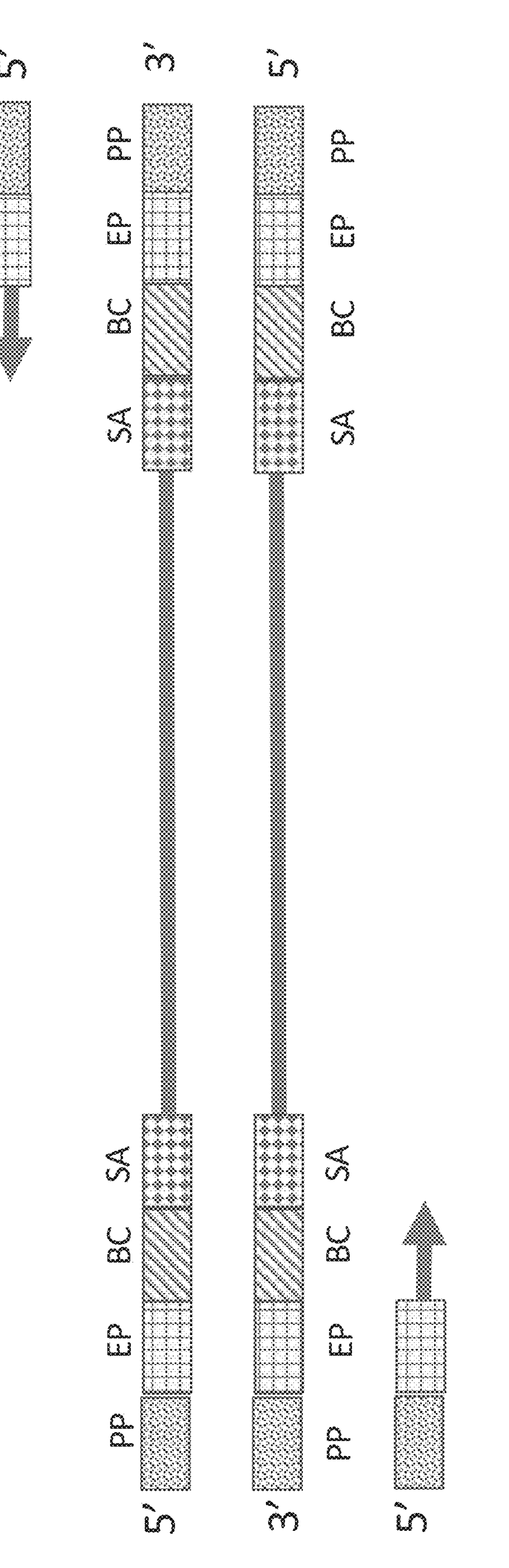
FIG. 8 shows an illustrative scheme for amplifying a tagged nucleic acid comprising a PCR priming sequence or a complement thereof is, for example, at the 5' terminus.

FIG. 8 illustrates a method for tagging single molecules where tagged single nucleic acid molecules can be amplified using an adaptor in which the PCR primer is at the 5' terminus.

Figure 9:
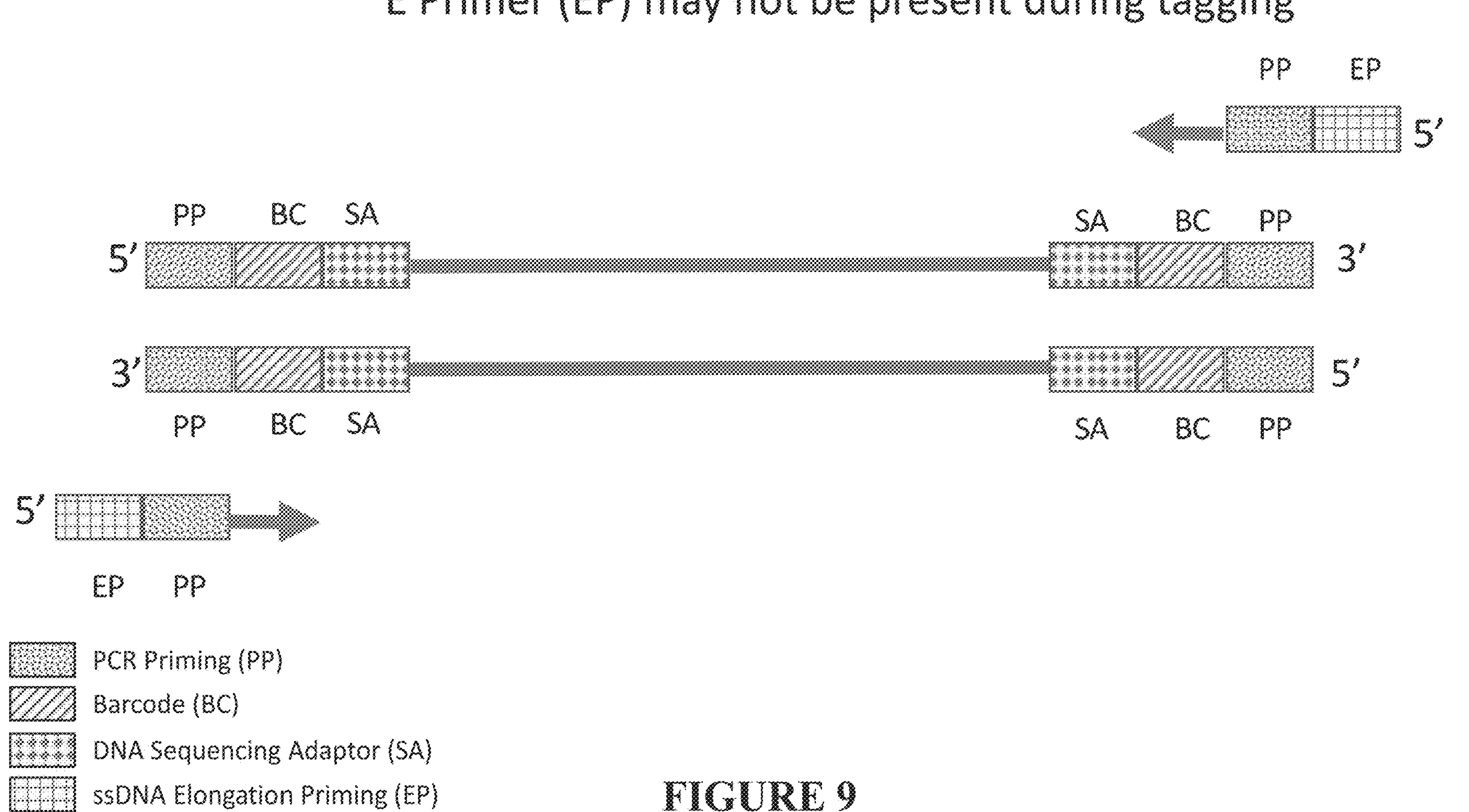
FIG. 9 shows an illustrative scheme for amplifying a tagged nucleic acid that does not comprise an elongation priming sequence or a complement thereof. The elongation priming sequence or a complement thereof can be appended to the tagged nucleic acid using, for example, an amplification primer.

FIG. 9 illustrates a method for tagging single molecules where tagged single nucleic acid molecules can be amplified using an adaptor in which the elongation primer is absent.

In some embodiments, the unique terminal barcoding adaptors can be removed after the uniquely barcoded parental long nucleic acid molecules can be generated and before many copies of the uniquely barcoded nucleic acid molecules can be made.

In some embodiments, the unique terminal barcoding adaptors can be removed through enzymatic digestion using an exonuclease with specificity to single-stranded, short nucleotides. In some embodiments, the unique terminal barcoding adaptors contain Uracil nucleotides, and the barcoding adaptors can be digested using a combination of uracil-DNA glycosylase and an endonuclease to degrade the uracil-containing barcode adaptors. In some embodiments, the unique terminal barcoding adaptors can be removed through the use of non-enzymatic purification techniques, such as solid-phase immobilization of the nucleic acid using beads, column-based purification and gel filtration, and recovery of the uniquely barcoded long nucleic acid molecules.

D. Step 2: Conversion of dsDNA to ssDNA

Figure 2:
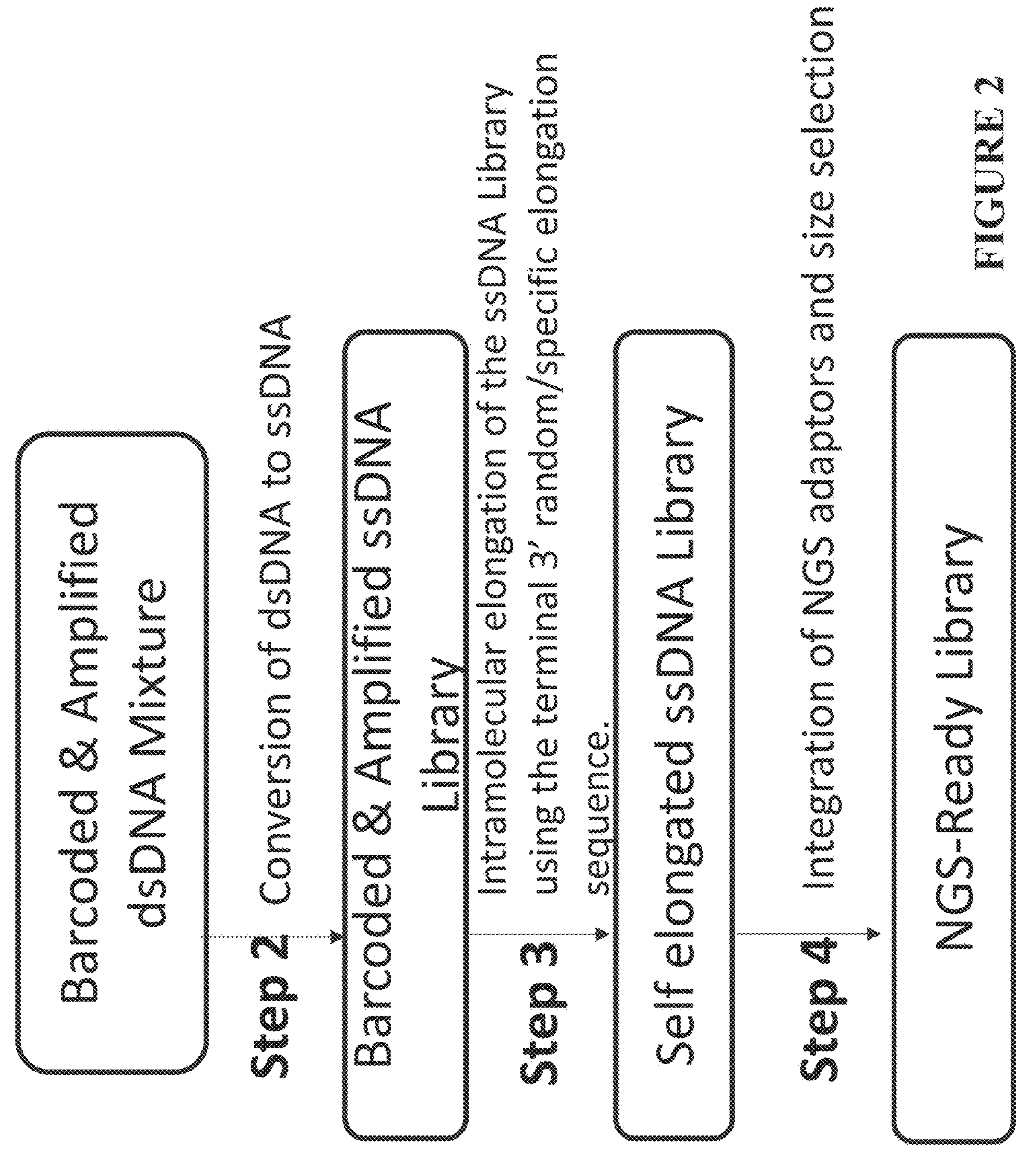
FIG. 2 depicts an illustrative scheme for preparing barcoded and amplified nucleic acid (e.g., DNA) molecules for NGS.

FIG. 2 illustrates a general overview of the steps of preparing barcoded and amplified nucleic acid molecules for an NGS-ready library.

The amplified library of dsDNA molecules can be converted to ssDNA (FIG. 2, step 2). In some embodiments, dsDNA molecules can be converted to ssDNA by degrading one strand of a uniquely barcoded DNA, physically binding one strand of the uniquely barcoded DNA molecule on a solid surface and separating the unbound strand via washing, or by denaturing the dsDNA molecules under dilute conditions. The resulting sample can contain a pool of uniquely barcoded and elongation-primed ssDNA molecules.

dsDNA molecules can be denatured using an enzyme, such as exonuclease. In some embodiments, dsDNA molecules can be denatured using a lambda exonuclease. dsDNA molecules can also be denatured through heat or alkaline denaturation.

In some embodiments the tagged dsDNA can be bound to a streptavidin-coated solid surface (e.g., streptavidin magnetic beads) through a 5' biotin primer modification, and ssDNA can be prepared for intramolecular elongation from the non-bound opposite strand by washing off the unbound strand from the beads either by heat denaturation or alkaline denaturation.

In some embodiments, the tagged dsDNA can be selectively phosphorylated at one of its 5' termini, and ssDNA can be prepared for intramolecular elongation from the dsDNA through the use of an exonuclease such as Lambda exonuclease that selectively degrades the 5' phosphorylated strands.

In some embodiments, the PCR primer segment can be removed to generate ssDNA when the PCR priming segment can be at the 5' terminus. In some embodiments, the PCR primer segment can be removed using deoxyuridine triphosphate (dUTP) cleavage. In some embodiments, dUTP a very small fraction of dUTP can be incorporated into the PCR product. In some embodiments, dUTP can be incorporated into the PCR product in an amount of about 1, 2, 3, 4, 5, 6, 7, 8, 9, or 10 nucleotides per strand of DNA. The PCR products can then be treated with a combination of enzymes that create a nick at the U sites on each DNA strand, and nick translate from the nick on opposing strands. When the nick translation from opposing strands meet, a double strand break can be created, resulting in fragmented dsDNA. The remaining PCT primer segment at the 3' terminus can be cleaved by DNA blunting. In some embodiments, T4 DNA polymerase can be used for DNA blunting of the 3' terminus.

Figure 10:
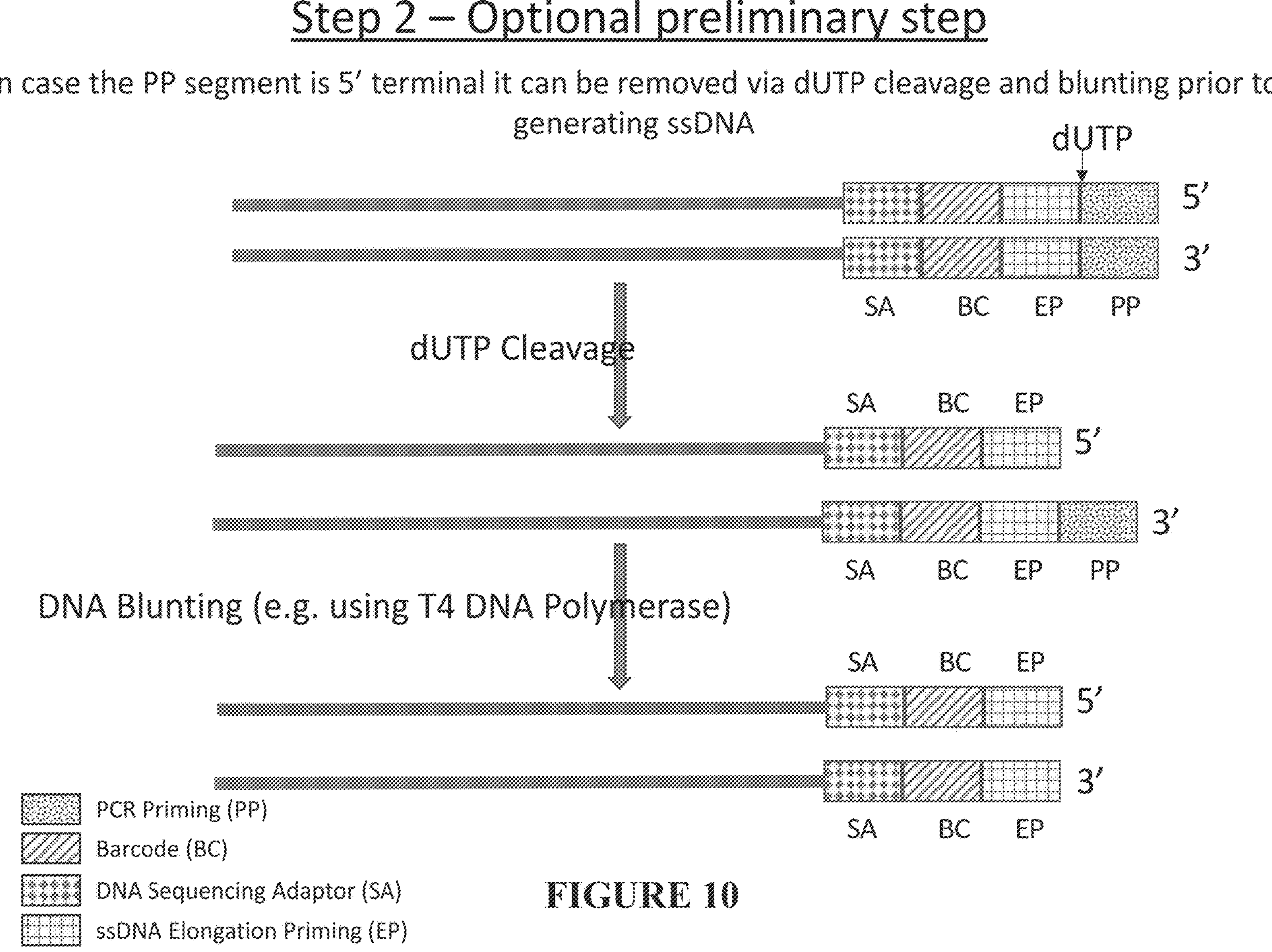
FIG. 10 shows an illustrative scheme for removing a terminal PCR primer segment from a tagged nucleic acid.

FIG. 10 illustrates a process for removing the PCR primer segment to generate ssDNA when the PCR priming segment can be at the 5' terminus. The PCR primer segment can be removed via dUTP cleavage, followed by DNA blunting (e.g., T4 DNA polymerase).

Figure 11:
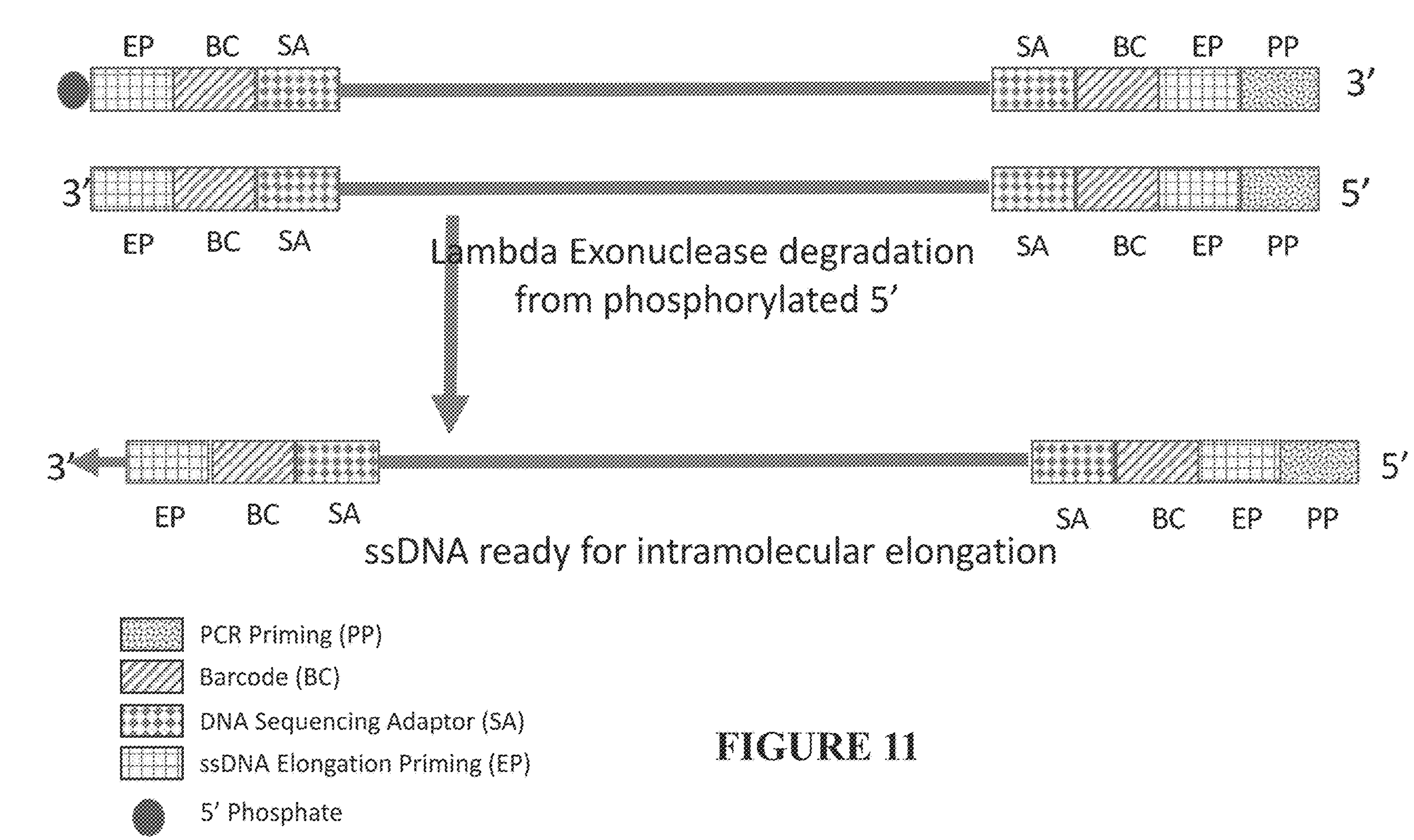
FIG. 11 shows an illustrative scheme to generate a single-stranded nucleic acid (e.g., ssDNA) from a double-stranded nucleic acid (e.g., dsDNA) when the PCR priming sequence has been removed, for example, via dUTP and blunting.

FIG. 11 illustrates a process for removing the PCR primer segment to generate ssDNA when the PCR priming sequence has been removed via dUTP and blunting. The molecule can be subjected to lambda exonuclease degradation from the phosphorylated 5' terminus, resulting in ssDNA ready for intramolecular elongation.

FIG. 12 illustrates a method of generating ssDNA from dsDNA when the PCR primer segment may not be at the 5' terminus and may not have been removed. The molecule can be subjected to lambda exonuclease degradation from the phosphorylated 5' terminus, resulting in ssDNA ready for intramolecular elongation.

Figure 13:
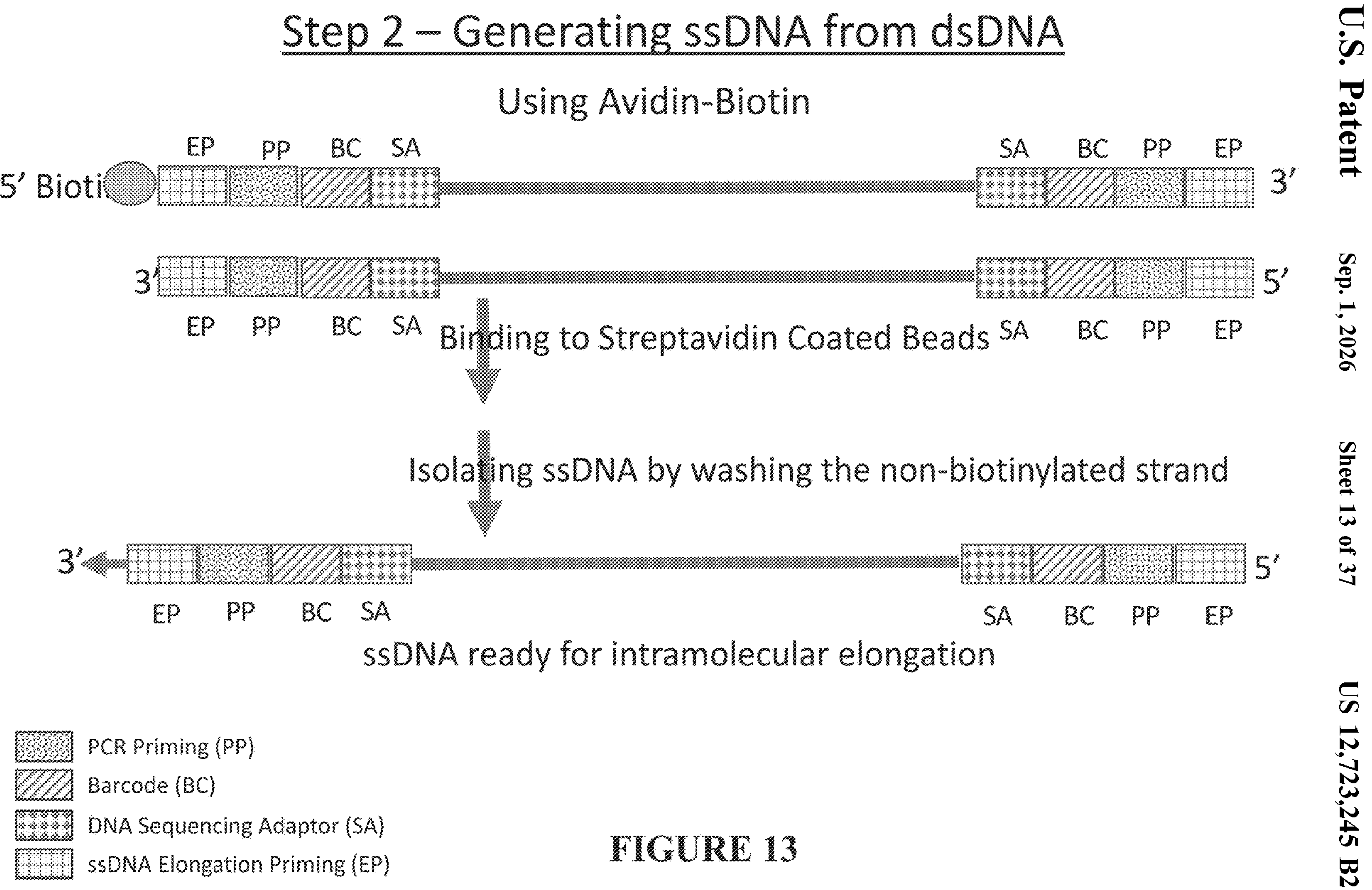
FIG. 13 shows an illustrative scheme to generate a single-stranded nucleic acid from a double-stranded nucleic acid using streptavidin coated beads.

FIG. 13 illustrates a method of generating ssDNA from dsDNA using streptavidin coated beads. The molecule can be bound to Streptavidin coated beads and the ssDNA can be isolated by washing the non-biotinylated strands of DNA, resulting in ssDNA ready for intramolecular elongation.

E. Step 3: Intramolecular Elongation of ssDNA Library

An appended elongation sequence or a complement thereof can intramolecularly anneal to a portion of a target nucleic acid. The target nucleic acid can be a single-stranded nucleic acid. The target nucleic acid can be a double-stranded nucleic acid. In some aspects, an elongation sequence can anneal intramolecularly to a single-stranded portion of a nucleic acid strand (e.g., the strand that is annealed to or conjugated to the elongation sequence) in a double-stranded nucleic acid.

A DNA polymerase can be used in a DNA polymerization reaction for intramolecular elongation of the terminal self-elongation sequences in a primer-extension reaction, which evenly copies all the parts of the long ssDNA molecules (FIG. 2, step 3).

When the elongation sequence at the termini provides a random and self-complementary (intramolecular) nucleic acid sequence, polymerization (elongation) can be initiated at various loci at which the random elongation sequence primes the elongation process. Each random 3' terminus can prime a single elongation reaction. In some embodiments, the collection of random 3' termini on different molecules can prime self-elongation reactions throughout many loci spread along the sequence of ssDNA.

In some embodiments, the terminal self-elongation sequences can be adjacent to the barcode. The elongation reaction evenly copies all parts of the long nucleic acid molecules such that they can be adjacent to the same barcode if they originate from the same single long molecule.

In some embodiments, the length of elongation can be limited to, on average, the read-length of NGS by controlling the temperature, incubation time at each temperature, and nucleotide concentration of the DNA polymerase-driven self-elongation reaction. In some embodiments, the efficiency of the intramolecular elongation reaction can be controlled by altering the concentration of molecules with terminal self-elongation sequences, the concentration of primers for NGS library construction, and number of repeats of self-elongation temperatures.

The disclosed method converts dsDNA into ssDNA, and performs intramolecular elongation to distribute or relocate the barcode to different parts of the sequence. Elongation can be performed in a sequence specific manner using specific known sequences within the nucleic acid molecule, or in a sequence independent manner using random sequences for intramolecular priming. In some embodiments, elongation can be performed using a combination of sequence specific and a sequence independent manner. In some embodiments, intramolecular elongation can be performed on full length ssDNA molecules or ssDNA molecules that have previously been truncated to shorter fragments. Even without prior truncation of the ssDNA molecule, the sequence coverage of the ssDNA molecule can span the entire length of the molecule or only the select regions of interests.

In a sequence-independent self-elongation step, at random loci, the ssDNA molecules can be extended using a polymerase to form a partially double-stranded structure from the original ssDNA molecule, In some embodiments the ssDNA can be prepared for intramolecular elongation from the tagged dsDNA by subjecting the dsDNA to heat denaturation under dilute conditions. Since the concentration of the molecules can be low, intramolecular annealing and elongation can be more efficient than intermolecular annealing (i.e., two complementary strands annealing back together), thereby rendering each strand of DNA from the dsDNA effectively single-stranded.

In some embodiments, annealing of the elongation sequence to a portion of the nucleic acid sequence in a nucleic acid molecule generates a partially-duplexed nucleic acid strand. In some embodiments, the partially-duplexed nucleic acid strand comprises a 5' portion comprising a single-stranded region and a 3' portion comprising the elongation sequence in an intramolecular duplex with the portion of the nucleic acid sequence. In some embodiments, the disclosed method extends the elongation sequence with a polymerase using the 5' portion of the partially-duplexed nucleic acid as a template, generating an extended nucleic acid. In some embodiments, the nucleic acid strand can be a single-stranded nucleic acid. In some embodiments, the nucleic acid can be a double-stranded nucleic acid. In some embodiments, a 3' end of the nucleic acid strand comprises the first adaptor. In some embodiments, a 3' end of the first adaptor comprises the elongation sequence.

In some embodiments, the extended nucleic acid comprises a stem-loop structure. In some embodiments, the stem-loop structure comprises a hybridized region and an unhybridized region. The hybridized region can comprise a first strand and a second strand. The first strand can comprises a 5' end or 5' portion of the extended nucleic acid. The second strand can comprise a 3' end or a 3' portion of the extended nucleic acid. The unhybridized region can be 3' to the first strand. The unhybridized region can comprise a 3' end with a second portion of the adaptor. The second portion can comprise the molecular barcode.

The stem-loop nucleic acid can comprise DNA, cDNA, or genomic DNA, or can be generated from RNA through reverse transcription. In some embodiments, the stem-loop nucleic acid can be generated from genomic DNA, a cell-free nuclei acid, a nucleic acid from a cell, a biological sample, or a cell-free sample. In some embodiments, the barcode of the stem-loop nucleotide can comprise a random sequence. In some embodiments, the hybridized region of the stem-loop structure has a length of from about 100 bp, about 200 bp, about 300 bp, about 400 bp, to about 500 bp. In some embodiments, the hybridized region of the stem-loop structure has a length from about 400 bp to about 500 bp.

In some embodiments, evenness of the self-elongation reaction using a random sequence can be achieved by the length of the random nucleic acid sequence and by the GC content of the random sequence. In some embodiments, the random sequence has a specific average GC content on each molecule-specific terminal adaptor. In some embodiments, the random sequence has an average GC content on each molecule-specific terminal adaptor of about 20%, 25%, 30%, 35%, 40%, 45%, 50%, 55%, 60%, 65%, 70%, 75%, or 80%. In some embodiments, the random sequence comprises different GC content percentages on each molecule-specific terminal adaptor. In some cases, a random sequence can comprise two or more (e.g., 2, 3, 4, 5, 6, 7, 8, 9, 10 or more) regions having different GC content percentages, such that the sequence is a blend of multiple random sequences with each sequence having a different GC content. In some embodiments, the random sequence comprises GC content percentages that can be a blend of 30% and 60%, blend of 30% and 70%, blend of 35% and 55%, blend of 35% and 60%, blend of 40% and 55%, blend of 40% and 60%, blend of 40% and 65%, blend of 50% and 65%, or blend of 50% and 70%.

Complete intramolecular nucleic acid elongation can extend the 3' end of the nucleic acid molecule. In some embodiments, the 3' extended portion comprises a length of about 100 bp, about 200 bp, about 300 bp, about 400 bp, or about 500 bp. In some embodiments, the 3' extended portion generated by elongation comprises a length of about 100 bp to about 400 bp. In some embodiments, the 3' extended portion generated by elongation comprises about 400 bp to about 500 bp.

In some embodiments, the 3' extended portion can have a length of about 75 bp to about 1,000 bp. In some embodiments, the 3' extended portion can have a length of at least about 75 bp. In some embodiments, the 3' extended portion can have a length of at most about 1,000 bp. In some embodiments, the 3' extended portion can have a length of about 75 bp to about 100 bp, about 75 bp to about 200 bp, about 75 bp to about 250 bp, about 75 bp to about 300 bp, about 75 bp to about 350 bp, about 75 bp to about 400 bp, about 75 bp to about 450 bp, about 75 bp to about 500 bp, about 75 bp to about 600 bp, about 75 bp to about 700 bp, about 75 bp to about 1,000 bp, about 100 bp to about 200 bp, about 100 bp to about 250 bp, about 100 bp to about 300 bp, about 100 bp to about 350 bp, about 100 bp to about 400 bp, about 100 bp to about 450 bp, about 100 bp to about 500 bp, about 100 bp to about 600 bp, about 100 bp to about 700 bp, about 100 bp to about 1,000 bp, about 200 bp to about 250 bp, about 200 bp to about 300 bp, about 200 bp to about 350 bp, about 200 bp to about 400 bp, about 200 bp to about 450 bp, about 200 bp to about 500 bp, about 200 bp to about 600 bp, about 200 bp to about 700 bp, about 200 bp to about 1,000 bp, about 250 bp to about 300 bp, about 250 bp to about 350 bp, about 250 bp to about 400 bp, about 250 bp to about 450 bp, about 250 bp to about 500 bp, about 250 bp to about 600 bp, about 250 bp to about 700 bp, about 250 bp to about 1,000 bp, about 300 bp to about 350 bp, about 300 bp to about 400 bp, about 300 bp to about 450 bp, about 300 bp to about 500 bp, about 300 bp to about 600 bp, about 300 bp to about 700 bp, about 300 bp to about 1,000 bp, about 350 bp to about 400 bp, about 350 bp to about 450 bp, about 350 bp to about 500 bp, about 350 bp to about 600 bp, about 350 bp to about 700 bp, about 350 bp to about 1,000 bp, about 400 bp to about 450 bp, about 400 bp to about 500 bp, about 400 bp to about 600 bp, about 400 bp to about 700 bp, about 400 bp to about 1,000 bp, about 450 bp to about 500 bp, about 450 bp to about 600 bp, about 450 bp to about 700 bp, about 450 bp to about 1,000 bp, about 500 bp to about 600 bp, about 500 bp to about 700 bp, about 500 bp to about 1,000 bp, about 600 bp to about 700 bp, about 600 bp to about 1,000 bp, or about 700 bp to about 1,000 bp. In some embodiments, the 3' extended portion can have a length of about 75 bp, about 100 bp, about 200 bp, about 250 bp, about 300 bp, about 350 bp, about 400 bp, about 450 bp, about 500 bp, about 600 bp, about 700 bp, or about 1,000 bp.

In some embodiments, the library can be optionally degraded into small fragments as ssDNA or dsDNA prior to the elongation step. In some embodiments, the elongation step can be performed on full length nucleic acid molecules. In some embodiments, the length of nucleic acid synthesized during the intramolecular elongation step can be optionally limited to approximately the read length of NGS. In some embodiments, intramolecular elongation can be accomplished using low nucleic acid concentrations, which favors intramolecular elongation over inter molecular ligation.

In some embodiments, the tagged and amplified nucleic acid molecules can be fragmented, wherein each fragment has a different length. In some embodiments, the tagged and amplified nucleic acid molecules can be fragmented using enzymatic fragmentation methods, sonication-based fragmentation, acoustic shearing, nebulization, needle shearing, French pressure cells, or any combination thereof. In some embodiments, the nucleic acid fragments obtained can be tagged at the 5' end or at their 3' end. In some embodiments, the nucleic acid molecules can be fragmented into two or more fragment and can be devoid of tags.

In some embodiments, the disclosed method involves fragmentation of the terminally barcoded and amplified nucleic acid mixture prior to intramolecular elongation. In some embodiments the method involves using a polymerase to intramolecularly anneal and extend the self-elongation sequence and generate a pool of uniquely barcoded nucleic acid molecules of varying lengths. In some embodiments, the uniquely barcoded dsDNA can be fragmented. The method may further comprise obtaining sequence information from the uniquely barcoded dsDNA molecules of varying lengths using a standard NGS library preparation.

In some embodiments, the method comprises (i) using a polymerase for intramolecular elongation of the self-elongation sequence to loci throughout the parental long nucleic acid molecule to be sequenced, and to generate a pool of uniquely barcoded dsDNA of varying lengths; (ii) amplifying the elongated product by utilizing primers that contain the second sequencing adaptors and target-specific sequences that can be complementary to the sequence downstream of the elongation loci; and (iii) obtaining sequence information from the uniquely barcoded dsDNA molecules of varying lengths using a standard NGS library preparation.

In some embodiments, the method comprises (i) using a polymerase to elongate the primer to loci throughout the parental long nucleic acid molecule to be sequenced and/or to amplify the mixture to produce a mixture of uniquely barcoded dsDNA molecules of varying lengths; (ii) fragmenting the uniquely barcoded dsDNA; (iii) ligating adaptors to the fragmented dsDNA; and (iv) obtaining sequence information from the uniquely barcoded nucleic acid molecules of varying lengths.

In some embodiments, the method comprises (i) using a polymerase to intramolecularly elongate the self-elongation sequence to loci throughout the parental long nucleic acid molecule to be sequenced and generate a pool of uniquely barcoded dsDNA molecules of varying lengths; (ii) fragmenting the uniquely barcoded dsDNA; (iii) ligating adaptors to the fragmented dsDNA; and (iv) obtaining sequence information from the uniquely barcoded dsDNA molecules of varying lengths using a standard NGS library preparation.

Figure 14:
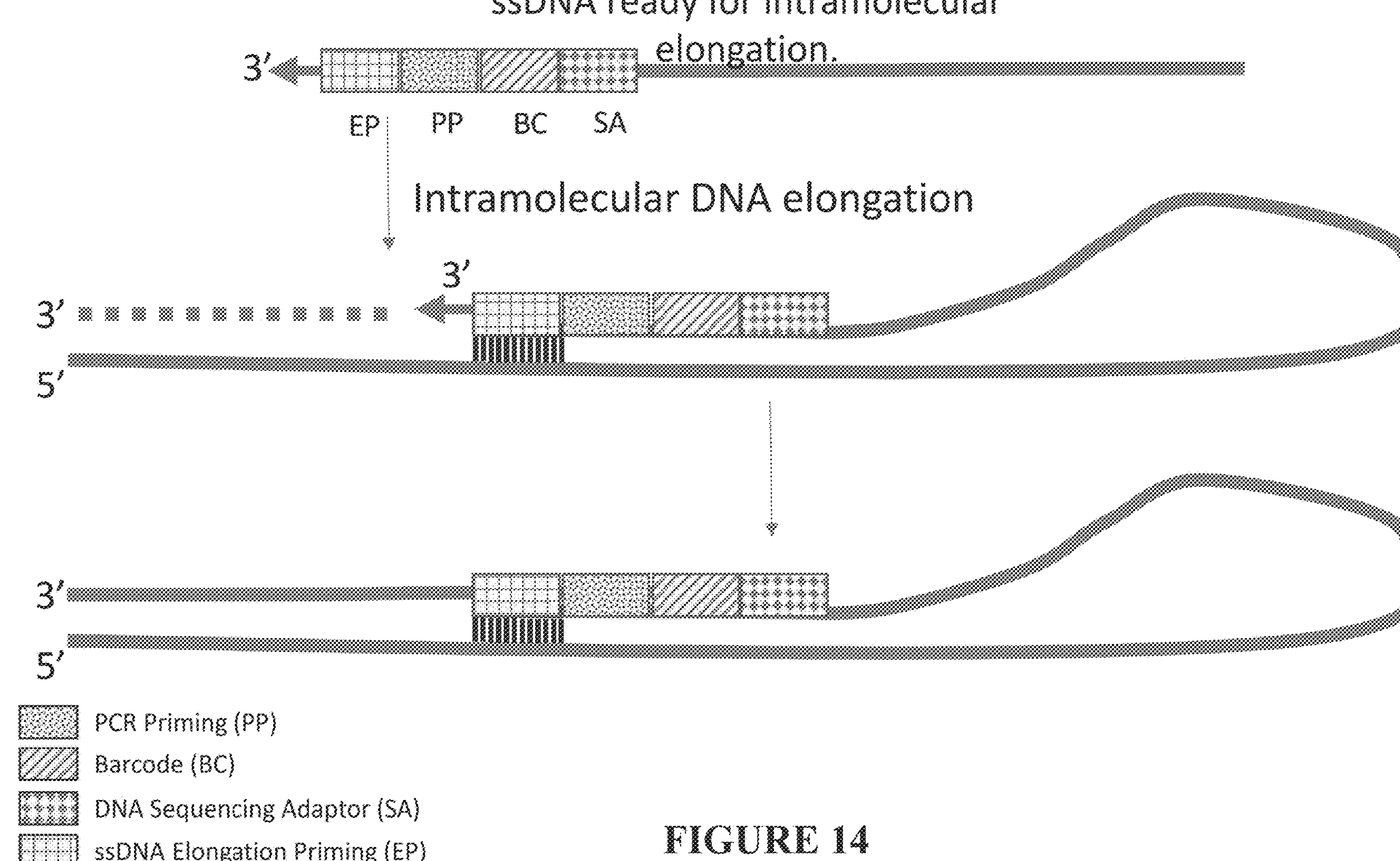
FIG. 14 shows an illustrative scheme for intramolecular elongation of a single-stranded nucleic acid molecule. The elongation can be complete or partial.

FIG. 14 illustrates intramolecular elongation of an ssDNA molecule. Intramolecular elongation can be complete or partial. In some aspects, intramolecular elongation can be complete.

FIG. 15 illustrates limiting ssDNA to NGS read length through limited intramolecular ssDNA elongation and subsequent DNA blunting.

In some embodiments, the fragmented DNA can be blunted. Blunt ends can be generated using a single strand-specific DNA exonuclease, such as exonuclease I, exonuclease VII, or a combination thereof, to degrade overhanging single stranded ends. In some embodiments, blunt ends can be generated using a single strand-specific DNA endonuclease, such as mung bean endonuclease or S1 endonuclease. In some embodiments, blunt ends can be generated using a polymerase that comprises single stranded exonuclease activity, such as T4 DNA polymerase, any other polymerase comprising single stranded exonuclease activity, or a combination thereof, to degrade the overhanging single stranded ends.

In some embodiments, blunted DNA can be 5' phosphorylated using T4 polynucleotide kinase; the 5' phosphorylation can be important for subsequent intramolecular ligation of the tagged DNA fragments. In some embodiments, blunted DNA can be 5' phosphorylated by incorporating dUTP in the terminal adaptors used to uniquely tag and amplify DNA molecules. The 5' phosphorylation site can be generated using a combination of uracil-DNA glycosylase and an endonuclease to hydrolyze the apurinic/apyrimidinic sites.

In some embodiments, the PCR primer extension after intramolecular elongation, or enrichment PCR, can occur in parallel reactions. In some embodiments, enrichment PCR occurs in multiple PCR reactions, wherein each reaction has a different primer composition. In some embodiments, enrichment PCR occurs in a multiplexed reaction, wherein PCR reactions occur with multiple primers in the same reaction.

In some embodiments, the enrichment PCR includes multiple primers (i.e. a multiplexed reaction), wherein each primer has a different target sequence that can be complementary to the sequence downstream of an elongation locus and a universal sequencing adaptor.

In some embodiments, enrichment PCR can be performed as a multiplexed reaction using primers with different target sequences, and the amplified elongation products contain one or more products from all the target sequences downstream of each elongation locus. Collectively, the elongation products represent from one or more combinations of elongation loci and target sequences downstream of each elongation locus. In some embodiments, the distance between the elongation locus and a target sequence in the enrichment PCR can be approximately one read-length apart. In some embodiments, the distance between the elongation locus and a target sequence in the enrichment PCR can be approximately 100 bp, 150 bp, 200 bp, 250 bp, 300 bp, 350 bp, 400 bp, 450 bp, or 500 bp apart.

The distance between an elongation locus and a target sequence in the enrichment PCR can be about 75 bp to about 1,000 bp. The distance between an elongation locus and a target sequence in the enrichment PCR can be at least about 75 bp. The distance between an elongation locus and a target sequence in the enrichment PCR can be at most about 1,000 bp. The distance between an elongation locus and a target sequence in the enrichment PCR can be at most about 1,000 bp. The distance between an elongation locus and a target sequence in the enrichment PCR can be about 75 bp to about 100 bp, about 75 bp to about 200 bp, about 75 bp to about 250 bp, about 75 bp to about 300 bp, about 75 bp to about 350 bp, about 75 bp to about 400 bp, about 75 bp to about 450 bp, about 75 bp to about 500 bp, about 75 bp to about 600 bp, about 75 bp to about 700 bp, about 75 bp to about 1,000 bp, about 100 bp to about 200 bp, about 100 bp to about 250 bp, about 100 bp to about 300 bp, about 100 bp to about 350 bp, about 100 bp to about 400 bp, about 100 bp to about 450 bp, about 100 bp to about 500 bp, about 100 bp to about 600 bp, about 100 bp to about 700 bp, about 100 bp to about 1,000 bp, about 200 bp to about 250 bp, about 200 bp to about 300 bp, about 200 bp to about 350 bp, about 200 bp to about 400 bp, about 200 bp to about 450 bp, about 200 bp to about 500 bp, about 200 bp to about 600 bp, about 200 bp to about 700 bp, about 200 bp to about 1,000 bp, about 250 bp to about 300 bp, about 250 bp to about 350 bp, about 250 bp to about 400 bp, about 250 bp to about 450 bp, about 250 bp to about 500 bp, about 250 bp to about 600 bp, about 250 bp to about 700 bp, about 250 bp to about 1,000 bp, about 300 bp to about 350 bp, about 300 bp to about 400 bp, about 300 bp to about 450 bp, about 300 bp to about 500 bp, about 300 bp to about 600 bp, about 300 bp to about 700 bp, about 300 bp to about 1,000 bp, about 350 bp to about 400 bp, about 350 bp to about 450 bp, about 350 bp to about 500 bp, about 350 bp to about 600 bp, about 350 bp to about 700 bp, about 350 bp to about 1,000 bp, about 400 bp to about 450 bp, about 400 bp to about 500 bp, about 400 bp to about 600 bp, about 400 bp to about 700 bp, about 400 bp to about 1,000 bp, about 450 bp to about 500 bp, about 450 bp to about 600 bp, about 450 bp to about 700 bp, about 450 bp to about 1,000 bp, about 500 bp to about 600 bp, about 500 bp to about 700 bp, about 500 bp to about 1,000 bp, about 600 bp to about 700 bp, about 600 bp to about 1,000 bp, or about 700 bp to about 1,000 bp. The distance between an elongation locus and a target sequence in the enrichment PCR can be about 75 bp, about 100 bp, about 200 bp, about 250 bp, about 300 bp, about 350 bp, about 400 bp, about 450 bp, about 500 bp, about 600 bp, about 700 bp, or about 1,000 bp.

In some embodiments, when the enrichment PCR can be performed as a multiplexed reaction, the loci used for intramolecular elongation can be different from the target sequences used in the enrichment PCR. In some embodiments, when the enrichment PCR can be performed as a multiplexed reaction, the distance between any elongation locus and any downstream target sequence can be at least 10 bp, 15 bp, 20 bp, 25 bp, 30 bp, 35 bp, 40 bp, 45 bp, or 50 bp apart. In some embodiments, when the enrichment PCR can be performed as a multiplexed reaction, the distance between any elongation locus and any downstream target sequence can be at least 50 bp, 55 bp, 60 bp, 65 bp, 70 bp, 75 bp, 80 bp, 85 bp, 90 bp, 95 bp, or 100 bp apart.

The distance between an elongation locus and a downstream target sequence can be about 10 bp to about 100 bp. The distance between an elongation locus and a downstream target sequence can be at least about 10 bp. The distance between an elongation locus and a downstream target sequence can be at most about 100 bp. The distance between an elongation locus and a downstream target sequence can be about 10 bp to about 20 bp, about 10 bp to about 30 bp, about 10 bp to about 40 bp, about 10 bp to about 50 bp, about 10 bp to about 60 bp, about 10 bp to about 70 bp, about 10 bp to about 80 bp, about 10 bp to about 90 bp, about 10 bp to about 100 bp, about 20 bp to about 30 bp, about 20 bp to about 40 bp, about 20 bp to about 50 bp, about 20 bp to about 60 bp, about 20 bp to about 70 bp, about 20 bp to about 80 bp, about 20 bp to about 90 bp, about 20 bp to about 100 bp, about 30 bp to about 40 bp, about 30 bp to about 50 bp, about 30 bp to about 60 bp, about 30 bp to about 70 bp, about 30 bp to about 80 bp, about 30 bp to about 90 bp, about 30 bp to about 100 bp, about 40 bp to about 50 bp, about 40 bp to about 60 bp, about 40 bp to about 70 bp, about 40 bp to about 80 bp, about 40 bp to about 90 bp, about 40 bp to about 100 bp, about 50 bp to about 60 bp, about 50 bp to about 70 bp, about 50 bp to about 80 bp, about 50 bp to about 90 bp, about 50 bp to about 100 bp, about 60 bp to about 70 bp, about 60 bp to about 80 bp, about 60 bp to about 90 bp, about 60 bp to about 100 bp, about 70 bp to about 80 bp, about 70 bp to about 90 bp, about 70 bp to about 100 bp, about 80 bp to about 90 bp, about 80 bp to about 100 bp, or about 90 bp to about 100 bp. The distance between an elongation locus and a downstream target sequence can be about 10 bp, about 20 bp, about 30 bp, about 40 bp, about 50 bp, about 60 bp, about 70 bp, about 80 bp, about 90 bp, or about 100 bp.

In some embodiments, the disclosed method further comprises overlapping PCR reactions that span the full-length of the molecule. In some embodiments, the disclosed method further comprises overlapping PCR reactions containing NGS adaptors. In some embodiments, the method further comprises overlapping PCR reactions that each equally cover the full-length molecule, thereby reducing coverage bias. In some embodiments, the method further comprises overlapping PCR reactions that provide coverage of specific regions of interest, thereby reducing the overall sequencing cost by eliminating regions of known sequence from the sequencing library. In some embodiments, the method further comprises overlapping PCR reactions that extend beyond the PCR primer regions such that the primer binding region can be sequenced from the natural template and not from the primer.

In some embodiments, the self-elongated nucleic acid molecules can be prepared for sequencing using a set of padlock probes that collectively span and cover the length of the nucleic acid to be sequenced. In some embodiments, the padlock probes have 5' terminal arms complementary to the region of interest primer (ROIP) on the ssDNA. In some embodiments, the 3' arms of the padlock probes can be approximately one read-length (100 bp-400 bp) apart. In some embodiments, the 3' terminal arm complementary to regions within the ssDNA can be approximately one read-length apart from the 5' terminal arm. In some embodiments, each padlock probe copies both the barcode information within each ssDNA and the sequence of interest via elongation.

In some embodiments, the padlock probe comprises a 5' end and a 3' end connected by a linker sequence. In some embodiments, the 3' end of the padlock probe can be extended to generate an extended nucleic acid comprising the padlock probe and a sequence complementary to the portion of a nucleic acid sequence. In some embodiments, the 5' end and a 3' end of the extended nucleic acid comprising the padlock probe and the sequence complementary to the portion of the nuclei acid sequence can be ligated, generating a circularized nucleic acid comprising the padlock probe and the complementary sequence. In some embodiments, the circularized nucleic acid can be amplified, generating linearized nucleic acids comprising a molecular barcode and a sequence complementary to a sequencing primer. Amplification can be performed using standard techniques, such as PCR. In some embodiments, the linearized nucleic acids can be sequenced using methods, such as massively parallel sequencing, to generate sequencing leads for phasing.

In some embodiments, each padlock probe copies the primer sequence for NGS sequencing on the ssDNA via elongation. In some embodiments, each padlock probe contains universal nucleic acid sequencing adaptors that prime a padlock library for downstream PCR using universal primers. In some embodiments, after the nucleic acid sequences on ssDNA can be copied, and each padlock probe can be circularized via intramolecular ligation. In some embodiments, the padlock probes can be prepared for next generation sequencing (NGS) using PCR with two universal primers.

Figure 34:
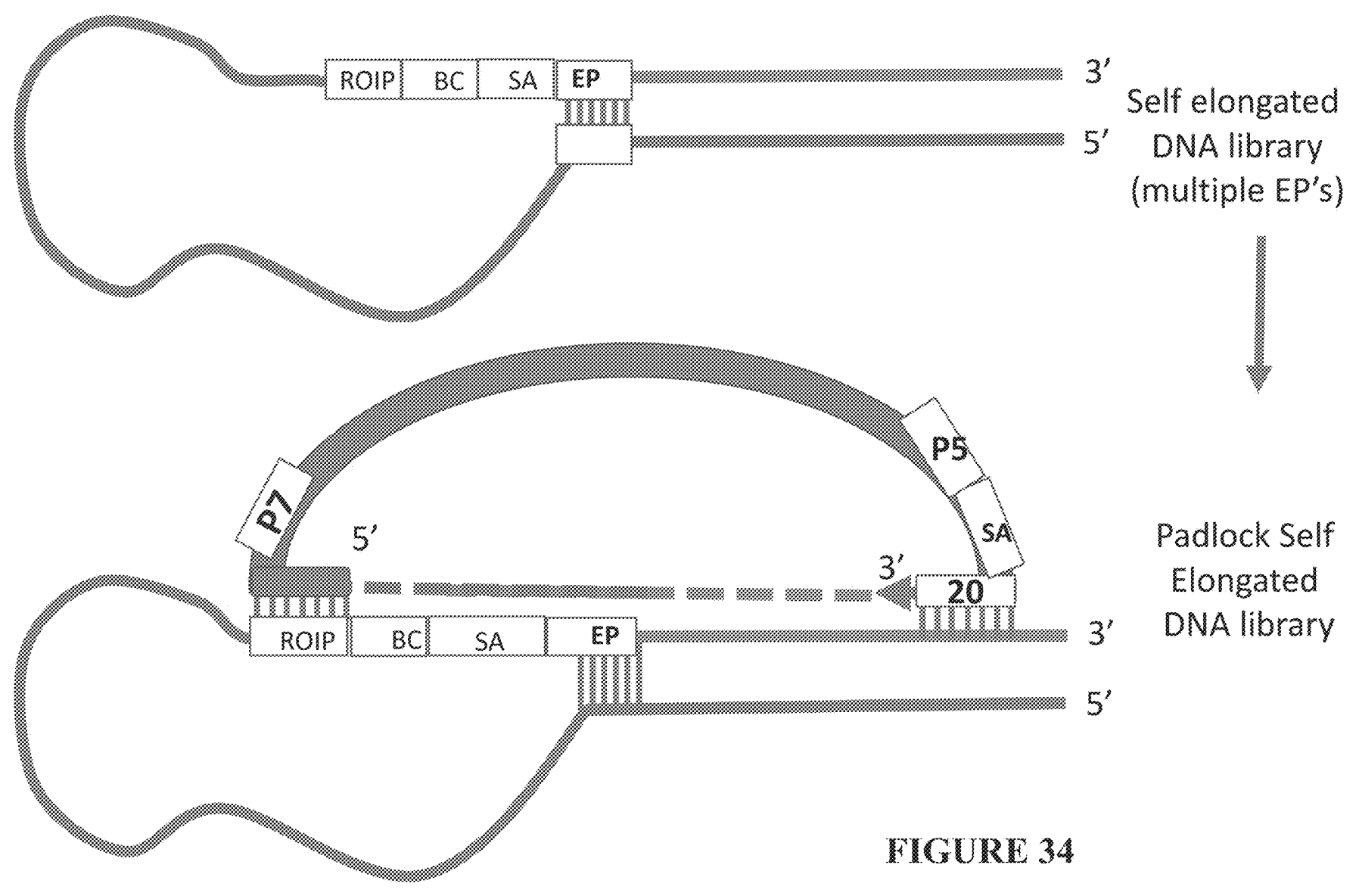

FIG. 34 illustrates how the padlock molecules probe the self-elongated ssDNA with one arm complementary to the ROIP segment, and the other arm complementary to a segment within the self-elongated nucleic acid molecule. The padlock probes elongate from their 3' termini to their 5' termini. When the elongating 3' termini of the padlock probe reach the 5' of the padlock probes the 5' and 3' ends can be ligated using a DNA ligase and the padlock probe molecule can be circularized.

Figure 35:
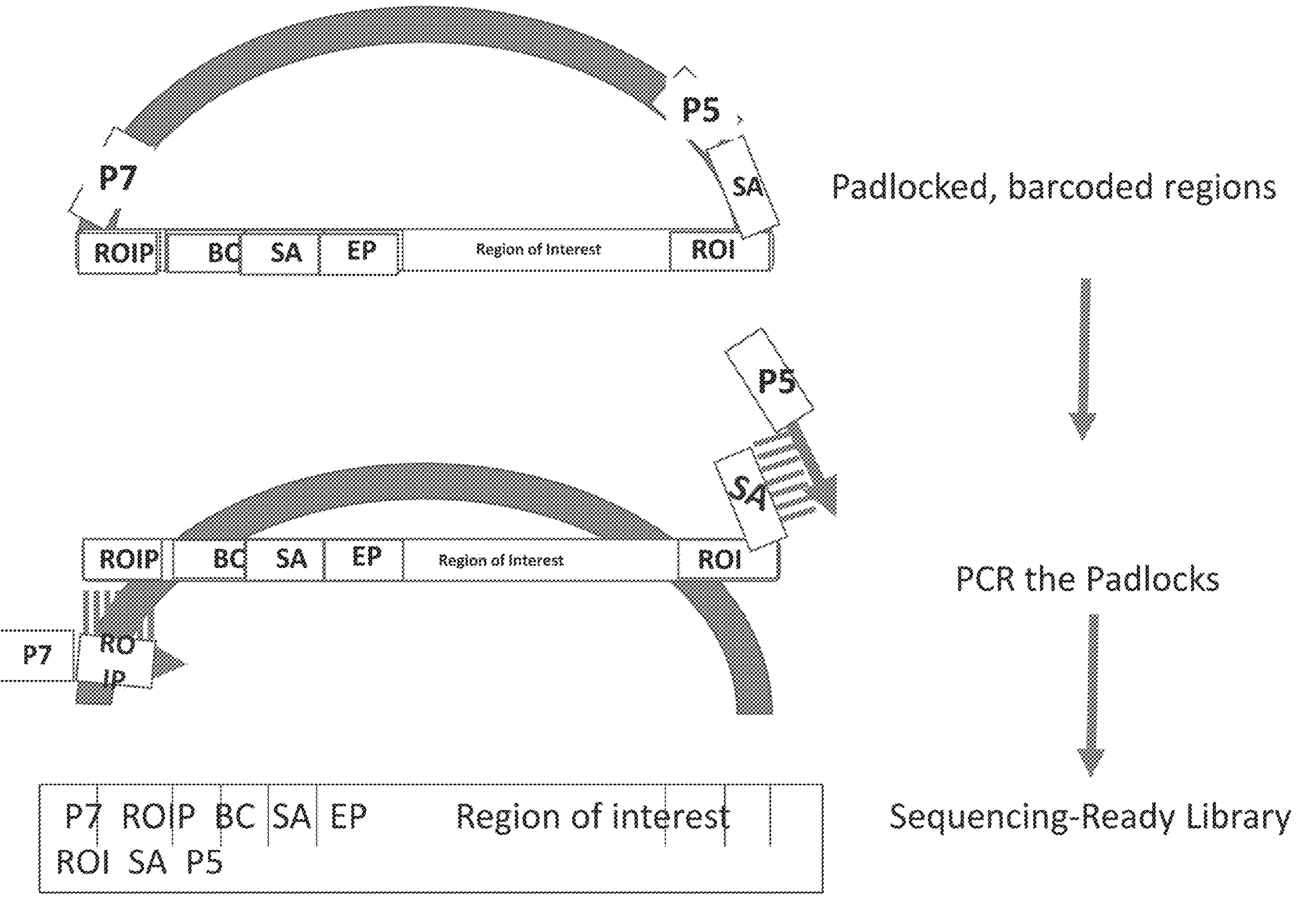
FIG. 35 shows an illustrative scheme for generating sequencing-ready library from padlocked barcoded nucleic acids using P5 and P7 adaptor primers.
Figure 36:
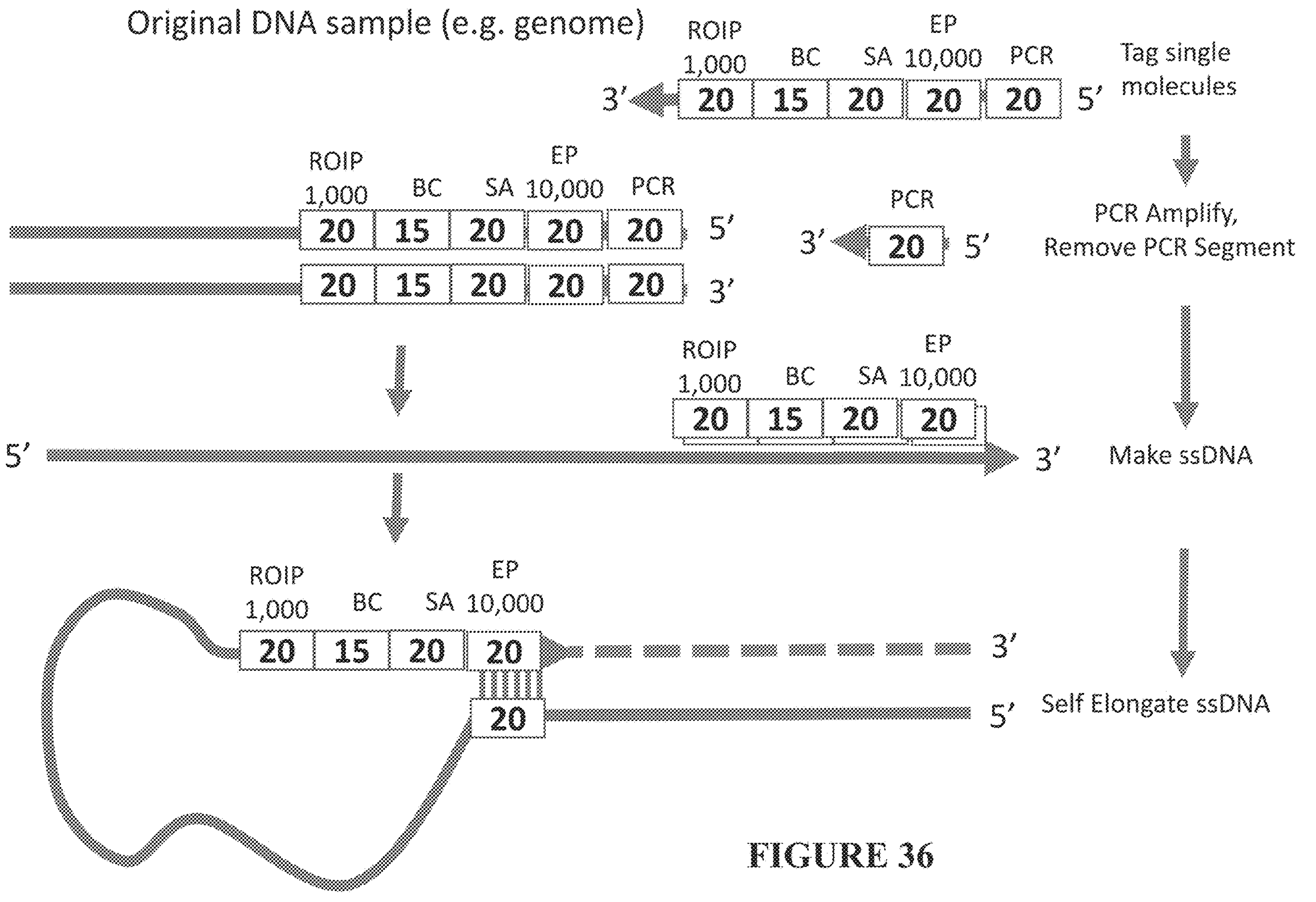
FIG. 36 illustrates how the schemes presented in FIGS. 32-35 can be performed in multiplex for many different molecules, for example, by synthesizing the EP and ROIP segments as a pooled library in which each ROIP has several EP segments that evenly cover the gene amplified by the ROIP segment.

FIG. 35 illustrates how the padlock circularized padlock probes can be PCR amplified using P5 and P7 adaptor primers to generate sequencing ready PCR amplicons.

According to some embodiments, the intramolecularly elongated fragments can generate a library of elongated nucleic acid molecules, wherein each elongated nucleic acid can be of a different size. Since each of the amplified and the uniquely tagged nucleic acid molecules can be fragmented differently, the intramolecular elongation generates copies of the nucleic acid, each copy having the 5' or 3' barcode tag at different positions along the molecule. The barcode tag can be indicative of the molecular origin of the fragment.

F. Step 4: Integration of NGS Adaptors and Size Selection

The intramolecularly elongated library can then be prepared for NGS using standard NGS library preparation.

Step 4a: Sequence-Independent Ligation of NGS Adaptors

In some embodiments, sequence independent tagging can be performed using sequence-independent ligation. In some embodiments, sequence-independent ligation can occur by blunt-end ligation, sticky-end ligation, or TA-ligation. Ligation reactions can include DNA ligases such as DNA ligase I, DNA ligase III, DNA ligase IV, and T4 DNA ligase.

In some embodiments, a second sequencing adaptor can be appended to the extended nucleic acid. In some embodiments, the second sequencing adaptor can be appended by ligation or PCR. In some embodiments, PCR uses one or more oligonucleotides with a 5' portion comprising a second adaptor and a 3' portion with a sequence complementary to a 3' extended portion that was generated by intramolecular elongation. In some embodiments, the second adaptor can be appended at a 3' end of the extended nucleic acid.

In some embodiments, the extended nucleic acid appended to the second adaptor can be amplified. In some embodiments, amplification of the extended nucleic acid appended to the second adaptor can be performed using two primers, where the first primer anneals to the first adaptor or complement thereof, and the second primer anneals to the second adaptor or complement thereof. In some embodiments, the products of amplification can be sequenced to generate sequencing reads using methods, such as massively parallel sequencing. The sequencing reads can then be phased to determine the molecular origin of two or more nucleic acid sequences of interest in a mixture.

Figure 21:
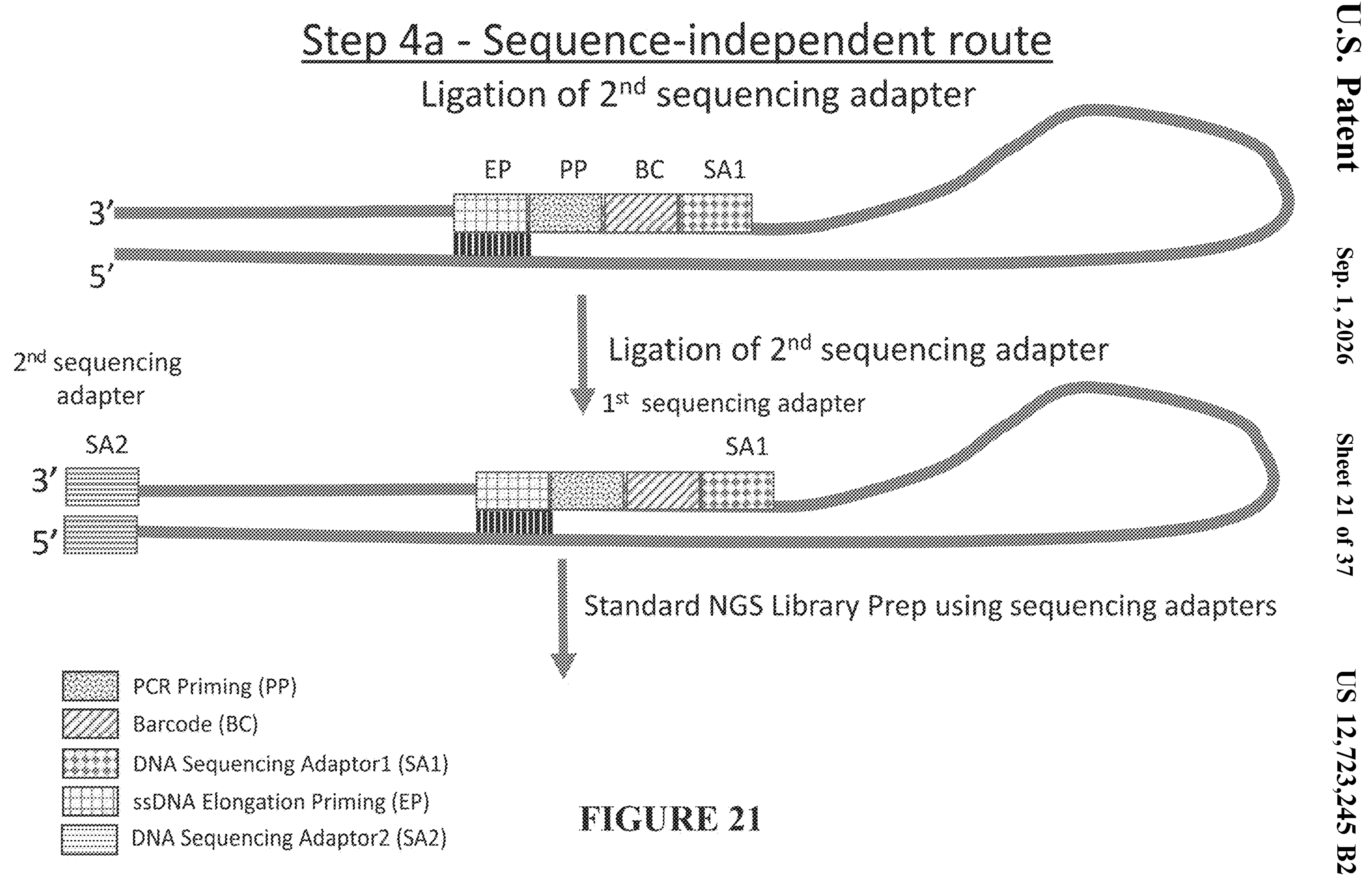
FIG. 21 shows an illustrative scheme for generating a NGS library via a sequence-independent method that can comprise appending a second sequencing adaptor using ligation.

FIG. 21 illustrates the ligation of a second sequencing adaptor in a sequence-independent method, and subsequent PCR-based NGS library preparation.

Figure 22:
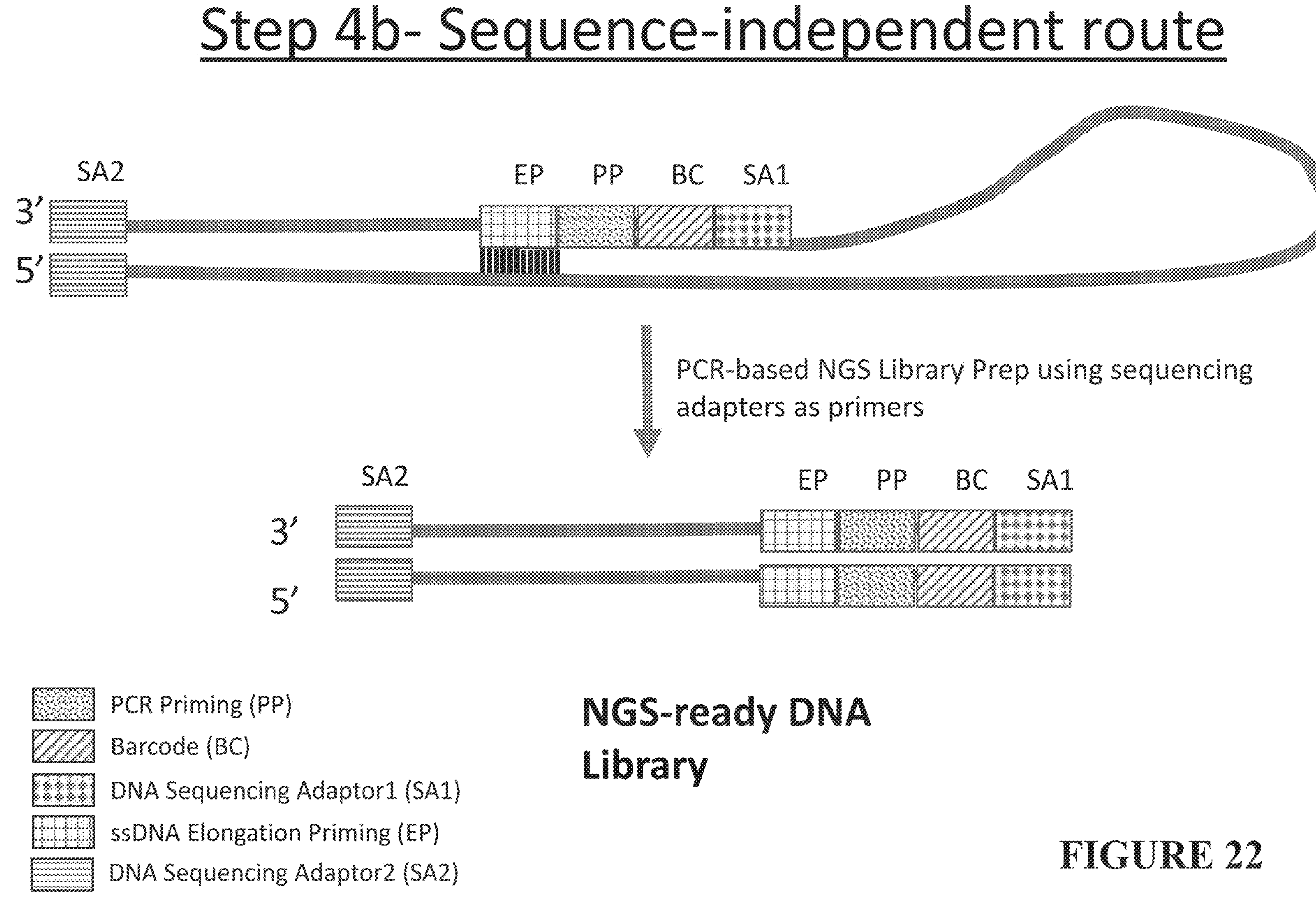
FIG. 22 shows an illustrative scheme for generating a NGS library via a sequence-independent method that can comprise amplifying a tagged nucleic acid comprising a first sequencing adaptor and a second sequencing adaptor by PCR.

FIG. 22 illustrates PCR-based NGS library preparation using sequencing adaptors as primers.

In some embodiments, sequence dependent tagging can be performed using sequence specific or partial sequence specific primers. For example, when investigating alternatively spliced transcripts, a barcode can be added specifically to the sequences of interest using a forward primer complementary to exon 1 of the transcript and a reverse primer complementary to the poly-A tail terminating all alternatively spliced transcripts. A unique barcode sequence can be added at the 3' end of each primer in the primer mixture such that the product obtained includes all alternative transcripts initiated from the specific exon 1, wherein each amplicon can be flanked by a unique barcode sequence at both ends of the molecule. In some embodiments, only the forward primer includes a barcode sequence, thereby obtaining PCR products with a unique barcode sequence only at the 5' end of the molecule.

FIG. 23 illustrates the use of sequence-specific PCR amplification to add a second sequencing adaptor to prepare an NGS library. The second sequencing adaptor can be appended using a primer comprising a sequence complimentary to a target sequence in an elongated nucleic acid (e.g., see Solid Dark Box at 3' end of PCR primer in FIG. 23). The sequence complementary to the target sequence can be a gene specific sequence. The sequence complementary to the target sequence can comprise partial, substantial, or complete complementarity to the target sequence. The sequence complementary to the target sequence can comprise a random sequence. The sequence complementary to the target sequence can be in a 3' portion or a 3' end of the primer. The second sequencing adaptor can be 5' to the sequence complementary to the target sequence in the primer.

Complementarity between two sequences can be about 10% to about 100%. Complementarity between two sequences can be at least about 10%. Complementarity between two sequences can be at most about 100%. Complementarity between two sequences can be about 10% to about 20%, about 10% to about 30%, about 10% to about 40%, about 10% to about 50%, about 10% to about 60%, about 10% to about 70%, about 10% to about 80%, about 10% to about 85%, about 10% to about 90%, about 10% to about 95%, about 10% to about 100%, about 20% to about 30%, about 20% to about 40%, about 20% to about 50%, about 20% to about 60%, about 20% to about 70%, about 20% to about 80%, about 20% to about 85%, about 20% to about 90%, about 20% to about 95%, about 20% to about 100%, about 30% to about 40%, about 30% to about 50%, about 30% to about 60%, about 30% to about 70%, about 30% to about 80%, about 30% to about 85%, about 30% to about 90%, about 30% to about 95%, about 30% to about 100%, about 40% to about 50%, about 40% to about 60%, about 40% to about 70%, about 40% to about 80%, about 40% to about 85%, about 40% to about 90%, about 40% to about 95%, about 40% to about 100%, about 50% to about 60%, about 50% to about 70%, about 50% to about 80%, about 50% to about 85%, about 50% to about 90%, about 50% to about 95%, about 50% to about 100%, about 60% to about 70%, about 60% to about 80%, about 60% to about 85%, about 60% to about 90%, about 60% to about 95%, about 60% to about 100%, about 70% to about 80%, about 70% to about 85%, about 70% to about 90%, about 70% to about 95%, about 70% to about 100%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100%. Complementarity between two sequences can be about 10%, about 20%, about 30%, about 40%, about 50%, about 60%, about 70%, about 80%, about 85%, about 90%, about 95%, or about 100%.

In some embodiments, the nucleic acid molecules were prepared for standard NGS sample preparation by shearing the nucleic acid molecules into sequences having lengths suitable for NGS. In some embodiments, the nucleic acid molecules were sheared into sequences of about 100 bp, about 110 bp, about 120 bp, about 130 bp, about 140 bp, about 150 bp, about 160 bp, about 170 bp, about 180 bp, about 190 bp, or about 200 bp. In some embodiments, the nucleic acid molecules were sheared into sequences of about 250 bp, about 300 bp, about 350 bp, or about 400 bp.

G. Phasing

In some embodiments, the disclosed method comprises phasing obtained sequences based on their molecular origin as indicated by the unique molecule-specific barcode.

In some embodiments, the short-read sequencing information can be clustered using molecule-specific tags and assembled into de novo sequences. The resulting sequences can be phased reconstruction to identify the original long nucleic acid molecules, and may share any degree of homology or similarity with each other. By comparing long sequences that can be identical or share any commonality in their classification with each other, the present method allows quantitative analysis by estimating the abundance of different molecules in the pool of parental long molecules.

In some embodiments, the barcoded NGS short reads constructed from the elongated library provide sequence coverage for the entire length of the long nucleic acid molecule, and generates contiguous synthetic long reads for phasing. In some embodiments, the barcoded NGS short reads constructed from the elongated library cover regions of interests that can be separated by homologous regions, and generate discontiguous synthetic long reads for phasing.

The ligated nucleic acid molecules can optionally be amplified using PCR technologies and/or sheared into fragments suitable for NGS. In some embodiments, the sequence may be de-novo assembled and phased based on the unique barcode sequence indicative of a molecule's molecular origin. In some embodiments, short-read sequences can be clustered into consensus sequences based on their unique barcode sequences, and the consensus sequences can be subsequently used for reference mapping and phasing.

Some fragments resulting from the shearing of the DNAs may "lose" their tags. However, because there can be multiple copies of each amplicon and each amplicon can be fragmented into a different size and can be self-ligated, the barcode can be inserted into different locations along the length of the original nucleic acid molecule allowing for phasing of the original nucleic acid molecule's sequence.

To determine that a fragment with a 3' tag has the same molecular origin as another fragment having a 5' tag that can be different from the 3' tag, pairing of 5' tags and 3' tags may be necessary. In some embodiments, a 5' prime tagged fragment may be paired to its 3' tagged fragment based on intramolecular ligation of unfragmented tagged nucleic acid molecules. In some embodiments, a sample of the amplified tagged nucleic acid molecules can be set aside and intramolecularly ligated such that the 5' barcode ligates with the 3' barcode. Then, the sample can be sequenced to identify the barcode pairs. In some embodiments, the 5' tag and the 3' tag can be paired by including an elongation reaction that initiates from one end and elongate near the other end, such that the tag information can be obtained within the same sequencing short read.

Phasing the entire length of a parent long molecule can be achieved with short-read information that collectively spans the entire length of the parent long molecule. Such short-read information can be represented as the coverage completeness of the long molecule or as the percent reference sequence coverage. Short-read information can be dictated by both short-read sequencing depth and coverage evenness at different locations on the parent long molecule. Coverage evenness can be determined by computing the coefficient of variance in the sequencing depth between each location on the parent long molecule.

In some embodiments, a phased sequence can be utilized to determine the expression of previously unidentified alternative transcripts, for quality control of synthesized long nucleic acid molecules, for identifying the length of repetitive sequences and the like.

Kits

The present disclosure also provides kits. The kits include one or more compounds or reagents of the disclosure as described elsewhere herein, in packaging, and written material that can include instructions for use, discussion of clinical studies, listing of side effects, and the like.

In some embodiments, kits comprise an oligonucleotide comprising a) a barcode; and b) an elongation sequence, wherein the elongation sequence or a complement thereof can be configured to intramolecularly anneal to a first region of a nucleic acid strand upon appending the oligonucleotide to the nucleic acid strand. In some embodiments, a reverse complement of the elongation sequence provided in the kit can be configured to intramolecularly anneal to the first region of the nucleic acid strand upon appending the oligonucleotide to the nucleic acid strand. In some embodiments, the elongation sequence can be at the 5' end of the oligonucleotide. In some embodiments, the oligonucleotide further comprises a sequence complementary to at least a portion of a second region of the nucleic acid strand. In some embodiments, the sequence complementary to the at least a portion of the second region can be at a 3' end of the oligonucleotide. In some embodiments, the barcode comprises a random sequence. In some embodiments, the elongation sequence comprises a random sequence. In some embodiments, the elongation sequence comprises a sequence complementary to the first region of the nucleic acid strands.

A kit of the disclosure can comprise one or more enzymes. Non-limiting examples of enzymes include polymerases, ligases, exonucleases, endonucleases and end repair enzymes.

A kit can comprise instructions, software, or both for transforming sequencing reads, for example, short read data into long read data. A kit can comprise instructions, software, or both for determining phase information from sequencing reads.

Kits of the present disclosure may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials.

In some embodiments, the compounds and reagents of the present disclosure can be provided as separate compositions in separate containers within the kit. In some embodiments, the compound of the present disclosure and the agent can be provided as a single composition within a container in the kit.

Suitable packaging and additional articles for use (e.g., measuring cup for liquid preparations, foil wrapping to minimize exposure to air, and the like) may be included in the kit. Kits described herein can be provided, marketed and/or promoted to health providers, including physicians, nurses, pharmacists, formulary officials, and the like. Kits may also, in some embodiments, be marketed directly to the consumer.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: Sequence-Independent Tagging of Nucleic Acid in Complex Mixtures

First, a complex mixture of DNA/RNA molecules of varying lengths was obtained. When the starting material included RNA, the RNA molecules were converted to DNA. DNA that was reverse-transcribed from RNA was tagged during the reverse transcription step, or after the RNA was reverse transcribed into cDNA. Each DNA molecule in the mixture was tagged using a unique terminal adaptor comprising 1) a molecular barcode that acted as a unique molecular identifier, and 2) a self-elongation sequence.

The DNA molecules were then amplified to generate multiple copies of each barcoded DNA molecule. In some instances, the self-elongation sequence was appended during the tagging phase or the amplification phase. The mixture of DNA molecules were tagged such that each DNA molecule in the mixture received a unique tag. The DNA molecules were tagged with unique barcodes by mixing the DNA molecules with an excess amount of unique barcode sequences comprising 6-20 random bp sequences and subsequently attaching the unique barcode sequence to each of the DNA molecules using blunt end ligation.

In some experiments, a mixture of DNA molecules was uniquely tagged with similar barcodes using a primer driven elongation reaction, or the barcodes were integrated into the molecules of the library from the outset if the library can be synthetically assembled using DNA synthesis technology. If the barcode was integrated into the molecules of the library during DNA synthesis, the barcode comprises random sequences or a collection of known sequences that were equal or larger in number than the number of unique DNA molecules synthesized. The self-elongation sequence of the unique terminal adaptor at the 3'-end comprises a sequence selected from a target-specific sequence or a random self-elongation sequence. A final mixture of uniquely barcoded DNA molecules was then obtained.

The tagged dsDNA molecules were converted into ssDNA molecules by degrading or removing one strand of the uniquely barcoded DNA molecules to obtain a pool of uniquely barcoded and elongation-primed ssDNA molecules. When the elongation sequence at the termini provided a random and self-complementary (intramolecular) DNA sequence, polymerization (elongation) was initiated at various loci at which the random elongation sequence primed the elongation process. Each random 3' terminus primed a single elongation reaction. The collection of random 3' termini on different molecules primed self-elongation reactions throughout many loci spread along the sequence of ssDNA.

In a sequence-independent self-elongation step, at random loci, the ssDNA molecules were extended using a polymerase to form a partially double-stranded structure from the original ssDNA molecule.

The length and the composition of the randomer sequence used for intramolecular elongation was found to impact the coverage evenness and coverage completeness of the originally tagged parent long molecule.

FIG. 16 demonstrates results of studies performed to understand the impact of polymerase and randomer length on coverage evenness. In FIG. 16, coefficient of variance (CV) is used as a metric for variation in coverage evenness of long molecules by short reads. FIG. 16 demonstrates that an elongation sequence length of 15 randomers had better coverage evenness than an elongation sequence length of 10 randomers, as determined by the lower coverage coefficient of variance (coverage CV). DV, Q non-HS, and QE non-HS refer to the enzymes used for the study.

FIG. 17 demonstrates results of studies performed to understand the impact of polymerase and randomer length on coverage completeness. FIG. 17 plots the fraction of the molecules' sequence that is covered by the short reads as a metric for variation in coverage. DV, Q non-HS, and QE non-HS refer to the enzymes used for the study.

Figure 18:
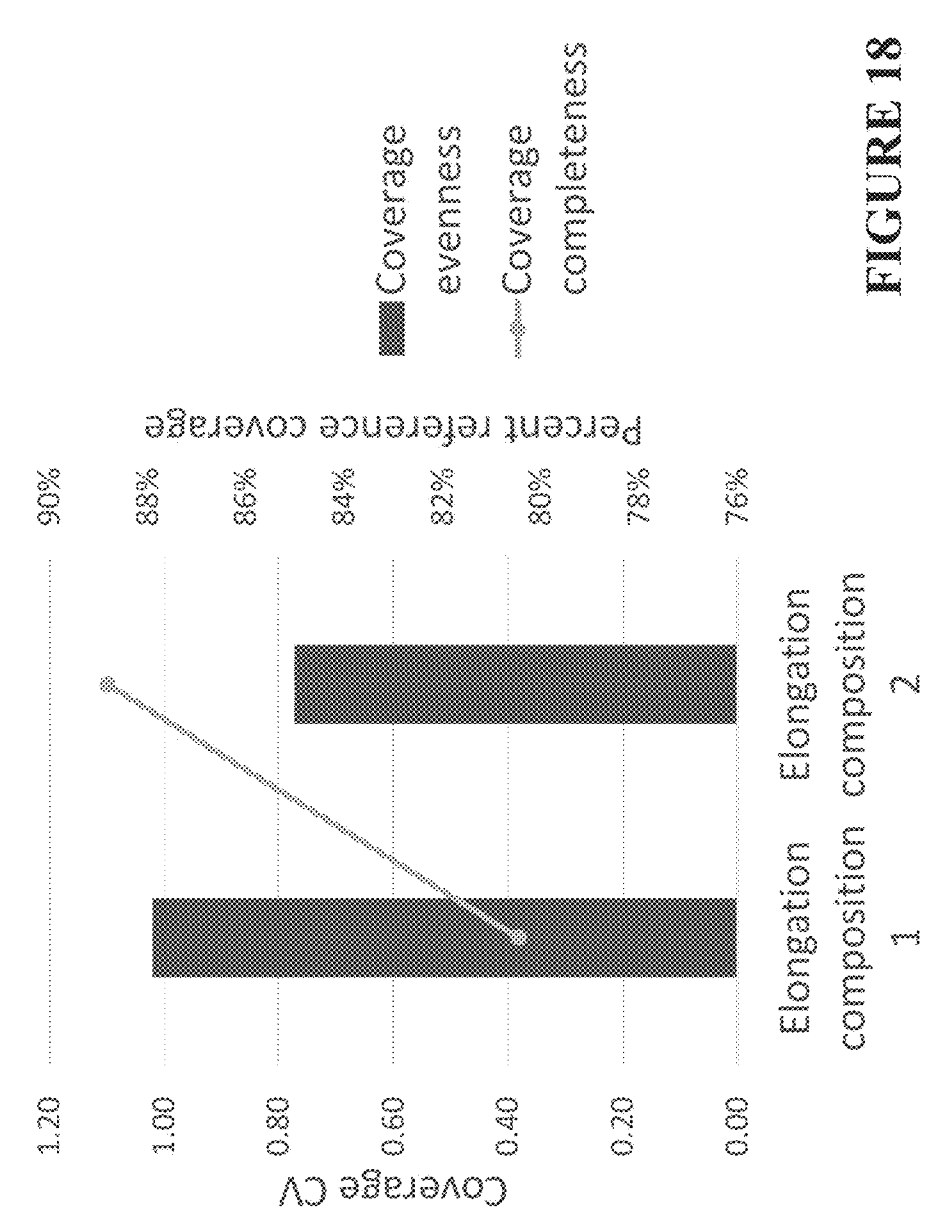
FIG. 18 illustrates impact of elongation sequence composition on coverage evenness and completeness of the tagged long DNA molecules.

FIG. 18 demonstrates that the composition of the elongation sequence, i.e. the combination of primers each containing a different design of the elongation sequence, impacted the evenness and completeness of the intramolecular elongation. Parameters that can be modified for different elongation reactions include, for example, concentration of DNA and buffer composition.

The rate of the ssDNA intramolecular elongation reaction was controlled using temperature and nucleotide concentration such that the length of DNA polymerized may not exceed the read length of NGS. Different intramolecular elongation reaction conditions led to different coverage evenness and completeness of coverage of the originally tagged DNA molecule.

Figure 19:
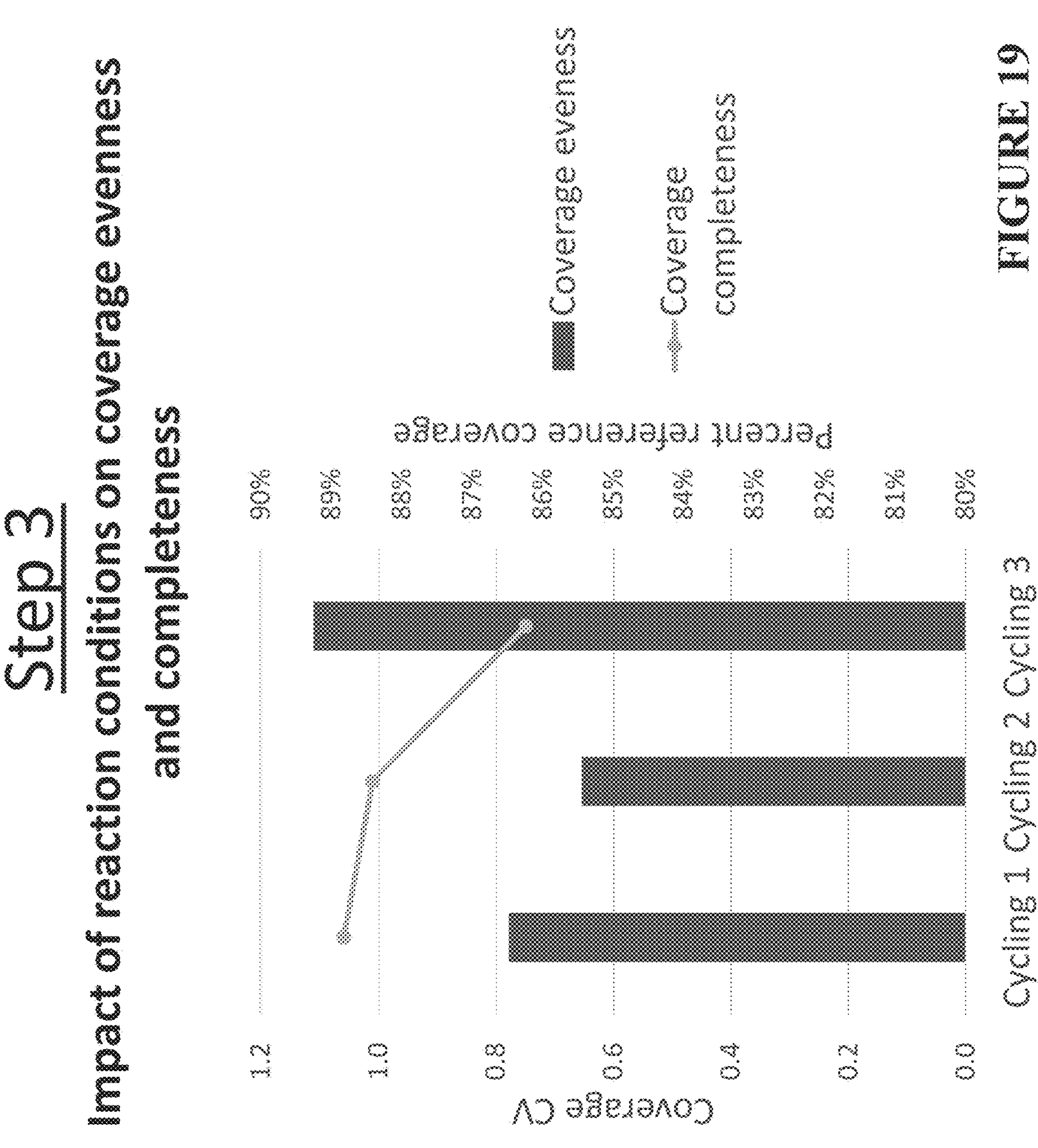
FIG. 19 illustrates the impact of reaction condition on the coverage evenness and completeness of the tagged long DNA molecules.

FIG. 19 demonstrates that Cycling 1 and Cycling 2 had better coverage evenness compared to Cycling 3, as determined by the lower coverage coefficient of variance (coverage CV). Coverage completeness was lower for Cycling 3 compared to Cycling 1 and Cycling 2, as determined by the percent reference coverage. Cycling 1, 2, and 3 were performed with 1, 5, and 10 cycles, respectively, and a temperature of 40 degrees C., 45 degrees C., and 50 degrees C., respectively, in the elongation step.

The newly formed uniquely barcoded dsDNA molecules, made of self-elongated ssDNA molecules, were then fragmented. Each amplicon was fragmented into fragments of different lengths depending on the location of the breakage site. The DNA fragments obtained were tagged at their 5' ends or 3' ends. If the DNA fragments were fragmented into more than two fragments, the fragments were devoid of tags. Fragments devoid of a tags were not observed, and were excluded from further analysis. Following fragmentation, the fragmented DNA was blunted and 5' phosphorylated. In some experiments, the newly formed and uniquely barcoded dsDNA molecules, made of self-elongated ssDNA molecules, were blunted.

FIG. 21 illustrates the ligation of a second sequencing adaptor (SA2) to each of the fragments. The resulting molecules were used to prepare a standard NGS library prep using sequence adaptors.

FIG. 22 illustrates the ligation of SA2 to each of the fragments. Universal PCR was performed on the fragments with SA2 using primers complementary to the 1st and the second sequencing adaptor to generate libraries suitable for sequencing.

The uniquely tagged DNA molecules were amplified in a mixture by PCR. Amplification was carried out using primers directed to a universal sequence present in all of the unique tags, which created multiple copies of each of the uniquely tagged DNA molecules.

The DNA molecules were then prepared for standard NGS sample preparation by shearing the DNA molecules into sequences having lengths suitable for NGS. The DNA molecules were sheared into sequences about 100-200 bp, or about 250-400 bp. During fragmentation of the ligated DNA, certain fragments lost their barcode sequences. These fragments were excluded from further analysis. Due to the multiplicity of the ligated fragments, sheared fragments containing barcode sequences covered the entire length of the original DNA molecule.

The short-read sequencing provided sequence information of the fragments of the DNA molecule as well as the molecule-specific barcode. The barcode served as an identifier of the original molecule from which the fragment can be derived, thereby allowing the phasing of the sequence. To determine that a fragment having a 3' tag was derived from an original DNA molecule as another fragment having a 5' tag (different from the 3' tag), pairing of 5' tags and 3' tags was sometimes necessary.

Figure 30:
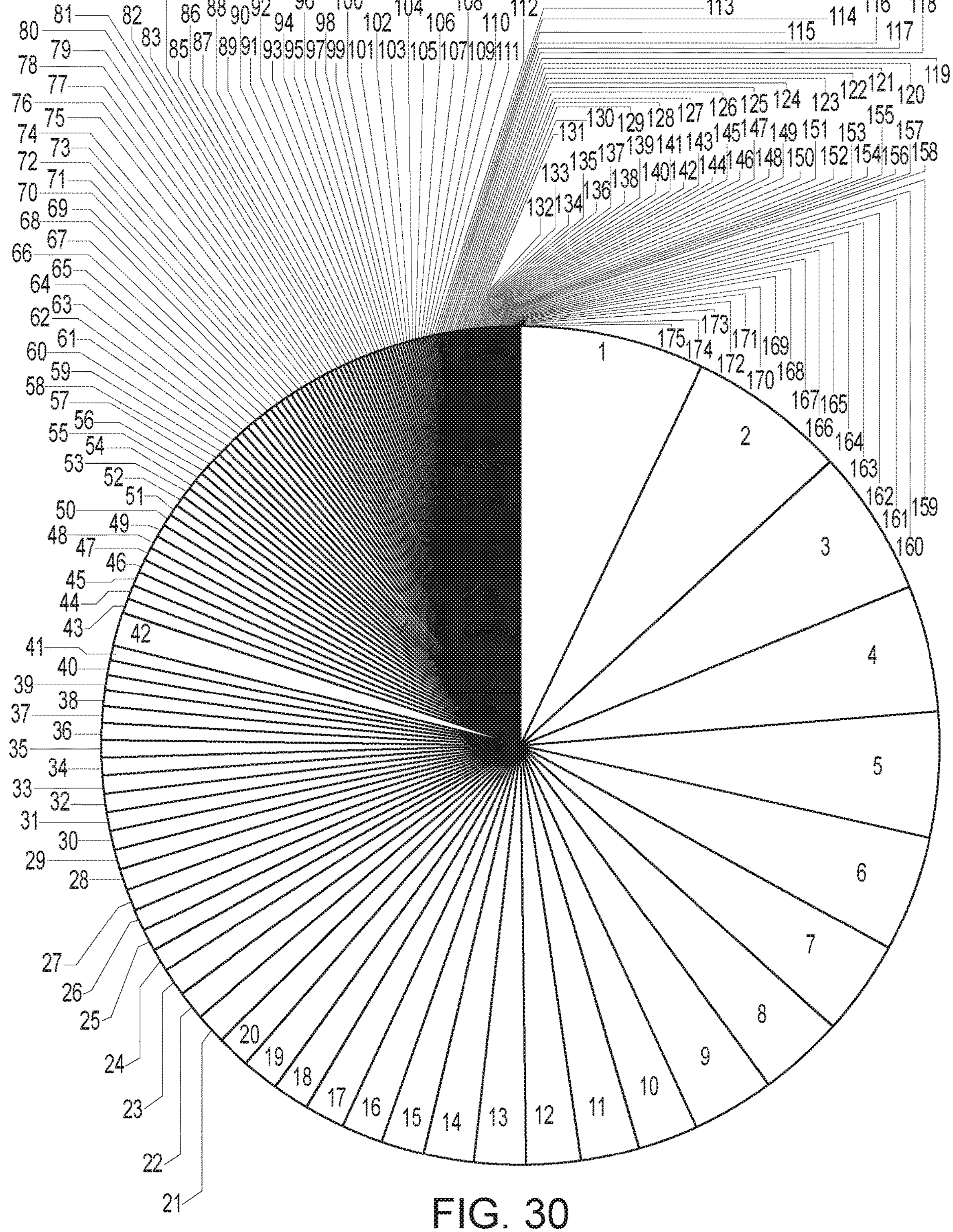
FIG. 30 illustrates the abundance and classification of the phased tagged 16s molecules that originate from complex microbiome.
Figure 32:
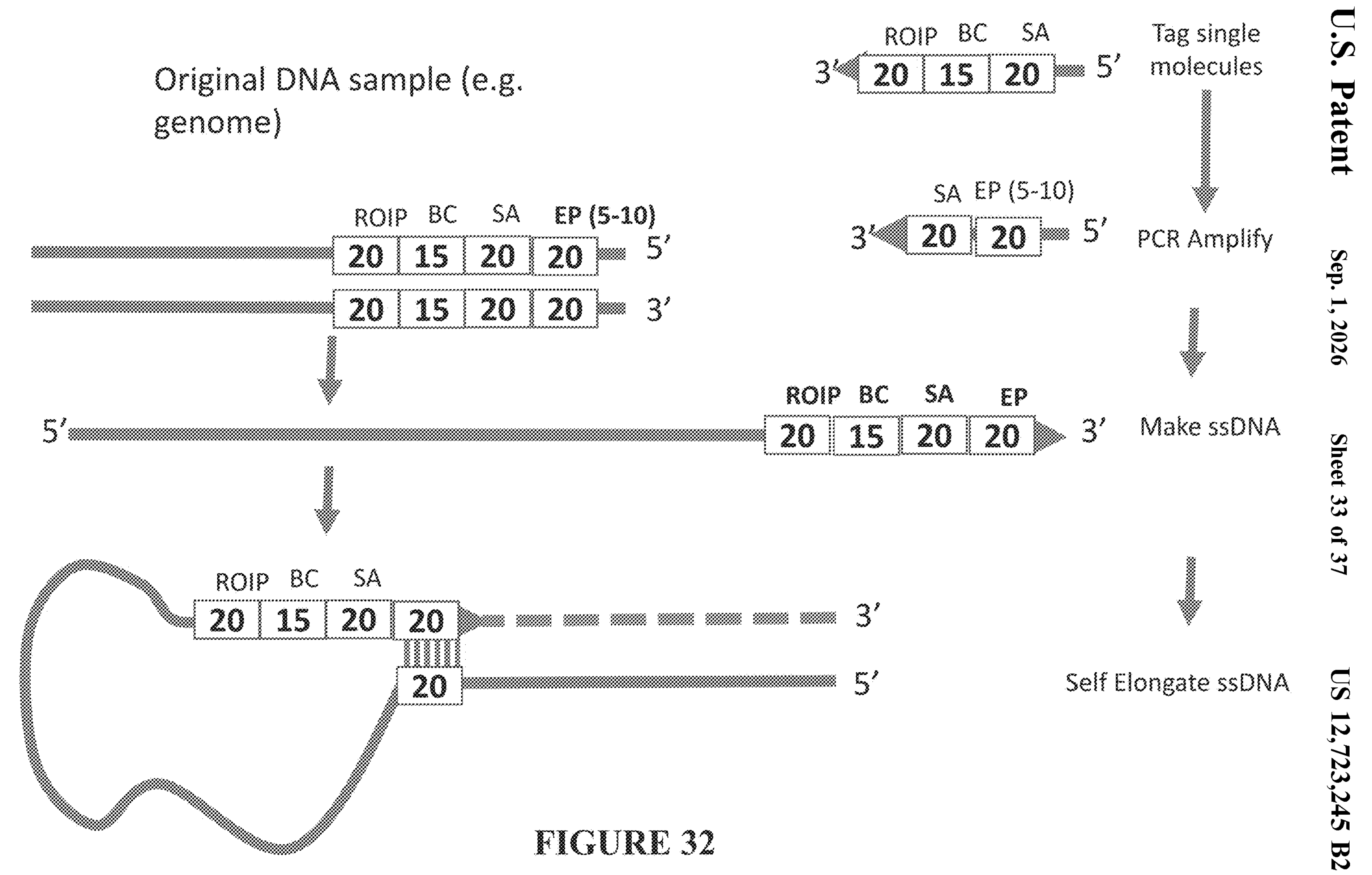
FIG. 32 illustrates a scheme for generating a tagged stem-loop nucleic acid of the disclosure.
Figure 33:
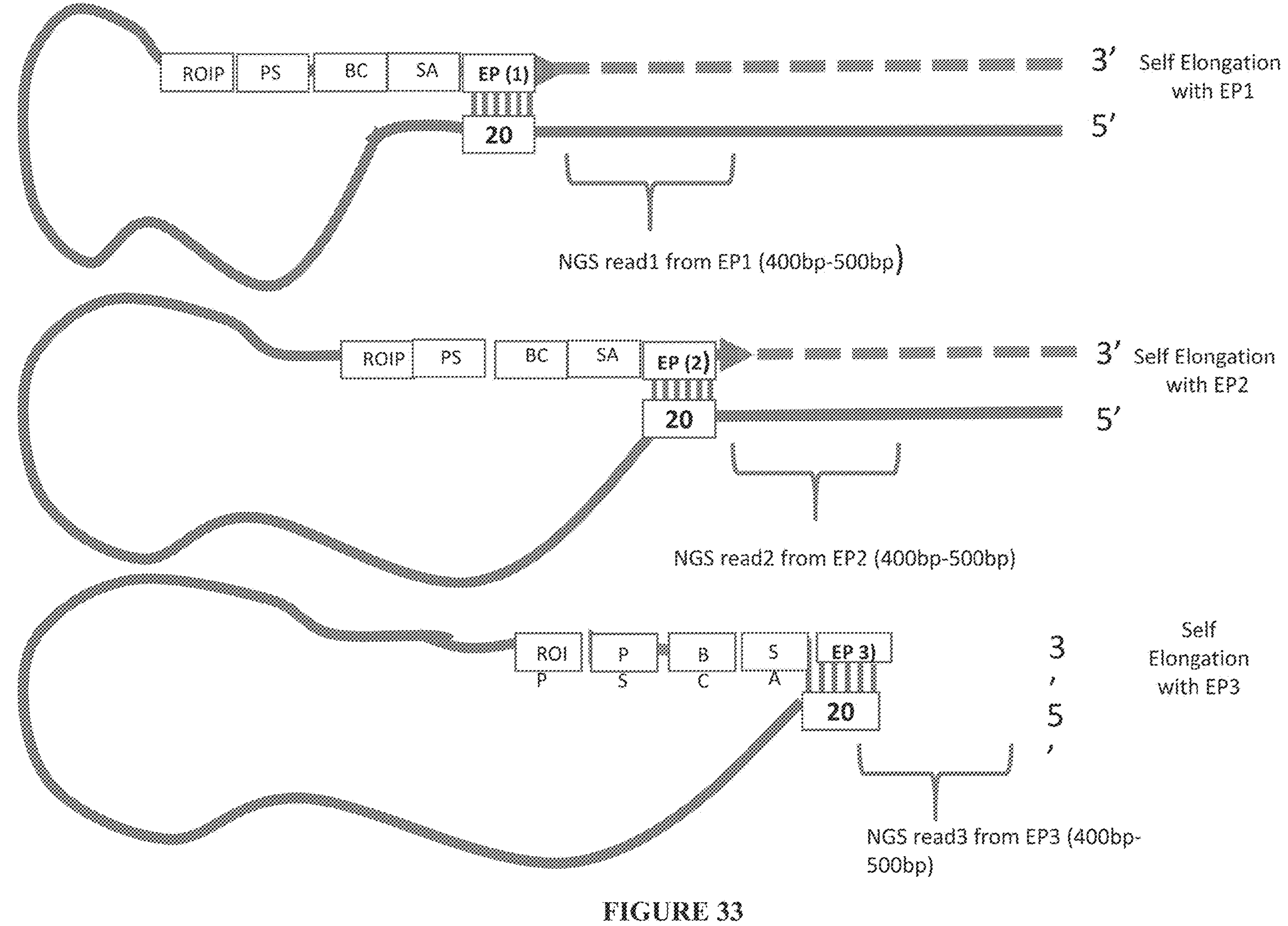
FIG. 33 illustrates that, for a single long nucleic acid (e.g., DNA) molecule, a number of different self-elongation reactions can occur using different elongation sequences, which can collectively distribute the barcode segment throughout the length of the long single stranded nucleic acid molecule.

FIG. 30 illustrates an example of clustering short-read sequences using molecule-specific barcodes, which was used to construct the de novo assembly of the original molecules using the short-read sequences. The abundance and class of the original organisms from which the original DNA molecules originated were identified.

Example 2: Sequence-Dependent Tagging of Nucleic Acid in Complex Mixtures

Similar to the method described in Example 1, a complex mixture of dsDNA (or RNA molecules converted to DNA) of varying lengths was obtained. Each of the DNA molecules in the mixture was tagged and/or amplified using a unique terminal adaptor comprising a molecular barcode that was a unique molecular identifier and self-elongation sequence. In some experiments, the self-elongation sequence was appended during the tagging phase or the amplification phase. The mixture of DNA molecules was tagged such that each DNA molecule in the mixture received a unique tag. Alternatively, the mixture of DNA molecules was uniquely tagged using DNA elongation-based tagging using a DNA polymerase and a barcoded primer complementary to one or more of the DNA termini. In some experiments, the molecules were tagged from the outset during DNA synthesis in the case of synthetic DNA libraries. If the barcode was integrated into the molecules of the library during DNA synthesis, the barcode comprises random sequences or a collection of known sequences that were equal or larger than the number of unique DNA molecules synthesized.

The uniquely tagged DNA molecules were amplified in mixture by PCR. PCR was performed using primers directed to a universal sequence present in all of the unique tags, thereby creating multiple copies of each of the uniquely tagged DNA molecules.

The terminal adaptor was designed such that the 3' end of its complementary sequence in the opposing strand was complementary to a designated internal sequence of the DNA molecule the terminal adaptor was tagging. The complementary 3' sequence functioned as an elongation primer in an intramolecular elongation reaction in subsequent steps.

In some experiments, the dsDNA molecules were converted into ssDNA by enzymatic degradation via the Lambda Exonuclease of a phosphorylated strand. The enzymatic degradation specifically degraded one strand of the uniquely barcoded DNA molecules to obtain a pool of uniquely barcoded and elongation-primed ssDNA molecules.

The dsDNA molecules were converted into ssDNA by immobilizing one strand of the uniquely barcoded DNA molecules and separating the complementary strand by alkaline denaturation to obtain a pool of uniquely barcoded and elongation-primed ssDNA molecules. The dsDNA molecules were also converted into ssDNA by heat denaturation of the dsDNA molecules in dilute conditions prior to performing elongation reaction, thereby effectively rendering each strand of the DNA into ssDNA molecules.

Figure 20:
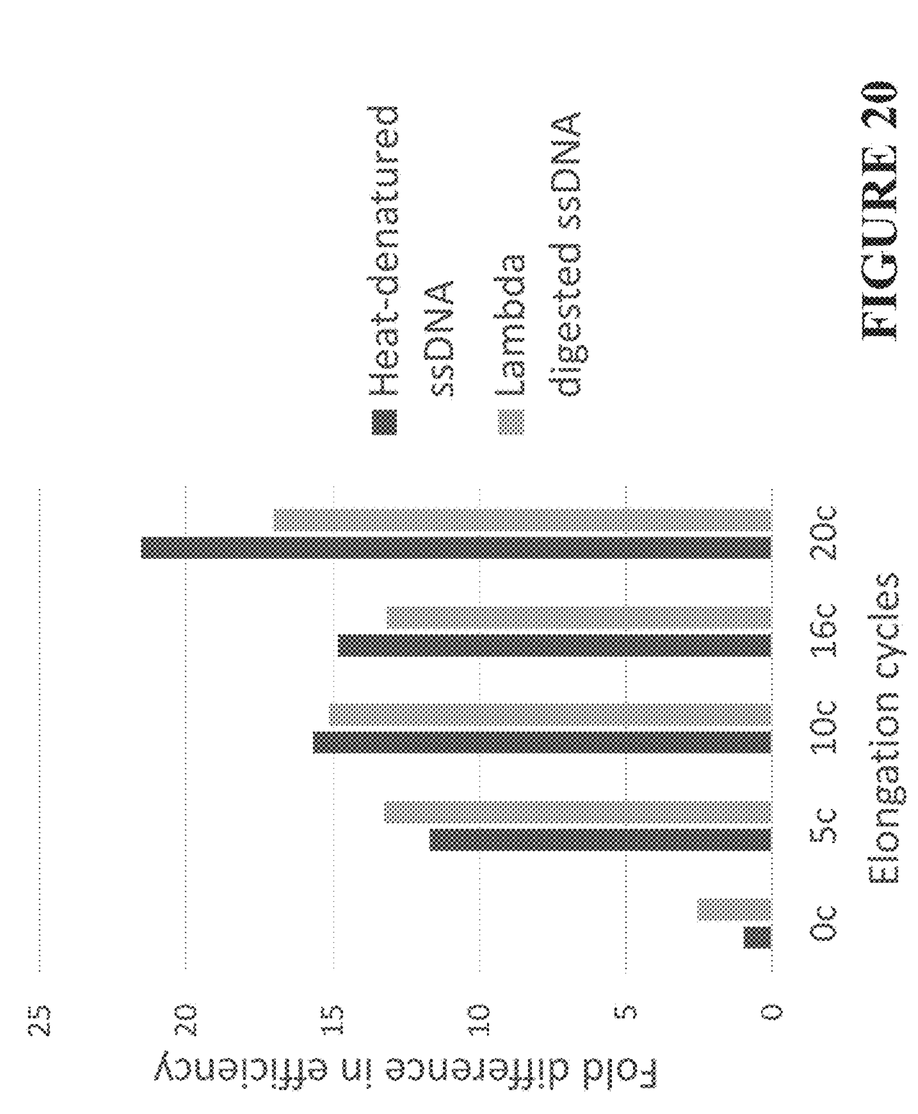
FIG. 20 illustrates efficiency difference observed with different methods of generating single-stranded nucleic acid from double-stranded nucleic acid.

FIG. 20 demonstrates a comparison of the elongation efficiency between dsDNA that has been digested with Lambda Exonuclease and dsDNA that has undergone heat denaturation prior to elongation.

In a sequence dependent self-elongation step, at designated sequence-specific loci, the self-elongation sequence at the 3'-end of the terminal adaptor served as a target sequence complementary to an internal sequence of the uniquely barcoded and elongation-primed ssDNA molecules in the mixture (FIG. 23). A polymerase was used to extend the self-elongation sequence, which generated a new mixture of uniquely barcoded, partially dsDNA molecules. To avoid exceeding the NGS read length, the self-elongation reaction was limited to 100-300 bp by controlling the temperature and/or nucleotide concentration. The new dsDNA molecules were then blunted, and a sequencing adaptor was attached to the newly generated dsDNA terminus.

The new dsDNA molecules were then fragmented, and adaptors were ligated to the newly generated dsDNA ends. The preparation included shearing the newly elongated dsDNA into sequences having lengths suitable for sequencing.

If the original molecule had terminal tags on both the 5' end and the 3' end, most of the sheared fragments were devoid of a tag or included both tags because of the juxtaposition of the 5' and 3' tags. When tags were present at both the 5' end and 3' end of a molecule, the tag pairs can be identified.

The length of the self-elongation reaction was not explicitly limited, and the sequence length of the sequencing library was controlled using a PCR primer extension that included a sequence complementary to the newly formed dsDNA downstream of the elongation loci and a universal sequence that was suitable for NGS.

The PCR primer extension after intramolecular elongation was conducted in parallel reactions or in a multiplexed reaction. Universal PCR was performed using sequencing adaptors to generate sequencing-ready libraries. Similar to Example 1, the short-read sequencing provided sequence information of the fragments of the DNA molecules and the molecule-specific barcodes. The barcodes served as identifiers of the original molecules from which the fragments were derived, thereby allowing the phasing of the sequences.

Figure 24:
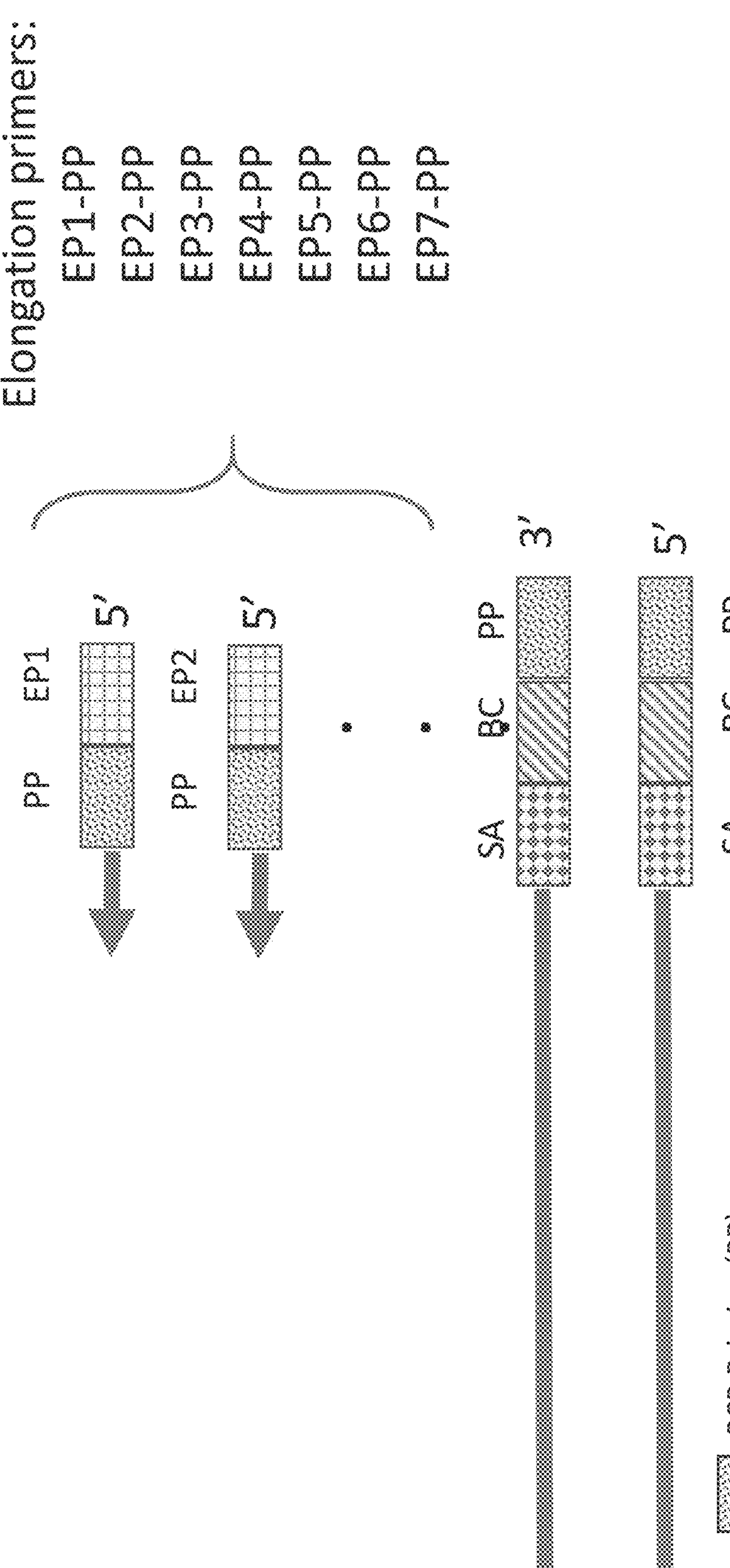
FIG. 24 illustrates the amplification of tagged DNA molecules with primers comprising different elongation sequences.

FIG. 24 illustrates an example of a sequence-dependent intramolecular elongation, where the tagged DNA was amplified with the elongation sequence. The tagged long DNA molecules were amplified with a mixture of elongation primers containing elongation sequences that spanned the length of a 16s rRNA gene. The exact primer sequences can be found in TABLE 1.

TABLE 1 describes the primer sequences used to amplify tagged DNA molecules, including the locations that the elongation sequences correspond to.

TABLE 1

| Primer Name | Sequence | Location of complementarity* |
|---|---|---|
| EP1 | CCTACGGGRSGCAGCAGCAGCACGTCATGCAC (SEQ ID NO: 1) | 318-334 |
| EP2 | AGCMGCCGCGGTCAGCACGTCATGCAC (SEQ ID NO: 2) | 472-483 |
| EP3 | GGATTAGATACCCBDGTAGTCCAGCACGTCATGCAC (SEQ ID NO: 3) | 737-757 |
| EP4 | AAACTYAAARRAATTGACGGCAGCACGTCATGCAC (SEQ ID NO: 4) | 858-877 |
| EP5 | GCATGGCTGYCCAGCACGTCATGCAC (SEQ ID NO: 5) | 1004-1014 |
| EP6 | TGYACWCACCGCAGCACGTCATGCAC (SEQ ID NO: 6) | 1342-1352 |
| EP7 | AAGTCGTAACAAGCAGCACGTCATGCAC (SEQ ID NO: 7) | 1443-1455 |

*Reference sequence location based on CP003046.1:192512-194014 *Rhodospirillum rubrum* F11

Figure 25:
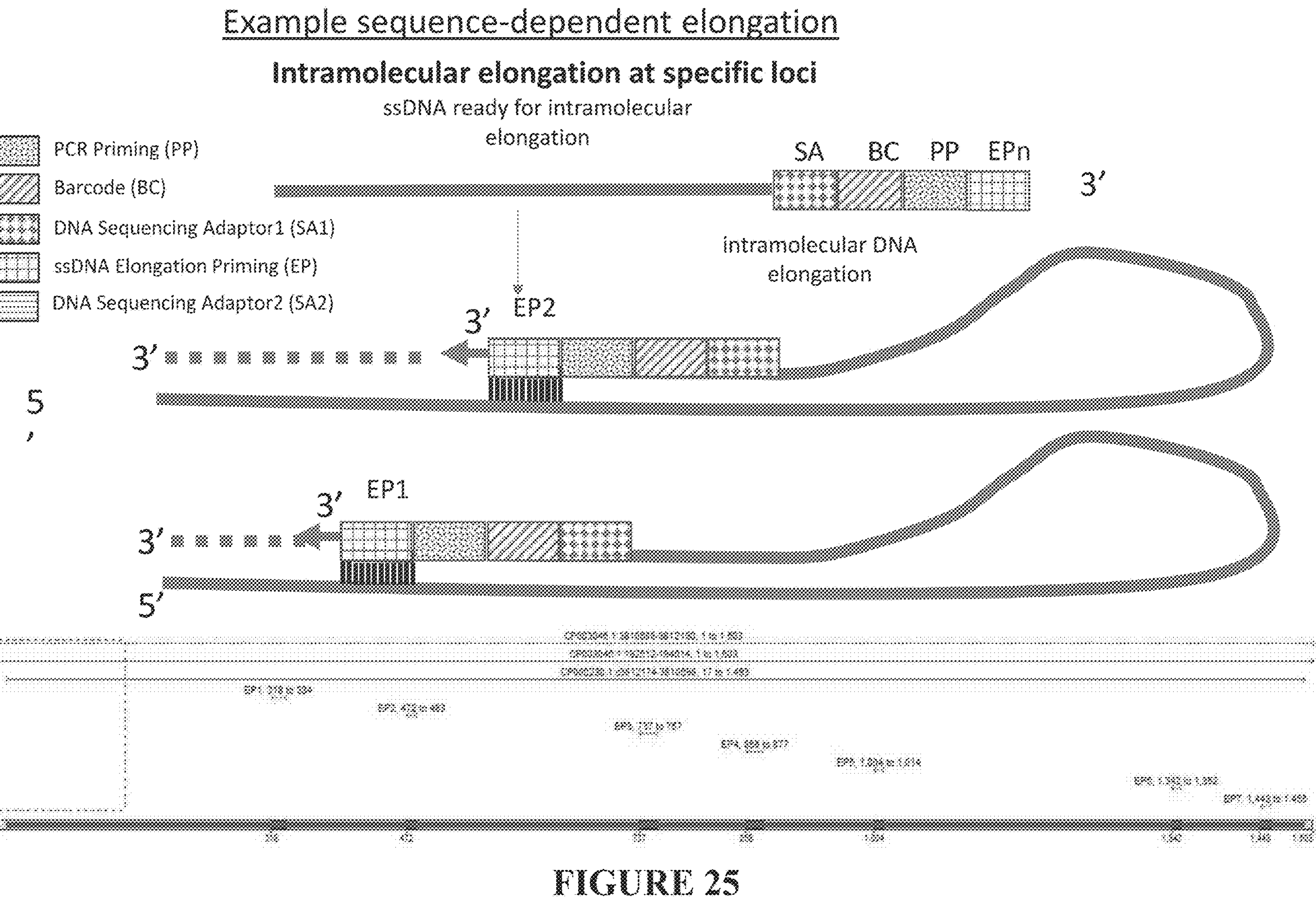
FIG. 25 illustrates an example of sequence-dependent elongation using different elongation priming sequences that anneal to specific loci.

FIG. 25 illustrates an example of a sequence-dependent intramolecular elongation, where intramolecular elongation was initiated at specific loci. The bottom panel of FIG. 25 illustrates an alignment of the sequences described in the figure to their actual position along the sequence of the gene that is being phased.

Figure 26:
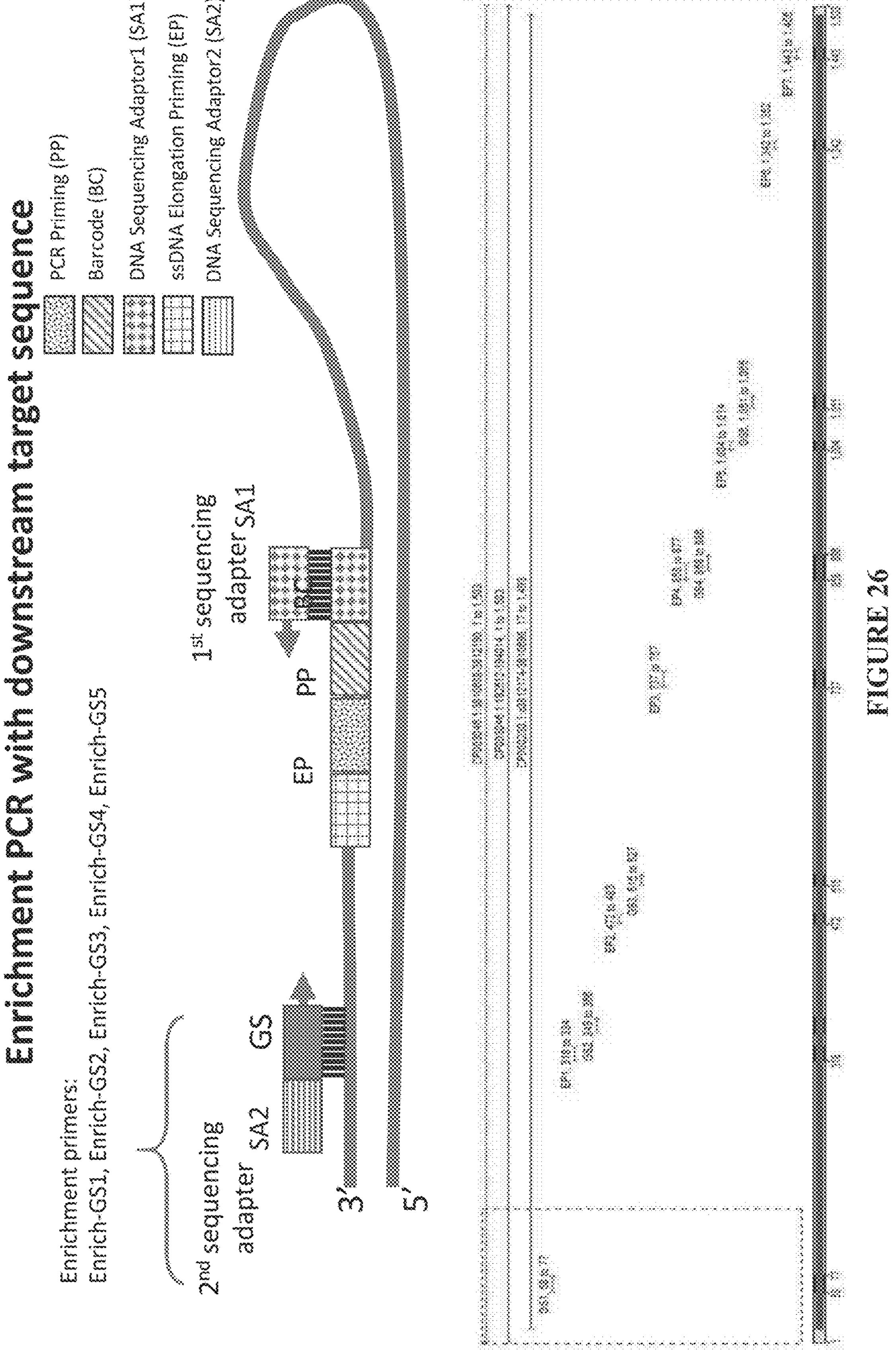
FIG. 26 illustrates an example of enriching elongated products using amplification primers comprising a sequencing adaptor and a target-specific sequence that is specific for a locus downstream of the elongation loci.

FIG. 26 illustrates an example of a sequence-specific intramolecular elongation that was terminated at a known site downstream of the elongation loci. In FIG. 26, GS refers to a gene-specific portion of the primer.

After the amplified dsDNA was converted into ssDNA using heat inactivation under dilute conditions, each ssDNA elongated at the specific locus that was complementary to the elongation sequence at the 3' terminal end. Collectively, the elongation loci spanned the length of the 16s rRNA gene (FIG. 25). After intramolecular elongation, the elongated ssDNA was amplified and enriched using sequencing adaptors and primers containing specific target sequences that were downstream of the elongation loci (FIG. 26). The exact primer sequences for the enrichment primers are shown in TABLE 2.

TABLE 2 describes the primer sequences used to amplify elongated DNA molecules, including the locations that the target sequences downstream of elongation loci corresponded to.

TABLE 2

| Primer Name | Sequence | Location of complementarity |
|---|---|---|
| Enrich-GS1 | GTGACTGGAGTTCAGACGTGTGCTCTTCCGATCTTNA NACATGCAAGTCGRRCG (SEQ ID NO: 8) | 58-77 |
| Enrich-GS2 | GTGACTGGAGTTCAGACGTGTGCTCTTCCGATCTCAA TGGRSGVRASYCTGA (SEQ ID NO: 9) | 349-366 |
| Enrich-GS3 | GTGACTGGAGTTCAGACGTGTGCTCTTCCGATCTAYT GGGYDTAAAG (SEQ ID NO: 10) | 515-527 |
| Enrich-GS4 | GTGACTGGAGTTCAGACGTGTGCTCTTCCGATCTGAA TTGACGGGGRCCCGCA (SEQ ID NO: 11) | 868-886 |
| Enrich-GS5 | GTGACTGGAGTTCAGACGTGTGCTCTTCCGATCTYAA CGAGCGMRACCC (SEQ ID NO: 12) | 1051-1065 |

*Reference sequence location based on CP003046.1:192512-194014 *Rhodospirillum rubrum* F11

The short-read sequences were clustered using the molecule-specific barcodes, which were constructed into discontiguous regions of the original molecules using de novo assembly from the short-read sequences and characterized into different classes of the original organisms.

Figure 27:
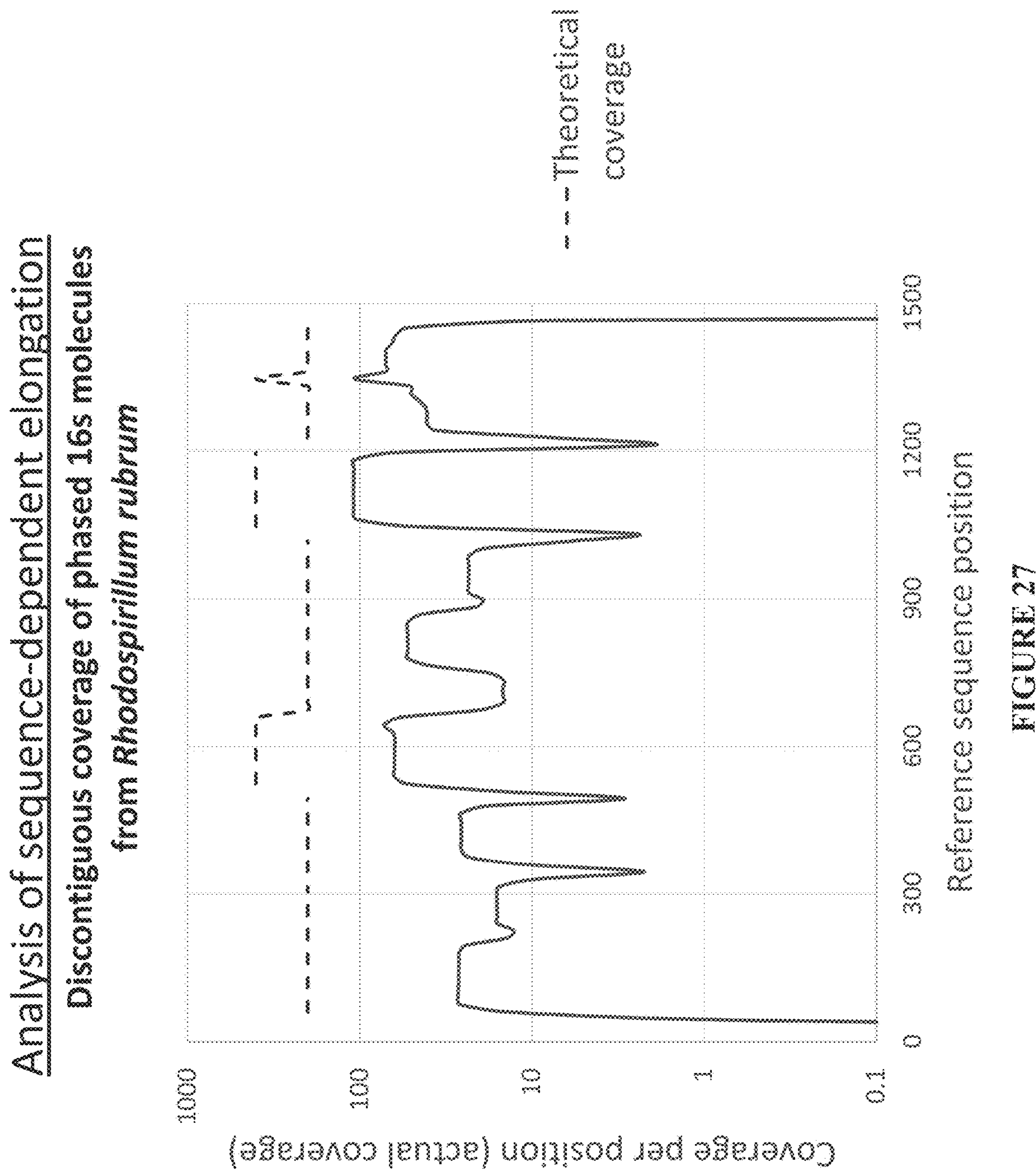
FIG. 27 illustrates the locations of the short-read sequence information after de novo assembly and reference mapping using tagged dsDNA that originate from *Rhodospirillum rubrum.*
Figure 28:
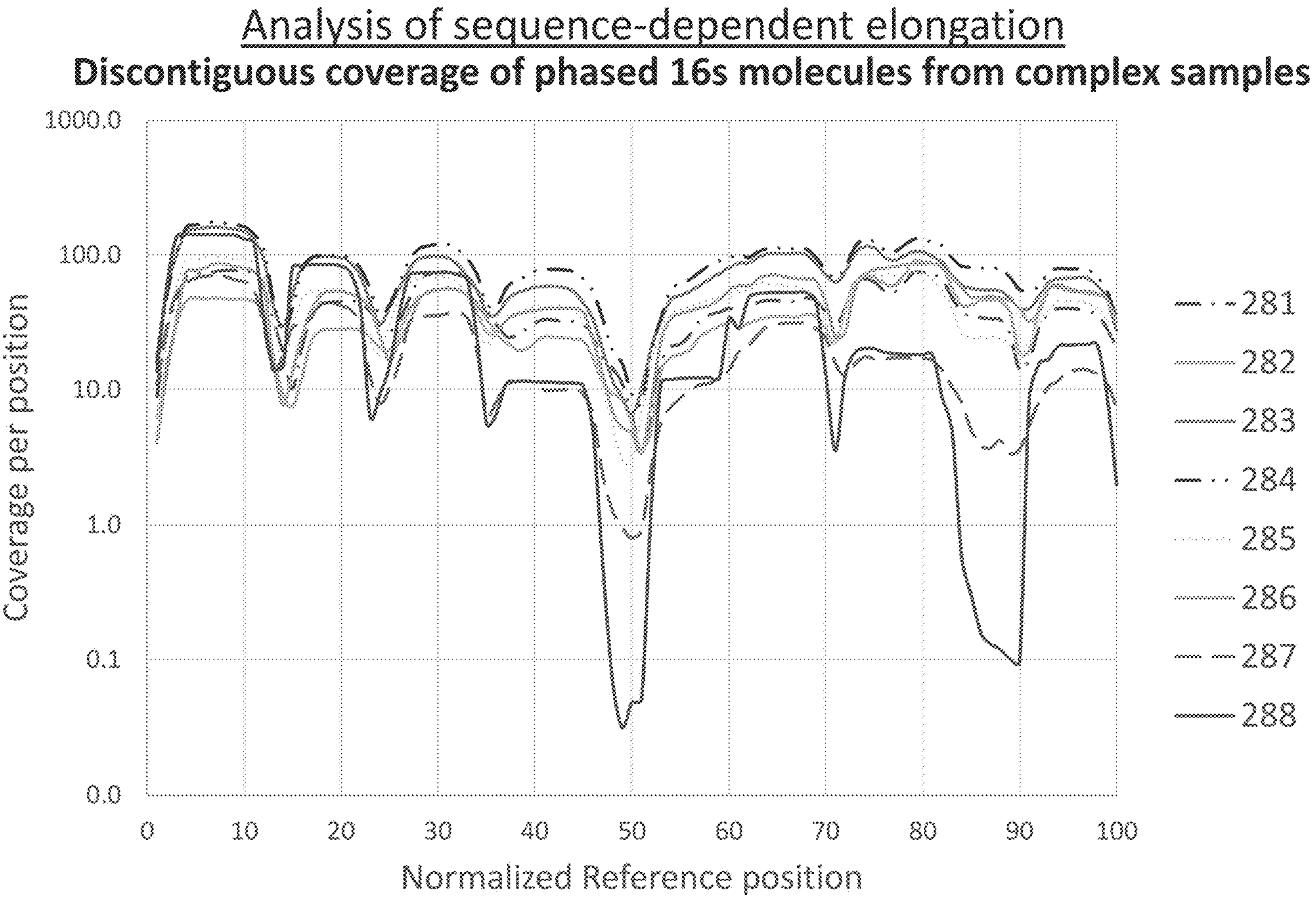
FIG. 28 illustrates the locations of the short-read sequence information after de novo assembly and reference mapping using tagged dsDNA that originate from complex microbiome.

FIG. 27 exhibits the sequence coverage of the short-read sequence information on an original long nucleic acid molecule of the 16s rRNA gene from *Rhodospirillum rubrum*. The black line (actual coverage) represents the short-read sequence information after de novo assembly and reference mapping. The dashed line (theoretical coverage) represents the location of the short-read sequence information based on the predicted location of the elongation loci and the enrichment target sequences downstream of the elongation loci. The theoretical coverage demonstrates discontiguous coverage of the long DNA molecule, with break points near positions 342, 500, and 1033, and overlapping short-read sequencing (i.e. higher coverage) at positions 515-665, 1051-1201, and 1340-1353. All three break points and higher coverage regions were observed in the actual coverage. The analysis was applicable to samples with a single organism that the 16s rRNA gene originated from (FIG. 27). FIG. 28 exhibits results obtained from samples of a complex microbiome.

Quantitative analysis of the de novo assembly and reference mapping was also be used to characterize the long nucleic acid molecules. When characterizing the identities of microorganisms in a complex microbiome sample, the 16s rRNA gene was used to identify and differentiate closely related species.

FIG. 29 shows that the quantitative analysis correctly determined the abundance of the 16s rRNA gene, as well as the identity of the molecule from which the 16s rRNA gene originated from. In this example, genomic DNA was extracted from *Rhodospirillum rubrum*.

EMBODIMENTS

In one aspect, the present disclosure provides a method for reducing coverage-bias of long DNA molecules in synthetic long-read (SLR) DNA sequencing, the method comprising generating uniquely barcoded parental long nucleic acid molecules, wherein each uniquely barcoded parental long nucleic acid molecule is evenly covered by a pool of shorter DNA fragments that span the parental sequence and share the same clonal barcode, thereby enabling phased short read sequencing with low coverage-bias of the long parental nucleic acid molecule, the method comprising:

- obtaining a mixture of fragments of a parental long nucleic acid molecule;
- tagging each of the fragments in the mixture with a unique terminal adaptor comprising a molecular barcode and a self-elongation sequence, thereby obtaining a pool of uniquely barcoded DNA molecules;
- amplifying each uniquely barcoded long DNA molecule to generate identical copies of each barcoded long DNA molecule;
- optionally, converting the double-stranded copies of uniquely barcoded DNA molecules to single stranded DNA, thereby obtaining a pool of uniquely barcoded and elongation-primed ssDNA molecules.

In one aspect, the present disclosure provides a method for reducing coverage-bias of long DNA molecules in synthetic long-read (SLR) DNA sequencing, the method comprising generating uniquely barcoded parental long nucleic acid molecules, wherein each uniquely barcoded parental long nucleic acid molecule is evenly covered by a pool of shorter DNA fragments that span the parental sequence and share the same clonal barcode, thereby enabling phased short read sequencing with low coverage-bias of the long parental nucleic acid molecule, the method comprising:

- obtaining a mixture of fragments of a parental long nucleic acid molecule;
- tagging each of the fragments in the mixture with a unique terminal adaptor comprising a molecular barcode, thereby obtaining a pool of uniquely barcoded DNA molecules;
- amplifying each uniquely barcoded long DNA molecule to generate identical copies of each barcoded long DNA molecule;
- appending the DNA molecule with self-elongation sequence, such that different copies of the uniquely barcoded DNA molecules have different self-elongation sequences;
- optionally, converting the double-stranded copies of uniquely barcoded DNA molecules to single stranded DNA, thereby obtaining a pool of uniquely barcoded and elongation-primed ssDNA molecules.

In some embodiments, the molecular barcode can be comprised entirely of a random sequence.

In some embodiments, the molecular barcode comprises a combination of a random molecule-specific sequence and a known sequence, wherein the known sequence can be used to identify the sample from which multiple parental nucleic sequences originate.

In some embodiments, the molecular barcode comprises an entirely known sequence, including both a molecule-specific sequence and a sample-specific sequence.

In some embodiments, the double-stranded copies of uniquely barcoded DNA molecules can be converted to ssDNA by enzymatic degradation.

In some embodiments, the double-stranded copies of uniquely barcoded DNA molecules can be converted to ssDNA by binding one of the strands of the dsDNA to a Streptavidin-coated surface and releasing the other strand through washing and/or denaturation.

In some embodiments, the double-stranded copies of uniquely barcoded DNA molecules can be converted to ssDNA by heat or alkaline denaturation under dilute conditions.

In some embodiments, the double-stranded copies of uniquely barcoded DNA molecules can be converted to ssDNA, and the method of the present disclosure further comprises using a DNA polymerase to intramolecularly elongate the ssDNA using a DNA polymerase starting from the 3' terminal self-elongation sequence, producing a mixture of uniquely barcoded, self-elongated, partially dsDNA molecules of varying lengths.

In some embodiments, the self-elongation sequences in the unique terminal adaptor can be at the 3'-end of the ssDNA and comprise random elongation priming sequences.

In some embodiments, the self-elongation sequences in the unique terminal adaptor can be at the 3'-end of the ssDNA and can be specific sequences designed to be self-complementary to internal sequences of the uniquely barcoded ssDNA molecules in the mixture.

In some embodiments, the self-elongated DNA molecules can be prepared for sequencing using a set of padlock probes that collectively span and cover the length of the DNA to be sequenced. In some embodiments, the self-elongation sequences can be designed to cover the entire length of the internal sequence of the uniquely barcoded DNA molecule.

In some embodiments, the self-elongation sequences can be designed to cover only specific regions of interest within the uniquely barcoded DNA molecule, hereby bridging regions of interest that can be separated by homologous regions and creating discontiguous phased sequences.

In some embodiments, the padlock probes have 5' terminal arms complementary to the region of interest primer (ROIP) on the ssDNA and the 3' terminal arm complementary to regions within the ssDNA that can be approximately one read-length apart.

In some embodiments, the 3' arms of the padlock probes can be approximately one read-length (100 bp-400 bp) apart.

In some embodiments, each padlock probe copies via elongation both the barcode information within each ssDNA and the sequence of interest.

In some embodiments, each padlock probe copies via elongation sequencing-primer sequence information present within each ssDNA.

In some embodiments, each padlock probe contains DNA sequencing adaptors that prime a padlock library for PCR using universal primers.

In some embodiments, each padlock probe can be circularized via ligation after the information is copied.

In some embodiments, the padlock probes can be prepared for next generation sequencing (NGS) using PCR with two universal primers.

In some embodiments, the length of elongation can be limited to, on average, the read-length of NGS by controlling the temperature and nucleotide concentration of the DNA polymerase-driven self-elongation reaction.

In some embodiments, the length of elongation may not be limited, but the length of the sequencing insert may be limited by selecting PCR extension primers that include complementary sequences that can be downstream of the elongation loci and sequencing adaptors for NGS.

In some embodiments, the elongated DNA can be blunted at its only exposed terminus, and a sequencing adaptor can be ligated at the blunted terminus.

In some embodiments, the method of the present disclosure further comprises:

- fragmenting the uniquely barcoded self-elongated DNA;
- ligating sequencing adaptors to the fragmented dsDNA and preparing them for NGS; and
- obtaining sequence information from the uniquely barcoded dsDNAs.

In some embodiments, the length of elongation may not be limited, but the length of the sequencing insert may be limited by choosing a frequency of fragmentation that can be suitable for the read-length of the NGS method.

In some embodiments, the method of the present disclosure further comprises amplifying the mixture with universal primers spanning the region of interest.

In some embodiments, the method of the present disclosure further comprises amplifying the mixture with a set of sequence specific primers that collectively evenly cover the original nucleic acid molecule and add NGS sequencing adaptors.

In some embodiments, the method of the present disclosure further comprises amplifying the mixture with a set of sequence specific primers that cover regions of interests, collectively produce a discontiguous sequence of the original nucleic acid molecule, and add NGS sequencing adaptors.

In some embodiments, the method of the present disclosure further comprises:

- fragmenting the uniquely barcoded self-elongated DNA;
- ligating adaptors to the fragmented DNA; and
- obtaining sequence information from the uniquely barcoded dsDNA molecules using a standard NGS library prep.

In some embodiments, the present disclosure further comprises phasing the obtained sequences based on their molecular origin as indicated by the unique barcode.

In some embodiments, the amplification of the mixture of uniquely tagged DNA molecules can be performed using PCR primers specific to the shared sequences integrated into the unique molecular tags and universal adaptors.

In some embodiments, tagging the mixture of DNA molecules with unique tags comprises adding a unique tag to each DNA molecule using blunt end ligation.

In some embodiments, tagging the mixture of DNA molecules with unique tags comprises carrying out PCR with primers flanked by that include the unique tag.

In some embodiments, tagging the mixture of DNA molecules with unique tags comprises adding the unique tag during DNA synthesis.

In some embodiments, the average length of the DNA molecules in the mixture of DNA molecules can be in the range of 500-5000 bp.

In some embodiments, the average length of the DNA molecules in the mixture of DNA molecules can be in the range of 1000-3000 bp.

In one aspect, the present disclosure provides a DNA fragment containing at least:

(i) a segment that encodes a unique DNA barcode identifier; and (ii) a segment that encodes a primer for intra-molecular, DNA self-polymerization using a DNA polymerase.

In one aspect, the present disclosure provides a method for eliminating barcode overwriting during the multiplexed phases of synthetic long read sequencing sample preparation.

In some embodiments, unique barcoding adaptors can be assigned to single long DNA or RNA molecules and can be subsequently removed from the barcoding reaction prior to pooling multiple said reactions and performing the downstream sample preparation process in a multiplex of more than one reaction.

In some embodiments, the removal of the barcoding adaptor can be through enzymatic digestion of the barcoding adaptor using an exonuclease.

In some embodiments, the unique barcoding adaptor contains uracil and the removal of barcoding adaptor can be through enzymatic cleavage with uracil-DNA glycosylase and an endonuclease to remove the uracil.

In some embodiments, the removal of the unique barcoding adaptor can be through purification technologies such as solid phase reversible immobilization that removes small oligonucleotides.

In some embodiments, the removal of the unique barcoding adaptor can be through column-based solid phase extraction that removes small oligonucleotides.

In some embodiments, the removal of the unique barcoding adaptor can be through gel filtration.

In some embodiments, the removal of unique barcoding adaptor can be through any combination of methods described above.

In one aspect, the present disclosure provides a method for reducing the sequencing coverage required for phasing two or more short nucleic acid segments from a longer single nucleic acid molecule by selectively sequencing only those regions of interest and not the entire sequence of the longer nucleic acid molecule.

In some embodiments, the sequencing coverage for phasing the regions of interest can be determined by the length of the regions of interest and not by the length of the longer DNA molecules that they reside in.

In some embodiments, where if, for example, three regions of interest in a single molecule total 500 bp in length and can be spread out along a 20,000 base pair molecule the method will result in a 40 fold (20,000/500) decrease in sequencing coverage required since only 500 bp, as opposed to 20,000 bp, will be required to phase the three regions of interest.

In one aspect, the present disclosure provides a method for sequencing specific regions of long single DNA molecules, the method comprising generating uniquely barcoded parental long nucleic acid molecules, wherein specific, user defined and pre-determined regions segments of each uniquely barcoded parental long nucleic acid molecule can be sequenced by a pool of shorter DNA fragments copied from specific regions of the parental molecule and share the same clonal barcode, thereby enabling selective phasing of the long parental nucleic acid molecule using short read sequencing the method comprising:

obtaining a mixture of fragments of a parental long nucleic acid molecule;

tagging each of the fragments in the mixture with a unique terminal adaptor comprising a molecular barcode, thereby obtaining a pool of uniquely barcoded DNA molecules;

amplifying each uniquely barcoded long DNA molecule to generate identical copies of each barcoded long DNA molecule;

appending the DNA molecule with self-elongation sequence, such that different copies of the uniquely barcoded DNA molecules have different self-elongation sequences;

intramolecularly elongate the single stranded DNA using a DNA polymerase starting from the 3' terminal self-elongation sequence, producing a mixture of uniquely barcoded self-elongated at specific regions of interest dsDNA molecules of varying lengths; and appending a second sequencing adaptor and converting the short self-elongated molecules into double-stranded sequencing-ready libraries.

In some embodiments, the parental long nucleic acid molecule can be genomic DNA or amplified DNA products from genomic DNA.

In some embodiments, the parental long nucleic acid molecule can be RNA or complementary DNA (cDNA) reverse transcribed from RNA.

In some embodiments, the specific regions of interest can be separated by 200-25000 bp, that can be separated by 500-20000 bp, that can be separated by 1000-15000 bp.

In some embodiments, the specific regions of interest can be single nucleotide change; that can be the read length of the short-read sequencer; that can be longer than what can be covered by the read length of the short-read sequencer.

In some embodiments, the specific regions of interest can be exomes separated by introns, and that only specific exomes or a subset of the sequence within each exome can be amplified and reconstructed into phased synthetic long-read (SLR).

In some embodiments, the specific regions of interest can be single nucleotide polymorphisms (SNPs), copy number variation, or other sequence rearrangement events in genomic DNA and that the cis-trans (phased) relationships between the variants needs to be elucidated.

In some embodiments, the specific regions of interest can be single nucleotide polymorphisms (SNPs), copy number variation, or other sequence rearrangement events in RNA such as RNA splicing and RNA editing and that the phased relationship between the variants need to be elucidated.

What is claimed is:

1. A method comprising:

a) providing a sample comprising a plurality of nucleic acids, wherein said plurality of nucleic acids comprises a nucleic acid strand, wherein said nucleic acid strand comprises an adaptor comprising a molecular barcode;

b) appending an elongation sequence to said nucleic acid strand, wherein said elongation sequence is complementary to at least a portion of a nucleic acid sequence in said nucleic acid strand;

c) annealing said elongation sequence to said portion of said nucleic acid sequence in said nucleic acid strand, thereby generating a partially-duplexed nucleic acid strand, wherein said partially-duplexed nucleic acid strand comprises a 5' portion comprising a single-stranded region and a 3' portion comprising said elongation sequence in an intramolecular duplex with said portion of said nucleic acid sequence; and d) extending said elongation sequence with a polymerase using said 5' portion of said partially-duplexed nucleic acid strand as a template, thereby generating an extended nucleic acid, wherein said extended nucleic acid comprises a stem-loop structure comprising a hybridized region and an unhybridized region, wherein said hybridized region comprises a first strand and a second strand, wherein said first strand comprises a 5' end of said extended nucleic acid and said second strand comprises a 3' end of said extended nucleic acid, and wherein a 3' end of said unhybridized region comprises said molecular barcode.

2. The method of claim 1, wherein a 3' end of said nucleic acid strand comprises said adaptor.

3. The method of claim 1, wherein a 3' end of said adaptor comprises said elongation sequence.

4. The method of claim 1, wherein a 5' end of said second strand comprises said elongation sequence.

5. The method of claim 1, wherein said unhybridized region is 3' to said first strand.

6. The method of claim 1, wherein said nucleic acid strand comprises DNA.

7. The method of claim 1, wherein said nucleic acid strand is generated from RNA, and wherein the method further comprises reverse transcribing said RNA before step a).

8. The method of claim 1, further comprising appending said adaptor to a nucleic acid molecule to generate said nucleic acid strand comprising said adaptor.

9. The method of claim 8, wherein said appending is performed by ligation or by polymerase chain reaction (PCR).

10. The method of claim 8, further comprising purifying said nucleic acid strand comprising said adaptor after said appending.

11. The method of claim 10, wherein said purifying comprises use of solid phase reversible immobilization, column-based solid phase extraction, or gel filtration to remove one or more unappended adaptors.

12. The method of claim 1, further comprising amplifying said nucleic acid strand comprising said adaptor prior to step a).

13. The method of claim 1, further comprising denaturing a double-stranded DNA molecule comprising said adaptor prior to step a), thereby generating a single-stranded nucleic acid comprising said nucleic acid strand comprising said adaptor.

14. The method of claim 13, wherein said denaturing comprises:

a) biotinylating a strand of said double-stranded DNA molecule to generate a biotinylated double-stranded DNA molecule;

b) binding said biotinylated double-stranded DNA molecule to a streptavidin-coated surface; and c) washing said streptavidin-coated surface to release a non-biotinylated DNA strand, thereby denaturing said double-stranded DNA molecule.

15. The method of claim 13, wherein said denaturing comprises heating said double-stranded DNA molecule or alkaline denaturation.

16. The method of claim 1, wherein said elongation sequence comprises a random sequence.

17. The method of claim 1, wherein said elongation sequence is substantially or completely complementary to said portion of said nucleic acid sequence.

18. The method of claim 1, wherein said molecular barcode comprises a random or semi-random sequence.

19. The method of claim 1, wherein said plurality of nucleic acids in said sample comprises a first adaptor comprising a unique molecular barcode.

20. The method of claim 19, wherein said first adaptor in said plurality of nucleic acids further comprises a second barcode common to individual single-stranded nucleic acids within said plurality of single-stranded nucleic acids.

21. The method of claim 1, further comprising appending an additional adaptor to said extended nucleic acid.

22. The method of claim 21, wherein said appending is performed by ligating or by PCR.

23. The method of claim 21, wherein said additional adaptor is appended at a 3' end of said extended nucleic acid.

24. The method of claim 21, further comprising amplifying said extended nucleic acid appended to said additional adaptor.

25. The method of claim 1, further comprising annealing a padlock probe to said extended nucleic acid, wherein said padlock probe comprises a 5' end complementary to a region of interest primer sequence within said adaptor and a 3' end complementary to a region of said extended nucleic acid, wherein the 5' end and the 3' end are connected by a linker sequence.

26. The method of claim 25, further comprising extending said 3' end of said padlock probe to generate an extended nucleic acid comprising said padlock probe and sequence complementary to said portion of said nucleic acid sequence.

27. The method of claim 26, further comprising ligating a 5' end and a 3' end of said extended nucleic acid comprising said padlock probe and said sequence complementary to said portion of said nucleic acid sequence, thereby generating a circularized nucleic acid comprising said padlock probe and said sequence complementary to said portion of said nucleic acid sequence.

28. The method of claim 27, further comprising amplifying said circularized nucleic acid using a universal primer complementary to a universal sequencing adaptor sequence within said linker sequence of said padlock probe, thereby generating linearized nucleic acids comprising said molecular barcode of said nucleic acid and a sequence complementary to said universal primer.

29. A method comprising:

a) appending a first adaptor to a nucleic acid in a plurality of nucleic acids, thereby generating a barcoded nucleic acid comprising said first adaptor, wherein said first adaptor comprises a molecular barcode, wherein said nucleic acid comprises a first target region and a second target region;

b) amplifying said barcoded nucleic acid, thereby generating amplified barcoded nucleic acids;

c) appending an elongation sequence to a barcoded nucleic acid in said amplified barcoded nucleic acids, thereby generating a barcoded nucleic acid comprising said elongation sequence, wherein said elongation sequence is complementary to at least a portion of a nucleic acid sequence in a strand of said barcoded nucleic acid, wherein said strand comprises said elongation sequence and said first adaptor;

d) annealing said elongation sequence to said portion of said nucleic acid sequence in said strand of said barcoded nucleic acid, thereby generating a partially-duplex nucleic acid, wherein said partially-duplex nucleic acid comprises a 5' portion comprising a single-stranded region and a 3' portion comprising said elongation sequence in an intramolecular duplex with said portion of said nucleic acid sequence;

e) extending said elongation sequence with a polymerase using said 5' portion of said partially-duplex nucleic acid as a template, thereby generating an extended nucleic acid;

f) appending a second adaptor to said extended nucleic acid, thereby generating an extended nucleic acid comprising said first adaptor and said second adaptor, wherein said second adaptor comprises a sequence complementary to a sequencing primer; and g) amplifying said extended nucleic acid comprising said first adaptor and said second adaptor with a first primer and a second primer, wherein said first primer anneals to said first adaptor or a complement thereof, and wherein said second primer anneals to said second adaptor or a complement thereof.

* * * * *